(12) United States Patent
Julien et al.

(10) Patent No.: US 10,202,443 B2
(45) Date of Patent: Feb. 12, 2019

(54) TDP-43-BINDING POLYPEPTIDES USEFUL FOR THE TREATMENT OF NEURODEGENERATIVE DISEASES

(71) Applicant: UNIVERSITÉ LAVAL, Québec, (Québec) (CA)

(72) Inventors: Jean-Pierre Julien, Québec (CA); Claude Gravel, Québec (CA); Silvia Pozzi, Québec (CA)

(73) Assignee: UNIVERSITÉ LAVAL, QUÉBEC (CA)

( * ) Notice: Subject to any disclaimer, the term of this patent is extended or adjusted under 35 U.S.C. 154(b) by 0 days.

(21) Appl. No.: 15/532,909

(22) PCT Filed: Dec. 7, 2015

(86) PCT No.: PCT/CA2015/051280
§ 371 (c)(1),
(2) Date: Jun. 2, 2017

(87) PCT Pub. No.: WO2016/086320
PCT Pub. Date: Jun. 9, 2016

(65) Prior Publication Data
US 2017/0355756 A1 Dec. 14, 2017

Related U.S. Application Data

(60) Provisional application No. 62/088,012, filed on Dec. 5, 2014.

(30) Foreign Application Priority Data

Dec. 5, 2014 (CA) ..................................... 2874083

(51) Int. Cl.
C07K 16/18 (2006.01)
A61K 48/00 (2006.01)
C12N 15/86 (2006.01)

(52) U.S. Cl.
CPC .............. *C07K 16/18* (2013.01); *C12N 15/86* (2013.01); *A61K 48/00* (2013.01); *C07K 2317/24* (2013.01); *C07K 2317/35* (2013.01); *C07K 2317/52* (2013.01); *C07K 2317/54* (2013.01); *C07K 2317/55* (2013.01); *C07K 2317/569* (2013.01); *C07K 2317/622* (2013.01); *C07K 2317/76* (2013.01); *C07K 2317/82* (2013.01); *C12N 2750/14143* (2013.01)

(58) Field of Classification Search
None
See application file for complete search history.

(56) References Cited

U.S. PATENT DOCUMENTS

| | | |
|---|---|---|
| 8,598,339 B2 | 12/2013 | Timmermann et al. |
| 2003/0143540 A1 | 7/2003 | Matsuda et al. |
| 2009/0263824 A1 | 10/2009 | Lee et al. |
| 2010/0136573 A1 | 3/2010 | Petrucelli et al. |
| 2011/0034447 A1 | 2/2011 | Nonaka et al. |
| 2011/0065600 A1 | 3/2011 | Cairns et al. |
| 2011/0076723 A1* | 3/2011 | Min ........................ C07K 16/22 435/69.6 |
| 2011/0135658 A1* | 6/2011 | Zeng .................. A61K 31/7105 424/158.1 |
| 2011/0230551 A1 | 9/2011 | Gunatilaka et al. |
| 2011/0287953 A1 | 11/2011 | Huang et al. |
| 2012/0196815 A1 | 8/2012 | Timmermann et al. |
| 2013/0338039 A1 | 12/2013 | Mazed et al. |

FOREIGN PATENT DOCUMENTS

| | | | |
|---|---|---|---|
| EP | 2189526 | | 5/2010 |
| WO | WO 2004/110364 | | 12/2004 |
| WO | WO 2008/042190 | | 4/2008 |
| WO | WO 2008068048 | * | 6/2008 |
| WO | WO 2008/151055 | | 12/2008 |
| WO | WO 2009/008529 | | 1/2009 |
| WO | WO 2009/044119 | | 4/2009 |
| WO | WO 2010/015040 | | 2/2010 |
| WO | WO 2010/030395 | | 3/2010 |
| WO | WO 2010/053655 | | 5/2010 |
| WO | WO 2011/005628 | | 1/2011 |
| WO | WO 2011/151359 | | 12/2011 |
| WO | WO 2012/174666 | | 12/2012 |

OTHER PUBLICATIONS

Chen "Enhancement and destruction of antibody function by somatic mutation: unequal occurrence is controlled by V gene combinatorial associations" EMBO 14(12):2784-2794 (Year: 1995).*
Kussie "A Single Engineered Amino Acid Substitution Changes Antibody Fine Specificity" J immunol 152(1): 146-52 (Year 1994).*
Reitz "Toward precision medicine in Alzheimer's disease" Ann Trans Med 4(6):107 (Year: 2016).*
Stanford "Alzheimer's Prevention, Treatment and Research—A Q&A with Dr. Frank Longo" accessed on May 3, 2016 from stanfordhealthcare.org (Year: 2016).*
Aleyasin et al. "Nuclear factor-(κ).B modulates the p53 response in neurons exposed to DNA damage", J Neurosci 24, 2963-2973 (2004).

(Continued)

*Primary Examiner* — Adam Weidner
(74) *Attorney, Agent, or Firm* — Edward J. Baba; Bozicevic, Field & Francis LLP

(57) ABSTRACT

Provided herein are antigen-binding constructs such as antibodies that bind to the RRM-1 domain of TDP-43. The antigen-binding constructs are capable of blocking the interaction of TDP-43 with NF-κB in cells. Also provided herein are method of using the antigen-binding constructs in the treatment of diseases associated with TPD-43 proteinopathy, such as amyotrophic lateral sclerosis (ALS), frontotemperal lobar degeneration (FTLD), Lewy body disease and motor neuron disease.

11 Claims, 13 Drawing Sheets
Specification includes a Sequence Listing.

(56) References Cited

OTHER PUBLICATIONS

Arai et al. "TDP-43 is a component of ubiquitin-positive tau-negative inclusions in frontotemporal lobar degeneration and amyotrophic lateral sclerosis", Biochem Biophys Res Commun 351, 602-611 (2006).
Badadani et al. "VCP associated inclusion body myopathy and paget disease of bone knock-in mouse model exhibits tissue pathology typical of human disease", PLoS One 5, e13183 (2010).
Barbeito et al. "A role for astrocytes in motor neuron loss in amyotrophic lateral sclerosis", Brain Res Rev 47, 263-274 (2004).
Baumer, D et al. "TARDBP in amyotrophic lateral sclerosis: identification of a novel variant but absence of copy bumber variation", J Neurol Neurosurg Psychiatry 80, 1283-1285 (2009).
Beaulieu et al. "Late onset of motor neurons in mice overexpressing wild-type peripherin", J Cell Biol 147, 531-544 (1999).
Beaulieu et al. "Induction of peripherin expression in subsets of brain neurons after lesion injury or cerebral ischemia", Brain Res 946, 153-161 (2002).
Bergmann et al. "IκKα degradation and nuclear factor-κB DNA binding are insufficient for interleukin-1β and tumor necrosis factor-α-induced κB-dependent transcription Requirement for an additional activation pathway", J Biol Chem 273, 6607-6610 (1998).
Boillee et al. "ALS: a disease of motor neurons and their non-neuronal neighbors", Neuron 52, 39-59 (2006).
Boillee et al. "Onset and progression in inherited ALS determined by motor neurons and microglia", Science 312, 1389-1392 (2006).
Bose et al. "TDP-43 overexpression enhances exon 7 inclusion during the survival of motor neuron pre-mRNA splicing", J Biol Chem 283, 28852-28859 (2008).
Burrati et al. "Nuclear factor TDP-43 and SR proteins promote in vitro and in vivo CFTR exon 9 skipping", EMBO J 20, 1774-1784 (2001).
Cairns et al. "TDP-43 in familial and sporadic frontotemporal lobar degeneration with ubiquitin inclusions", Am J Pathol 171, 227-240 (2007).
Carpenter "Proximal axonal enlargement in motor neuron disease", Neurology 18, 841-851 (1968).
Cassel et al. "Development of a novel nonradiometric assay for nucleic acid binding to TDP-43 suitable for high-throughput screening using AlphaScreen technology", J Biomol Screen 15, 1099-1106 (2010).
Chang et al. "Molecular mechanism of oxidation-induced TDP-43 RRM1 aggregation and loss of function", FEBS Letters18, 587(6)., 575-82 (2013).
Chiang et al. "Deletion of TDP-43 down-regulates Tbc1d1, a gene linked to obesity, and alters body fat metabolism", Proc Natl Acad Sci USA 107, 16320-16324, (2010).
Clement et al. "Wild-type nonneuronal cells extend survival of SOD1 mutant motor neurons in ALS mice", Science 302, 113-117 (2003).
Cohen et al. "An acetylation switch controls TDP-43 function and aggregation propensity", Nat Commun 6, 5845 (27 pages) (2015).
Corbo et al. "Peripherin and neurofilament protein coexist in spinal spheroids of motor neuron disease", J Neuropathol Exp Neurol 51:531-7 (1992).
Cordeau et al. "Live imaging of neuroinflammation reveals sex and estrogen effects on astrocyte response to ischemic injury", Stroke 39, 935-942 (2008).
Corrado et al. "High frequency of TARDBP gene mutations in Italian patients with amyotrophic lateral sclerosis", Hum Mutat 30, 688-694 (2009).
Custer et al. "Transgenic mice expressing mutant forms VCP/p97 recapitulate the full spectrum of IBMPFD including degeneration in muscle, brain and bone", Hum Mol Genet 19, 1741-1755 (2010).
Daoud et al. "Contribution of TARDBP mutations to sporadic amyotrophic lateral sclerosis", J Med Genet 46, 112-114 (2009).
Davies et al. "Isolation and culture of murine macrophages", Methods Mol Biol 290, 91-103 (2005).

Deng, HX, et al. "FUS-immunoreactive inclusions are a common feature in sporadic and non-SOD1 familial amyotrophic lateral sclerosis", Ann Neurol 67, 739-748 (2010).
Dequen et al. "Modest loss of peripheral axons, muscle atrophy and formation of brain inclusions in mice with targeted deletion of gigaxonin exon 1", J Neurochem 107, 253-264 (2008).
Di Giorgio et al. "Non-cell autonomous effect of glia on motor neurons in an embryonic stem cell-based ALS model", Nat Neurosci 10:608-14 (2007).
Di Giorgio et al. "Human embryonic stem cell-derived motor neurons are sensitive to the toxic effect of glial cells carrying an ALS-causing mutation", Cell Stem Cell 3:637-48 (2008).
Dormann et al. "Proteolytic processing of TAR DNA binding protein-43 by caspases produces C-terminal fragments with disease defining properties independent of progranulin", J Neurochem 110, 1082-1094 (2009).
Douville et al. "Identification of active loci of a human endogenous retrovirus in neurons of patients with amyotrophic lateral sclerosis", Ann Neuro 69, 141-151 (2011).
Dreyfuss et al. "hnRNP proteins and the biogenesis of mRNA", Annu Rev Biochem 62, 289-321 (1993).
Forman et al. "TDP-43: a novel neurodegenerative proteinopathy", Curr Opin Neurobiol 17:548-55 (2007).
Gerritsen et al. "CREB-binding protein/p300 are transcriptional coactivators of p65", Proc Natl Acad Sci USA 94, 2927-2932 (1997).
Gitcho et al. "TDP-43 A315T mutation in familial motor neuron disease" Ann Neurol 63, 535-538 (2008).
Gitcho et al. "TARDBP 3'-UTR variant in autopsy-confirmed frontotemporal lobar degeneration with TDP-43 proteinopathy", Acta Neuropathol 118, 633-645 (2009).
Gros-Louis et al. "Als2 mRNA splicing variants detected in KO mice rescue severe motor dysfunction phenotype in Als2 knock-down zebrafish", Hum Mol Genet 17, 2691-2702 (2008).
Guerreiro et al. "TDP-43 is not a common cause of sporadic amyotrophic lateral sclerosis", PLoS One 3, e2450 (2008).
Hart et al. "The use of animal models to investigate the pathogenesis of neuroinflammatory disorders of the central nervous system", Curr Opin Neurol 16, 375-383 (2003).
Hodges et al. "Clinicopathological correlates in frontotemporal dementia", Ann Neurol 56, 399-406 (2004).
Horvath et al. "Differential migration, LPS-induced cytokine, chemokine, and NO expression in immortalized BV-2 and HAPI cell lines and primary microglial cultures", J Neurochem 107, 557-569 (2008).
Igaz et al. "Expression of TDP-43 C-terminal fragments in vitro recapitulates pathological features of TDP-43 proteinopathies", J Biol Chem 284, 8516-8524 (2009).
Johnson et al. "A yeast TDP-43 proteinopathy model: exploring the molecular determinants of TDP-43 aggregation and cellular toxicity", Proc Natl Acad Sci USA 105, 6439-6444 (2008).
Johnson et al. "Exome sequencing reveals VCP mutations as a cause of familial ALS", Neuron 68, 857-864 (2010).
Julien "ALS: astrocytes move in as deadly neighbors", Nat Neurosci 10, 535-537 (2007).
Kabashi et al. "TARDBP mutations in individuals with sporadic and familial amyotrophic lateral sclerosis", Nat Genet 40, 572-574 (2008).
Kasai et al. "Increased TDP-43 protein in cerebrospinal fluid of patients with amyotrophic lateral sclerosis", Acta Neuropathol 117, 55-62 (2009).
Keller et al. "Empirical statistical model to estimate the accuracy of peptide identifications made by MS/MS and database search", Anal Chem 74, 5383-5392 (2002).
Keller et al. "Live imaging of amyotrophic lateral sclerosis pathogenesis: disease onset is characterized by marked induction of GFAP in Schwann cell", Glia 57, 1130-1142 (2009).
Keller et al. "Treatment with minocycline after disease onset al.ters astrocyte reactivity and increases microgliosis in SOD1 mutant mice", Exp Neurol, 228, 69-79 (2011).
Kriz et al. "Altered ionic conductances in axons of transgenic mouse expressing the human neurofilament heavy gene: A mouse model of amyotrophic lateral sclerosis", Exp Neurol 163, 414-421 (2000).

(56) References Cited

OTHER PUBLICATIONS

Kwiatkowski et al. "Mutations in the FUS/TLS gene on chromosome 16 cause familial amyotrophic lateral sclerosis", Science 323, 1205-1208 (2009).
Lagier-Tourenne et al. "Rethinking ALS: the FUS about TDP-43", Cell 136, 1001-1004 (2009).
Ling et al. "ALS-associated mutations in TDP-43 increase its stability and promote TDP-43 complexes with FUS/TLS", Proc Natl Acad Sci USA 107, 13318-13323 (2010).
Lomen-Hoerth et al. "Are amyotrophic lateral sclerosis patients cognitively normal?", Neurology 60, 1094-1097 (2003).
Lu et al. "A method to solubilise protein aggregates for immunoassay quantification which overcomes the neurofilament "hook" effect", J Neurosci Methods 195, 143-50 (2011).
Maruyama et al. "Mutations of optineurin in amyotrophic lateral sclerosis", Nature 465, 223-226 (2010).
Maysinger et al. "Real-time imaging of astrocyte response to quantum dots: in vivo screening model system for biocompatibility of nanoparticles", Nano Lett 7, 2513-2520 (2007).
Mercado et al. "Depletion of TDP-43 overrides the need for exonic and intronic splicing enhancers in the human apoA-II gene", Nucleic Acids Res 33, 6000-6010 (2005).
Migheli et al. "Peripherin immunoreactive structures in amyotrophic lateral sclerosis", Lab Invest 68, 185-191 (1993).
Nagai et al. "Astrocytes expressing ALS-linked mutated SOD1 release factors selectively toxic to motor neurons", Nat Neurosci 10, 615-622 (2007).
Neumann et al. "Ubiquitinated TDP-43 in frontotemporal lobar degeneration and amyotrophic lateral sclerosis", Science 314, 130-133 (2006).
Neumann et al. "Molecular Neuropathology of TDP-43 Proteinopathies", In J Mol Sci 10, 232-246 (2009).
Noto et al. "Elevated CSF TDP-43 levels in amyotrophic lateral sclerosis: specificity, sensitivity and a possible prognostic value" Amyotroph Lateral Scler 12, 140-143 (2011).
Oh et al. "Withaferin A inhibits iNOS expression and nitric oxide production by Akt inactivation and down-regulating LPS-induced activity of NF-κB in RAW 2647 cells", Eur J Pharmacol 599, 11-17 (2008).
Ou et al. "Cloning and characterization of a novel cellular protein, TDP-43, that binds to human immunodefficiency virus type 1 TAR DNA sequence motifs", J Virol 69, 3584-3596 (1995).
Patel et al. "Adeno-associated Virus-mediated Delivery of a Recombinant Single-chain Antobody Against Misfolded Superoxide Dismutase for Treatment of Amyotrophic Lateral Sclerosis", Mol Ther 22(3), 498-510 (2014).
Perkins et al. "Regulation of NF-κB by cyclin-dependent kinases associated with the p300 coactivator", Science 275, 523-527 (1997).
Pierre Julien et al. "Single chain recombinant antibodies to target TDP-43 interactions" Poster-Sp_Australia: 25th Biennial Meeting of the International Society for Neurochemistry held in Cairns, Australia, Aug. 23-27, 2015.
Pizzi et al. "Inhibition of IκBalpha phosphorylation prevents glutamate-induced NF-κB activation and neuronal cell death", Acta Neurochir Suppl 93, 59-63 (2005).
Pizzi et al. "Distinct roles of diverse nuclear factor-kB complexes in neuropathological mechanisms", European J of Pharmacology 545(1), 22-28 (2006).
Polymenidou et al. "Long pre-mRNA depletion and RNA missplicing contribute to neuronal vulnerability from loss of TDP-43", Nat Neurosci 14, 459-468 (2011).
Pozzi et al. "Single chain antibodies against TDP-43 for treatment of ALS" Poster-ALSMND: 24th International Symposium on ALS/Motor Neuron Disease held in Milan, Italy, Dec. 6-8, 2013.
Prut et al. "Aged APP23 mice show a delay in switching to the use of a strategy in the Barnes maze", Behav Brain Res 179, 107-110 (2007).
Robertson et al. "A neurotoxic peripherin splice variant in a mouse model of ALS", J Cell Biol 160, 939-949 (2003).
Rutherford et al. "Novel mutations in TARDBP (TDP-43) in patients with familial amyotrophic lateral sclerosis", PLoS Genet 4:e1000193 (2008).
Sanelli et al. "Evidence that TDP-43 is not the major ubiquinated target within the pathological inclusions of amyotrophic lateral sclerosis", Journal of neuropathology and experimental neurology 66, 1147-1153 (2007).
Schmitz et al. "Interaction of the COOH-terminal transactivation domain of p65 NF-κB with TATA-binding protein, transcription factor IIb, and coactivators", J Biol Chem 270, 7219-7226 (1995).
Schmitz et al. "Transactivation domain 2 (TA2). of p65 NF-κB Similarity to TA1 and phorbol ester-stimulated activity and phosphorylation in intact cells", J Biol Chem 270, 15576-15584 (1995).
Schwarz et al. "Microglia activation in multiple system atrophy: a potential role for NF-κB/rel proteins", NeuroReport 9(13), 3029-3032 (1998).
Seeley "Selective functional, regional, and neuronal vulnerability in frontotemporal dementia", Curr Opin Neurol 21, 701-707 (2008).
Sephton et al. "TDP-43 is a developmentally regulated protein essential for early embryonic development", J Biol Chem 285, 6826-6834 (2010).
Seyfried et al. "Multiplex SILAC analysis of a cellular TDP-43 proteinopathy model reveals protein inclusions associated with SUMOylation and diverse polyubiquitin chains", Mol Cell Proteomics 9, 705-718 (2010).
Sheppard et al. "Transcriptional activation by NF-κB requires multiple coactivators", Mol Cell Biol 19, 6367-6378 (1999).
Shodai et al. "Aberrant Assembly of RNA Recognition Motif 1 links to Pathogenic Conversion of TAR DNA-binding Protein of 43 kDa (TDP-43)", JBC 288(21), 14886-14905 (2013).
Sreedharan et al. "TDP-43 mutations in familial and sporadic amyotrophic lateral sclerosis", Science 319, 1668-1672 (2008).
Stallings et al. "Generation and characterization of wild-type and mutant TDP-43 transgenic mice", Society for Neuroscience, Abstract Book (2009).
Stallings et al. "Progressive motor weakness in transgenic mice expressing human TDP-43", Neurobiol Dis 40, 404-414 (2010).
Sterneck et al. "Interleukin-6 induces expression of peripherin and cooperates with Trk receptor signaling to promote neuronal differentiation in PC12 cells", J Neurochem 67, 1365-1374 (1996).
Suzuki et al. "Increased expression of TDP-43 in the skin of amyotrophic lateral sclerosis", Acta Neurol Scand 122, 367-372 (2010).
Swarup et al. "Japanese encephalitis virus infection decrease endogenous IL-10 production: correlation with microglial activation and neuronal death", Neurosci Lett 420, 144-149 (2007).
Swarup et al. "Tumor necrosis factor receptor-1-induced neuronal death by TRADD contributes to the pathogenesis of Japanese encephalitis", J Neurochem 103, 771-783 (2007).
Swarup et al. "ALS pathogenesis: Recent insights from genetics and mouse models", Progress in Neuro-Psychopharmacology & Biological Psychiatry 35, 363-369 (2011).
Swarup et al. "Deregulation of TDP-43 in amyotrophic lateral sclerosis triggers nuclear factor kB-mediated pathogenic pathways", J Exp Med 208(12), 2429-2447 (2011).
Swarup et al. "Pathological hallmarks of amyotrophic lateral sclerosis/frontotemporal lobar degeneration in transgenic mice produced with TDP-43 genomic fragments", Brain 134, 2610-2626 (2011).
Talbot et al. "Recent advances in the genetics of amyotrophic lateral sclerosis and frontotemporal dementia: common pathways in neurodegenerative disease", Hum Mol Genet 15(2), R182-R187 (2006).
Thaiparambil et al. "Withaferin A inhibits breast cancer invasion and metastasis at sub-cytotoxic doses by inducing vimentin disassembly and serine 56 phosphorylation", Int J Cancer 129, 2744-2755 (2011).
Van Deerlin et al. "TARDBP mutations in amyotrophic lateral sclerosis with TDP-43 neuropathology: a genetic and histopathological analysis", Lancet Neurol 7, 409-416 (2008).
Vance et al. "Mutations in FUS, an RNA processing protein, cause familial amyotrophic lateral sclerosis type 6", Science 323, 1208-1211 (2009).

(56) References Cited

OTHER PUBLICATIONS

Voigt et al. "TDP-43-mediated neuron loss in vivo requires RNA-binding activity", PLoS One 5, e12247 (2010).
Wegorzewska et al. "TDP-43 mutant transgenic mice develop features of ALS and frontotemporal lobar degeneration", Proc Natl Acad Sci USA 106, 18809-18814 (2009).
Weydt et al. "Increased cytotoxic potential of microglia from ALS-transgenic mice", Glia 48, 179-182 (2004).
Wils et al. "TDP-43 transgenic mice develop spastic paralysis and neuronal inclusions characteristic of ALS and frontotemporal lobar degeneration", Proc Natl Acad Sci USA 107, 3858-3863 (2010).
Wong et al. "Characterization of neuronal intermediate filament protein expression in cervical spinal motor neurons in sporadic amyotrophic lateral sclerosis (ALS).", J Neuropathol Exp Neurol 59, 972-82 (2000).
Xiao et al. "An aggregate-inducing peripherin isoform generated through intron retention is upregulated in amyotrophic lateral sclerosis and associated with disease pathology", J Neurosci 28, 1833-1840 (2008).
Xu et al. "Wild-type human TDP-43 expression causes TDP-43 phosphorylation, mitochondrial aggregation, motor deficits, and early mortality in transgenic mice", J Neurosci 30, 10851-10859 (2010).
Yokoseki et al. "TDP-43 mutation in familial amyotrophic lateral sclerosis", Ann Neurol 63, 538-542 (2008).
Yoza et al. "Protein-tyrosine kinase activation is required for lipopolysaccharide induction of interleukin 1β and NFκB activation, but not NFκB nuclear translocation", J Biol Chem 271, 18306-18309 (1996).
Yum et al. "A novel recessive Nefl mutation causes a severe, early-onset axonal neuropathy", Ann Neurol 66, 759-770 (2009).
Zhang et al. "Aberrant cleavage of TDP-43 enhances aggregation and cellular toxicity", Proc Natl Acad Sci USA 106, 7607-7612 (2009).
Zhang et al. "Circulating endotoxin and systemic immune activation in sporadic amyotrophic lateral sclerosis (sALS).", J Neuroimmunol 206, 121-124 (2009).
Zhang et al. "Gene expression profiling in peripheral blood mononuclear cells from patients with sporadic amyotrophic lateral sclerosis (sALS).", J Neuroimmunol 230, 114-123 (2011).
Gendron et al. (2010) "Review: Transactive Response DNA-Binding Protein 43 (TDP-43): Mechanisms of Neurodegeneration", Neuropathology and Applied Neurobiology, Wiley-Blackwell Publishing Ltd, 36, 97-112.
Kwong et al. (2014) "Novel Monoclonal Antibodies to Normal and Pathologically Altered Human TDP-43 Proteins", ACTA Neuropathologica Communications, Biomed Central Ltd, 2;33, 1-9.

* cited by examiner

Figure 2 ELISA shows that recombinant p65_His Tag (0.2ug/ml) directly interacts with human recombinant TDP-43_GST Tag
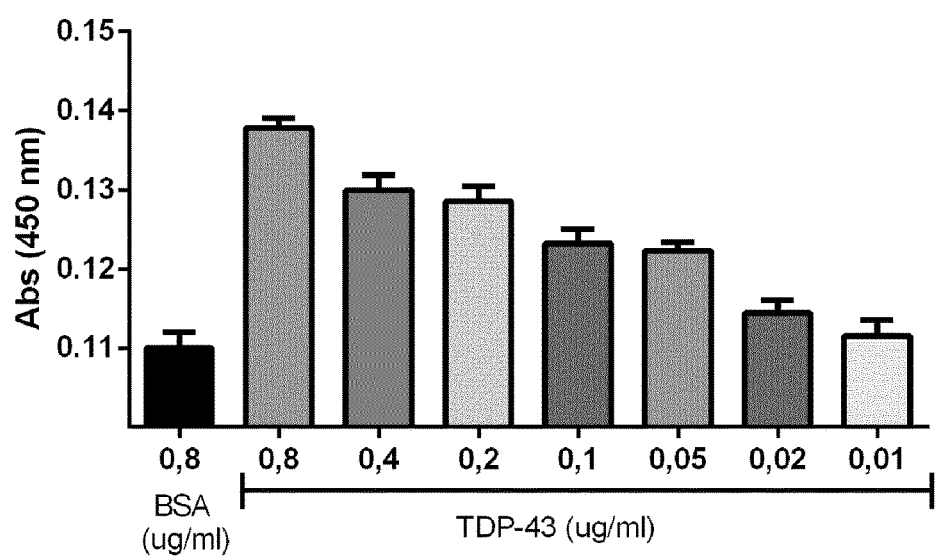

Figure 3 Anti-TDP-43 antibodies (C10, G8 and E6) can block interaction between TDP-43 and p65 NF-kB in ELISA
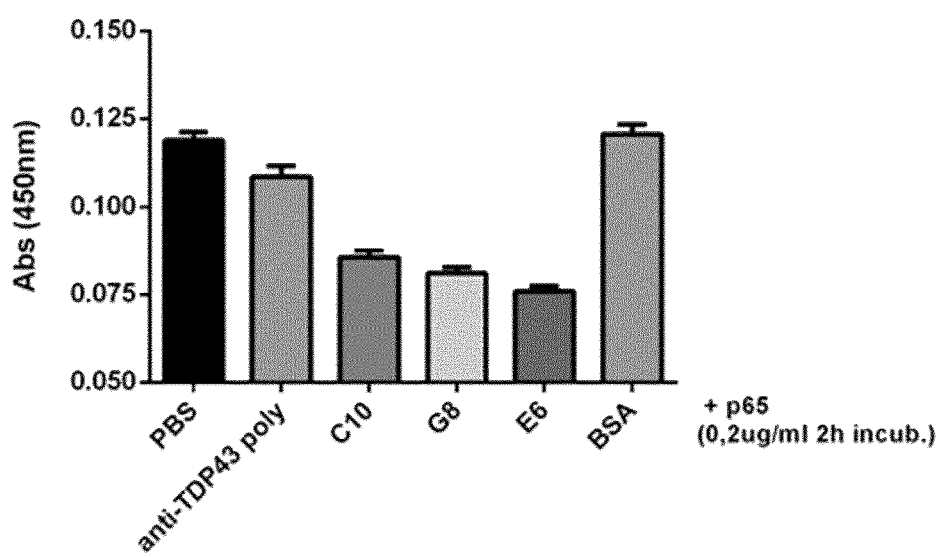

Figure 4A Schematic representation of vectors encoding exemplary anti-TDP-43 scFv antibodies
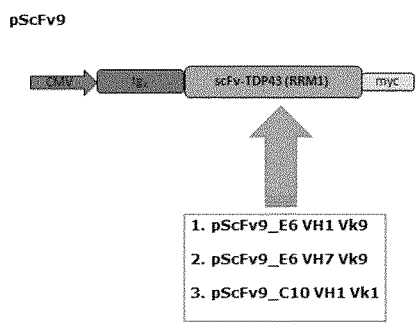
Figure 4B Schematic representation of an exemplary full size anti-TDP-43 antibody, and an exemplary anti-TDP-43 antibody having an scFv format
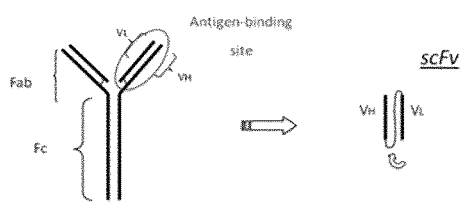

Figure 5 Single chain antibodies derived from anti-TDP antibody E6 clone are produced and secreted by transfected Hek293 cells.
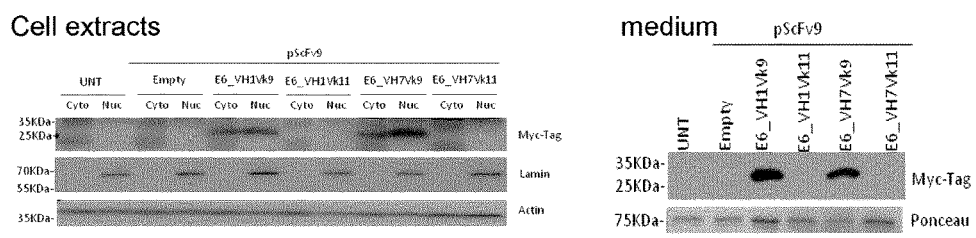

Figure 6 scFv antibodies can detect a TDP-43 fragment applied on a membrane
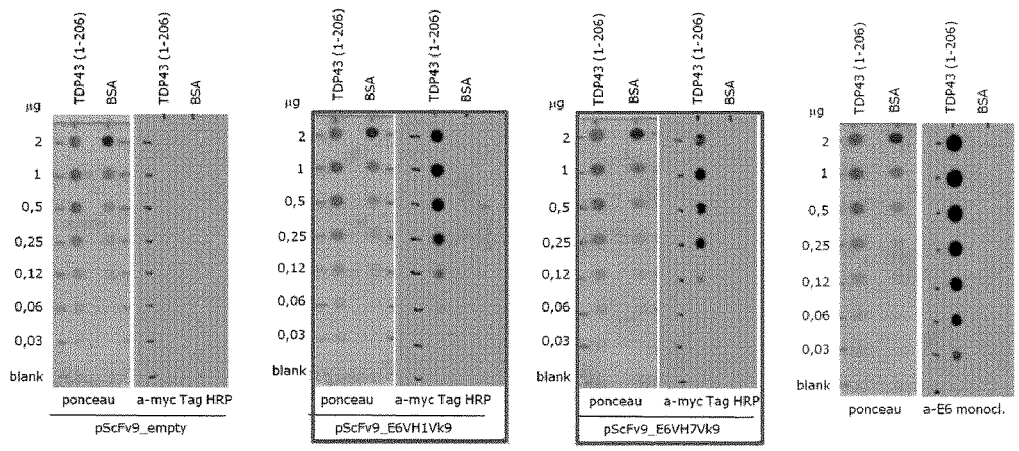

Figure 7 scFv antibodies (E6_VH1Vk9 and E6_VH7Vk9) block interaction between recombinant TDP-43 with p65 NF-kB
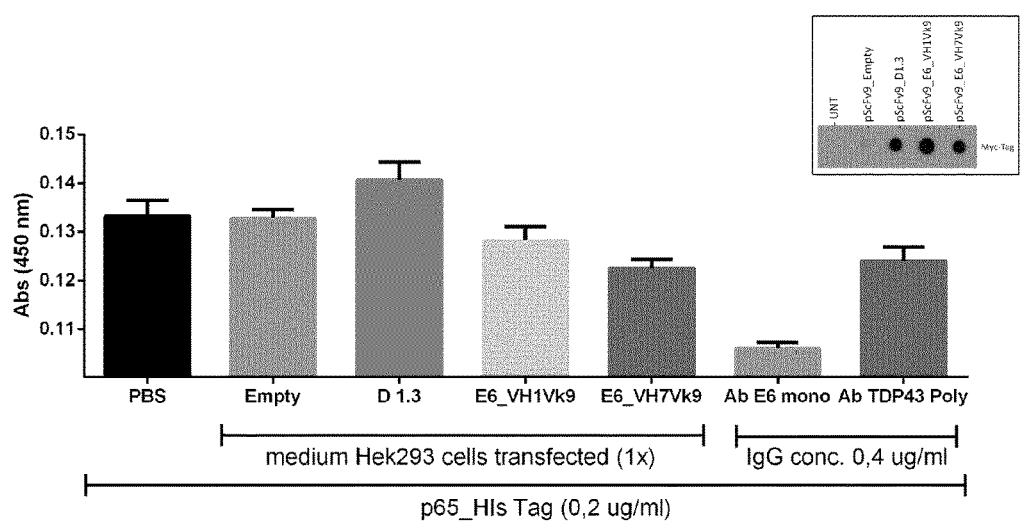

Figure 8 scFv antibodies expressed in Hek293cells interact with TDP-43 as revealed by co-immunoprecipitation with polyclonal antibodies against TDP-43
svFv antibodies are co-immunoprecipitated with TDP-43 →
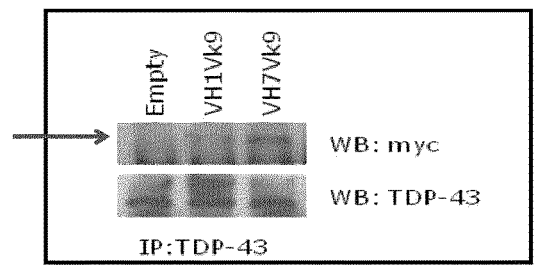

Figure 9 scFv antibody VH1Vk9 can block interaction of TDP-43 with p65 NF-kB when expressed in Hek293 cells
scFv antibodies block interaction of TDP-43 with p65 NF-kB
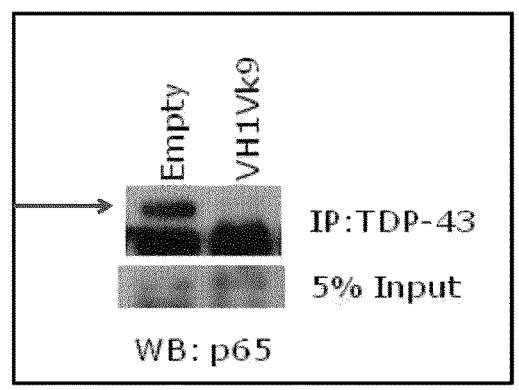

Figure 10 Expression of scFv antibodies in BV2 microglial cells reduced NF-kB activation by LPS treatment as revealed by luciferase assay
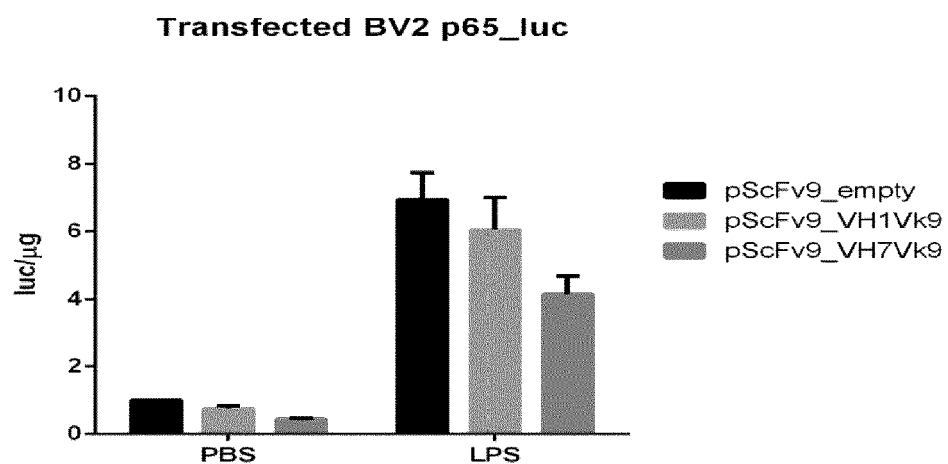

Figure 11 scFv anti-TDP-43 antibodies expressed in Neuro2A cells caused a reduction in levels of nuclear TDP-43
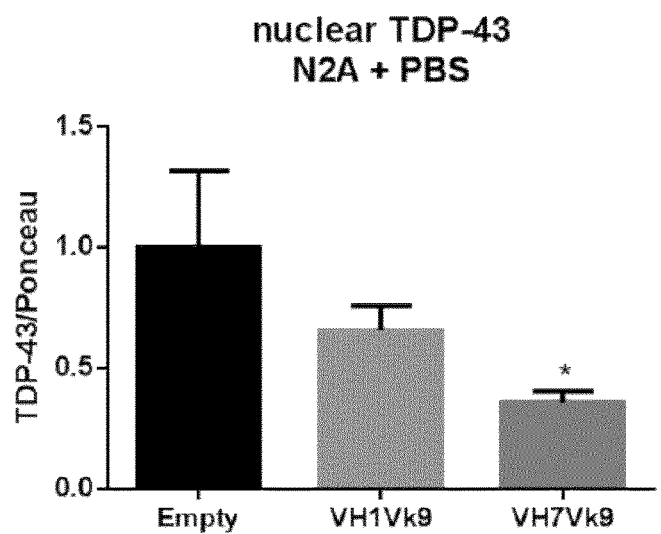

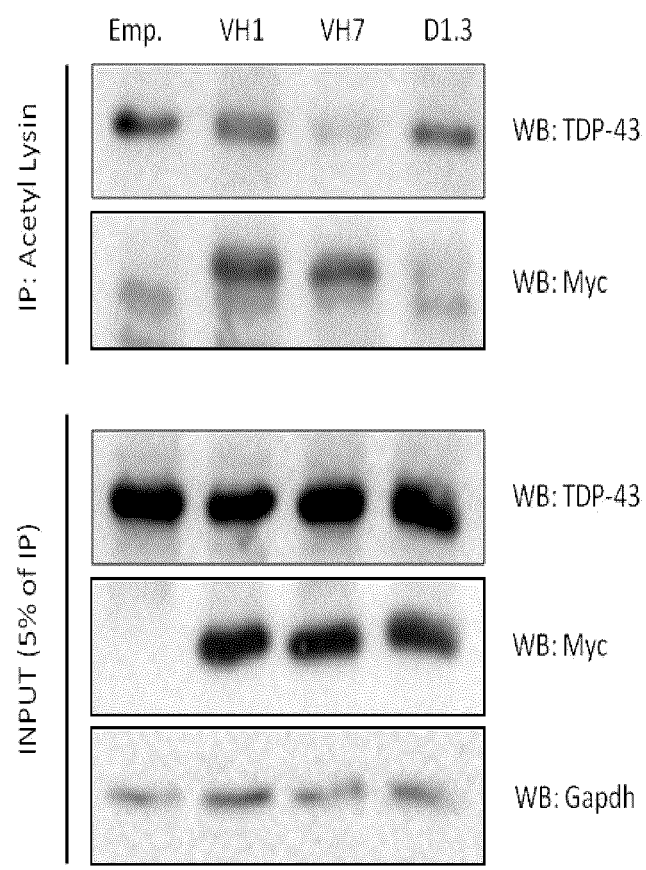
Figure 13 E6 anti-TDP scFv protects TDP-43 from lysine acetylation

```
SEQUENCE LISTING

<160> NUMBER OF SEQ ID NOS: 53

<210> SEQ ID NO 1
<211> LENGTH: 118
<212> TYPE: PRT
<213> ORGANISM: Artificial Sequence
<220> FEATURE:
<223> OTHER INFORMATION: E6_VH1 heavy chain variable region

<400> SEQUENCE: 1

Leu Gln Glu Ser Gly Gly Gly Leu Val Gln Pro Gly Gly Ser Met Lys
1               5                   10                  15

Leu Ser Cys Val Ala Ser Gly Phe Thr Ser Ser Asn Tyr Trp Leu Asn
            20                  25                  30

Trp Val Arg Gln Ser Pro Glu Arg Gly Leu Glu Trp Val Ala Glu Ile
        35                  40                  45

Arg Leu Lys Ser Asn Asn Tyr Ala Thr Asn Tyr Ala Glu Ser Val Lys
    50                  55                  60

Gly Arg Phe Thr Ile Ser Arg Asp Asp Ser Lys Ser Ser Val Tyr Leu
65                  70                  75                  80

Gln Val Asn Asn Leu Arg Ala Glu Asp Thr Gly Ile Tyr Tyr Cys Thr
                85                  90                  95

Arg Ser Thr Ala Arg Ala Thr Pro Tyr Tyr Phe Asp Tyr Trp Gly Gln
            100                 105                 110

Gly Thr Thr Val Thr Val
        115

<210> SEQ ID NO 2
<211> LENGTH: 118
<212> TYPE: PRT
<213> ORGANISM: Artificial Sequence
<220> FEATURE:
<223> OTHER INFORMATION: E6_VH7 heavy chain variable region

<400> SEQUENCE: 2

Leu Gln Gln Ser Gly Gly Gly Leu Val Gln Pro Gly Gly Ser Met Lys
1               5                   10                  15

Leu Ser Cys Val Ala Ser Gly Phe Thr Ser Ser Asn Tyr Trp Leu Asn
            20                  25                  30

Trp Val Arg Gln Ser Pro Glu Arg Gly Leu Glu Trp Val Ala Glu Ile
        35                  40                  45

Arg Leu Lys Ser Asn Asn Tyr Ala Thr Asn Tyr Ala Glu Ser Val Lys
    50                  55                  60

Gly Arg Phe Thr Ile Ser Arg Asp Asp Ser Lys Ser Ser Val Tyr Leu
```

```
                65                  70                  75                  80
Gln Val Asn Asn Leu Arg Ala Glu Asp Thr Gly Ile Tyr Tyr Cys Thr
                    85                  90                  95

Arg Ser Thr Ala Arg Ala Thr Pro Tyr Tyr Phe Asp Tyr Trp Gly Gln
                100                 105                 110

Gly Thr Thr Val Thr Val
        115

<210> SEQ ID NO 3
<211> LENGTH: 108
<212> TYPE: PRT
<213> ORGANISM: Artificial Sequence
<220> FEATURE:
<223> OTHER INFORMATION: E6_Vk9 light chain variable region

<400> SEQUENCE: 3

Glu Leu Thr Gln Ser Pro Ser Ser Leu Ala Val Ser Ala Gly Glu Lys
1               5                   10                  15

Val Thr Met Ser Cys Lys Ser Ser Gln Ser Leu Leu Asn Ser Arg Ala
                20                  25                  30

Arg Lys Asn Phe Leu Thr Trp Tyr Gln Gln Lys Pro Gly Gln Ser Pro
            35                  40                  45

Lys Leu Leu Ile Tyr Trp Ala Ser Thr Arg Glu Ser Gly Val Pro Asp
    50                  55                  60

Arg Phe Thr Gly Ser Gly Ser Gly Thr Asp Phe Thr Leu Thr Ile Ser
65                  70                  75                  80

Ser Val Gln Ala Glu Asp Leu Ala Val Tyr Tyr Cys Lys Gln Ser Tyr
                85                  90                  95

Asn Leu Tyr Thr Phe Gly Gly Gly Thr Lys Leu Glu
                100                 105

<210> SEQ ID NO 4
<211> LENGTH: 97
<212> TYPE: PRT
<213> ORGANISM: Artificial Sequence
<220> FEATURE:
<223> OTHER INFORMATION: C10_VH3 heavy chain variable region

<400> SEQUENCE: 4

Leu Gln Glu Ser Gly Gly Gly Leu Val Gln Pro Gly Gly Ser Arg Lys
1               5                   10                  15

Leu Ser Cys Ala Ala Ser Gly Phe Thr Phe Ser Ser Phe Gly Met His
                20                  25                  30

Trp Val Arg Gln Ala Pro Glu Lys Gly Leu Glu Trp Val Ala Tyr Ile
            35                  40                  45

Ser Ser Gly Ser Ser Thr Leu His Tyr Ala Asp Thr Val Lys Gly Arg
    50                  55                  60

Phe Thr Ile Ser Arg Asp Asn Pro Lys Asn Thr Leu Phe Leu Gln Met
65                  70                  75                  80

Lys Leu Pro Ser Leu Cys Tyr Gly Leu Leu Gly Pro Arg Asp His Gly
                85                  90                  95

His

<210> SEQ ID NO 5
<211> LENGTH: 97
<212> TYPE: PRT
<213> ORGANISM: Artificial Sequence
<220> FEATURE:
<223> OTHER INFORMATION: C10_VH4 heavy chain variable region
```

<400> SEQUENCE: 5

```
Leu Gln Gln Ser Gly Gly Gly Leu Val Gln Pro Gly Gly Ser Arg Lys
1               5                   10                  15

Leu Ser Cys Ala Ala Ser Gly Phe Thr Phe Ser Ser Phe Gly Met His
            20                  25                  30

Trp Val Arg Gln Ala Pro Glu Lys Gly Leu Glu Trp Val Ala Tyr Ile
        35                  40                  45

Ser Ser Gly Ser Ser Thr Leu His Tyr Ala Asp Thr Val Lys Gly Arg
    50                  55                  60

Phe Thr Ile Ser Arg Asp Asn Pro Lys Asn Thr Leu Phe Leu Gln Met
65                  70                  75                  80

Lys Leu Pro Ser Leu Cys Tyr Gly Leu Leu Gly Pro Arg Asp His Gly
                85                  90                  95

His
```

<210> SEQ ID NO 6
<211> LENGTH: 105
<212> TYPE: PRT
<213> ORGANISM: Artificial Sequence
<220> FEATURE:
<223> OTHER INFORMATION: C10_Vk3 light chain variable region

<400> SEQUENCE: 6

```
Glu Leu Thr Gln Ser Pro Ala Ser Leu Ala Val Ser Leu Gly Gln Arg
1               5                   10                  15

Ala Thr Ile Ser Tyr Arg Ala Ser Lys Ser Val Ser Thr Ser Gly Tyr
            20                  25                  30

Ser Tyr Met His Trp Asn Gln Gln Lys Pro Gly Gln Pro Pro Arg Leu
        35                  40                  45

Leu Ile Tyr Leu Val Ser Asn Leu Glu Ser Gly Val Pro Ala Arg Phe
    50                  55                  60

Ser Gly Ser Gly Ser Gly Thr Asp Phe Thr Leu Asn Ile His Pro Val
65                  70                  75                  80

Glu Glu Glu Asp Ala Ala Thr Tyr Tyr Cys Gln His Ile Arg Glu Leu
                85                  90                  95

Thr Arg Ser Glu Gly Ala Pro Ser Ser
            100                 105
```

<210> SEQ ID NO 7
<211> LENGTH: 8
<212> TYPE: PRT
<213> ORGANISM: Artificial Sequence
<220> FEATURE:
<223> OTHER INFORMATION: E6_VH1 CDR1

<400> SEQUENCE: 7

```
Ser Ser Asn Tyr Trp Leu Asn Trp
1               5
```

<210> SEQ ID NO 8
<211> LENGTH: 15
<212> TYPE: PRT
<213> ORGANISM: Artificial Sequence
<220> FEATURE:
<223> OTHER INFORMATION: E6_VH1 CDR2

<400> SEQUENCE: 8

```
Glu Ile Arg Leu Lys Ser Asn Asn Tyr Ala Thr Asn Tyr Ala Glu
1               5                   10                  15
```

<210> SEQ ID NO 9
<211> LENGTH: 9
<212> TYPE: PRT
<213> ORGANISM: Artificial Sequence
<220> FEATURE:
<223> OTHER INFORMATION: E6_VH1 CDR3

<400> SEQUENCE: 9

Arg Ala Thr Pro Tyr Tyr Phe Asp Tyr
1               5

<210> SEQ ID NO 10
<211> LENGTH: 8
<212> TYPE: PRT
<213> ORGANISM: Artificial Sequence
<220> FEATURE:
<223> OTHER INFORMATION: E6_VH7 CDR1

<400> SEQUENCE: 10

Ser Ser Asn Tyr Trp Leu Asn Trp
1               5

<210> SEQ ID NO 11
<211> LENGTH: 15
<212> TYPE: PRT
<213> ORGANISM: Artificial Sequence
<220> FEATURE:
<223> OTHER INFORMATION: E6_VH7 CDR2

<400> SEQUENCE: 11

Glu Ile Arg Leu Lys Ser Asn Asn Tyr Ala Thr Asn Tyr Ala Glu
1               5                   10                  15

<210> SEQ ID NO 12
<211> LENGTH: 9
<212> TYPE: PRT
<213> ORGANISM: Artificial Sequence
<220> FEATURE:
<223> OTHER INFORMATION: E6_VH7 CDR3

<400> SEQUENCE: 12

Arg Ala Thr Pro Tyr Tyr Phe Asp Tyr
1               5

<210> SEQ ID NO 13
<211> LENGTH: 17
<212> TYPE: PRT
<213> ORGANISM: Artificial Sequence
<220> FEATURE:
<223> OTHER INFORMATION: E6_Vk9 CDR1

<400> SEQUENCE: 13

Lys Ser Ser Gln Ser Leu Leu Asn Ser Arg Ala Arg Lys Asn Phe Leu
1               5                   10                  15

Thr

<210> SEQ ID NO 14
<211> LENGTH: 8
<212> TYPE: PRT
<213> ORGANISM: Artificial Sequence
<220> FEATURE:
<223> OTHER INFORMATION: E6_Vk9 CDR2

<400> SEQUENCE: 14

Tyr Trp Ala Ser Thr Arg Glu Ser

```
<210> SEQ ID NO 15
<211> LENGTH: 8
<212> TYPE: PRT
<213> ORGANISM: Artificial Sequence
<220> FEATURE:
<223> OTHER INFORMATION: E6_Vk9 CDR3

<400> SEQUENCE: 15

Lys Gln Ser Tyr Asn Leu Tyr Thr
1               5

<210> SEQ ID NO 16
<211> LENGTH: 7
<212> TYPE: PRT
<213> ORGANISM: Artificial Sequence
<220> FEATURE:
<223> OTHER INFORMATION: C10_VH3 CDR1

<400> SEQUENCE: 16

Ser Ser Phe Gly Met His Trp
1               5

<210> SEQ ID NO 17
<211> LENGTH: 13
<212> TYPE: PRT
<213> ORGANISM: Artificial Sequence
<220> FEATURE:
<223> OTHER INFORMATION: C10_VH3 CDR2

<400> SEQUENCE: 17

Tyr Ile Ser Ser Gly Ser Ser Thr Leu His Tyr Ala Asp
1               5                   10

<210> SEQ ID NO 18
<211> LENGTH: 9
<212> TYPE: PRT
<213> ORGANISM: Artificial Sequence
<220> FEATURE:
<223> OTHER INFORMATION: C10_VH3 CDR3

<400> SEQUENCE: 18

Phe Leu Gln Met Lys Leu Pro Ser Leu
1               5

<210> SEQ ID NO 19
<211> LENGTH: 7
<212> TYPE: PRT
<213> ORGANISM: Artificial Sequence
<220> FEATURE:
<223> OTHER INFORMATION: C10_VH4 CDR1

<400> SEQUENCE: 19

Ser Ser Phe Gly Met His Trp
1               5

<210> SEQ ID NO 20
<211> LENGTH: 13
<212> TYPE: PRT
<213> ORGANISM: Artificial Sequence
<220> FEATURE:
<223> OTHER INFORMATION: C10_VH4 CDR2

<400> SEQUENCE: 20

Tyr Ile Ser Ser Gly Ser Ser Thr Leu His Tyr Ala Asp
1               5                   10
```

<210> SEQ ID NO 21
<211> LENGTH: 9
<212> TYPE: PRT
<213> ORGANISM: Artificial Sequence
<220> FEATURE:
<223> OTHER INFORMATION: C10_VH4 CDR3

<400> SEQUENCE: 21

Phe Leu Gln Met Lys Leu Pro Ser Leu
1               5

<210> SEQ ID NO 22
<211> LENGTH: 15
<212> TYPE: PRT
<213> ORGANISM: Artificial Sequence
<220> FEATURE:
<223> OTHER INFORMATION: C10_Vk3 CDR1

<400> SEQUENCE: 22

Arg Ala Ser Lys Ser Val Ser Thr Ser Gly Tyr Ser Tyr Met His
1               5                   10                  15

<210> SEQ ID NO 23
<211> LENGTH: 8
<212> TYPE: PRT
<213> ORGANISM: Artificial Sequence
<220> FEATURE:
<223> OTHER INFORMATION: C10_Vk3 CDR2

<400> SEQUENCE: 23

Tyr Leu Val Ser Asn Leu Glu Ser
1               5

<210> SEQ ID NO 24
<211> LENGTH: 8
<212> TYPE: PRT
<213> ORGANISM: Artificial Sequence
<220> FEATURE:
<223> OTHER INFORMATION: C10_Vk3 CDR3

<400> SEQUENCE: 24

Gln His Ile Arg Glu Leu Thr Arg
1               5

<210> SEQ ID NO 25
<211> LENGTH: 276
<212> TYPE: PRT
<213> ORGANISM: Artificial Sequence
<220> FEATURE:
<223> OTHER INFORMATION: E6_VH1 Vk9 complete with IGk secretory signal
      and c-myc peptide

<400> SEQUENCE: 25

Met Gly Asp Asn Asp Ile His Phe Ala Phe Leu Ser Thr Gly Val His
1               5                   10                  15

Ser Gln Val Gln Leu Gln Glu Ser Gly Gly Gly Leu Val Gln Pro Gly
                20                  25                  30

Gly Ser Met Lys Leu Ser Cys Val Ala Ser Gly Phe Thr Ser Ser Asn
            35                  40                  45

Tyr Trp Leu Asn Trp Val Arg Gln Ser Pro Glu Arg Gly Leu Glu Trp
        50                  55                  60

Val Ala Glu Ile Arg Leu Lys Ser Asn Asn Tyr Ala Thr Asn Tyr Ala
65                  70                  75                  80

Glu Ser Val Lys Gly Arg Phe Thr Ile Ser Arg Asp Asp Ser Lys Ser
                85                  90                  95

Ser Val Tyr Leu Gln Val Asn Asn Leu Arg Ala Glu Asp Thr Gly Ile
            100                 105                 110

Tyr Tyr Cys Thr Arg Ser Thr Ala Arg Ala Thr Pro Tyr Tyr Phe Asp
            115                 120                 125

Tyr Trp Gly Gln Gly Thr Thr Val Thr Val Ser Ser Gly Gly Gly Gly
            130                 135                 140

Ser Gly Gly Gly Gly Ser Gly Gly Gly Ser Asp Ile Glu Leu Thr
145                 150                 155                 160

Gln Ser Pro Ser Ser Leu Ala Val Ser Ala Gly Glu Lys Val Thr Met
                165                 170                 175

Ser Cys Lys Ser Ser Gln Ser Leu Leu Asn Ser Arg Ala Arg Lys Asn
            180                 185                 190

Phe Leu Thr Trp Tyr Gln Gln Lys Pro Gly Gln Ser Pro Lys Leu Leu
            195                 200                 205

Ile Tyr Trp Ala Ser Thr Arg Glu Ser Gly Val Pro Asp Arg Phe Thr
            210                 215                 220

Gly Ser Gly Ser Gly Thr Asp Phe Thr Leu Thr Ile Ser Ser Val Gln
225                 230                 235                 240

Ala Glu Asp Leu Ala Val Tyr Tyr Cys Lys Gln Ser Tyr Asn Leu Tyr
                245                 250                 255

Thr Phe Gly Gly Gly Thr Lys Leu Glu Glu Gln Lys Leu Ile Ser Glu
            260                 265                 270

Glu Asp Leu Asn
        275

<210> SEQ ID NO 26
<211> LENGTH: 245
<212> TYPE: PRT
<213> ORGANISM: Artificial Sequence
<220> FEATURE:
<223> OTHER INFORMATION: E6_VH1 Vk9 full

<400> SEQUENCE: 26

Leu Gln Glu Ser Gly Gly Gly Leu Val Gln Pro Gly Gly Ser Met Lys
1               5                   10                  15

Leu Ser Cys Val Ala Ser Gly Phe Thr Ser Ser Asn Tyr Trp Leu Asn
            20                  25                  30

Trp Val Arg Gln Ser Pro Glu Arg Gly Leu Glu Trp Val Ala Glu Ile
            35                  40                  45

Arg Leu Lys Ser Asn Asn Tyr Ala Thr Asn Tyr Ala Glu Ser Val Lys
        50                  55                  60

Gly Arg Phe Thr Ile Ser Arg Asp Asp Ser Lys Ser Ser Val Tyr Leu
65                  70                  75                  80

Gln Val Asn Asn Leu Arg Ala Glu Asp Thr Gly Ile Tyr Tyr Cys Thr
                85                  90                  95

Arg Ser Thr Ala Arg Ala Thr Pro Tyr Tyr Phe Asp Tyr Trp Gly Gln
            100                 105                 110

Gly Thr Thr Val Thr Val Ser Ser Gly Gly Gly Gly Ser Gly Gly Gly
            115                 120                 125

Gly Ser Gly Gly Gly Gly Ser Asp Ile Glu Leu Thr Gln Ser Pro Ser
            130                 135                 140

Ser Leu Ala Val Ser Ala Gly Glu Lys Val Thr Met Ser Cys Lys Ser
145                 150                 155                 160

```
Ser Gln Ser Leu Leu Asn Ser Arg Ala Arg Lys Asn Phe Leu Thr Trp
                165                 170                 175

Tyr Gln Gln Lys Pro Gly Gln Ser Pro Lys Leu Leu Ile Tyr Trp Ala
            180                 185                 190

Ser Thr Arg Glu Ser Gly Val Pro Asp Arg Phe Thr Gly Ser Gly Ser
        195                 200                 205

Gly Thr Asp Phe Thr Leu Thr Ile Ser Ser Val Gln Ala Glu Asp Leu
    210                 215                 220

Ala Val Tyr Tyr Cys Lys Gln Ser Tyr Asn Leu Tyr Thr Phe Gly Gly
225                 230                 235                 240

Gly Thr Lys Leu Glu
            245

<210> SEQ ID NO 27
<211> LENGTH: 276
<212> TYPE: PRT
<213> ORGANISM: Artificial Sequence
<220> FEATURE:
<223> OTHER INFORMATION: E6_VH7 Vk9 complete with IGk secretory signal
      and c-myc peptide

<400> SEQUENCE: 27

Met Gly Asp Asn Asp Ile His Phe Ala Phe Leu Ser Thr Gly Val His
1               5                   10                  15

Ser Gln Val Gln Leu Gln Gln Ser Gly Gly Gly Leu Val Gln Pro Gly
            20                  25                  30

Gly Ser Met Lys Leu Ser Cys Val Ala Ser Gly Phe Thr Ser Ser Asn
        35                  40                  45

Tyr Trp Leu Asn Trp Val Arg Gln Ser Pro Glu Arg Gly Leu Glu Trp
    50                  55                  60

Val Ala Glu Ile Arg Leu Lys Ser Asn Asn Tyr Ala Thr Asn Tyr Ala
65                  70                  75                  80

Glu Ser Val Lys Gly Arg Phe Thr Ile Ser Arg Asp Asp Ser Lys Ser
                85                  90                  95

Ser Val Tyr Leu Gln Val Asn Asn Leu Arg Ala Glu Asp Thr Gly Ile
            100                 105                 110

Tyr Tyr Cys Thr Arg Ser Thr Ala Arg Ala Thr Pro Tyr Tyr Phe Asp
        115                 120                 125

Tyr Trp Gly Gln Gly Thr Thr Val Thr Val Ser Ser Gly Gly Gly Gly
    130                 135                 140

Ser Gly Gly Gly Gly Ser Gly Gly Gly Gly Ser Asp Ile Glu Leu Thr
145                 150                 155                 160

Gln Ser Pro Ser Ser Leu Ala Val Ser Ala Gly Glu Lys Val Thr Met
                165                 170                 175

Ser Cys Lys Ser Ser Gln Ser Leu Leu Asn Ser Arg Ala Arg Lys Asn
            180                 185                 190

Phe Leu Thr Trp Tyr Gln Gln Lys Pro Gly Gln Ser Pro Lys Leu Leu
        195                 200                 205

Ile Tyr Trp Ala Ser Thr Arg Glu Ser Gly Val Pro Asp Arg Phe Thr
    210                 215                 220

Gly Ser Gly Ser Gly Thr Asp Phe Thr Leu Thr Ile Ser Ser Val Gln
225                 230                 235                 240

Ala Glu Asp Leu Ala Val Tyr Tyr Cys Lys Gln Ser Tyr Asn Leu Tyr
                245                 250                 255

Thr Phe Gly Gly Gly Thr Lys Leu Glu Glu Gln Lys Leu Ile Ser Glu
            260                 265                 270
```

```
Glu Asp Leu Asn
        275

<210> SEQ ID NO 28
<211> LENGTH: 245
<212> TYPE: PRT
<213> ORGANISM: Artificial Sequence
<220> FEATURE:
<223> OTHER INFORMATION: E6_VH7 Vk9 full

<400> SEQUENCE: 28

Leu Gln Gln Ser Gly Gly Leu Val Gln Pro Gly Gly Ser Met Lys
1               5                   10                  15

Leu Ser Cys Val Ala Ser Gly Phe Thr Ser Ser Asn Tyr Trp Leu Asn
                20                  25                  30

Trp Val Arg Gln Ser Pro Glu Arg Gly Leu Glu Trp Val Ala Glu Ile
                35                  40                  45

Arg Leu Lys Ser Asn Asn Tyr Ala Thr Asn Tyr Ala Glu Ser Val Lys
    50                  55                  60

Gly Arg Phe Thr Ile Ser Arg Asp Asp Ser Lys Ser Ser Val Tyr Leu
65                  70                  75                  80

Gln Val Asn Asn Leu Arg Ala Glu Asp Thr Gly Ile Tyr Tyr Cys Thr
                85                  90                  95

Arg Ser Thr Ala Arg Ala Thr Pro Tyr Tyr Phe Asp Tyr Trp Gly Gln
                100                 105                 110

Gly Thr Thr Val Thr Val Ser Ser Gly Gly Gly Gly Ser Gly Gly Gly
                115                 120                 125

Gly Ser Gly Gly Gly Gly Ser Asp Ile Glu Leu Thr Gln Ser Pro Ser
    130                 135                 140

Ser Leu Ala Val Ser Ala Gly Glu Lys Val Thr Met Ser Cys Lys Ser
145                 150                 155                 160

Ser Gln Ser Leu Leu Asn Ser Arg Ala Arg Lys Asn Phe Leu Thr Trp
                165                 170                 175

Tyr Gln Gln Lys Pro Gly Gln Ser Pro Lys Leu Leu Ile Tyr Trp Ala
                180                 185                 190

Ser Thr Arg Glu Ser Gly Val Pro Asp Arg Phe Thr Gly Ser Gly Ser
                195                 200                 205

Gly Thr Asp Phe Thr Leu Thr Ile Ser Ser Val Gln Ala Glu Asp Leu
    210                 215                 220

Ala Val Tyr Tyr Cys Lys Gln Ser Tyr Asn Leu Tyr Thr Phe Gly Gly
225                 230                 235                 240

Gly Thr Lys Leu Glu
                245

<210> SEQ ID NO 29
<211> LENGTH: 250
<212> TYPE: PRT
<213> ORGANISM: Artificial Sequence
<220> FEATURE:
<223> OTHER INFORMATION: C10_VH3 Vk3 complete with IGk secretory signal
      and c-myc peptide

<400> SEQUENCE: 29

Met Gly Asp Asn Asp Ile His Phe Ala Phe Leu Ser Thr Gly Val His
1               5                   10                  15

Ser Gln Val Gln Leu Gln Glu Ser Gly Gly Gly Leu Val Gln Pro Gly
                20                  25                  30
```

Gly Ser Arg Lys Leu Ser Cys Ala Ala Ser Gly Phe Thr Phe Ser Ser
            35                  40                  45

Phe Gly Met His Trp Val Arg Gln Ala Pro Glu Lys Gly Leu Glu Trp
 50                  55                  60

Val Ala Tyr Ile Ser Ser Gly Ser Ser Thr Leu His Tyr Ala Asp Thr
 65                  70                  75                  80

Val Lys Gly Arg Phe Thr Ile Ser Arg Asp Asn Pro Lys Asn Thr Leu
                 85                  90                  95

Phe Leu Gln Met Lys Leu Pro Ser Leu Cys Tyr Gly Leu Leu Gly Pro
            100                 105                 110

Arg Asp His Gly His Ser Ser Gly Gly Gly Ser Gly Gly Gly Gly
            115                 120                 125

Ser Gly Gly Gly Ser Glu Leu Thr Gln Ser Pro Ala Ser Leu Ala
130                 135                 140

Val Ser Leu Gly Gln Arg Ala Thr Ile Ser Tyr Arg Ala Ser Lys Ser
145                 150                 155                 160

Val Ser Thr Ser Gly Tyr Ser Tyr Met His Trp Asn Gln Gln Lys Pro
                165                 170                 175

Gly Gln Pro Pro Arg Leu Leu Ile Tyr Leu Val Ser Asn Leu Glu Ser
            180                 185                 190

Gly Val Pro Ala Arg Phe Ser Gly Ser Gly Ser Gly Thr Asp Phe Thr
            195                 200                 205

Leu Asn Ile His Pro Val Glu Glu Asp Ala Ala Thr Tyr Tyr Cys
            210                 215                 220

Gln His Ile Arg Glu Leu Thr Arg Ser Glu Gly Ala Pro Ser Ser Glu
225                 230                 235                 240

Gln Lys Leu Ile Ser Glu Glu Asp Leu Asn
            245                 250

<210> SEQ ID NO 30
<211> LENGTH: 219
<212> TYPE: PRT
<213> ORGANISM: Artificial Sequence
<220> FEATURE:
<223> OTHER INFORMATION: C10_VH3 Vk3 full

<400> SEQUENCE: 30

Leu Gln Glu Ser Gly Gly Gly Leu Val Gln Pro Gly Gly Ser Arg Lys
 1               5                  10                  15

Leu Ser Cys Ala Ala Ser Gly Phe Thr Phe Ser Ser Phe Gly Met His
             20                  25                  30

Trp Val Arg Gln Ala Pro Glu Lys Gly Leu Glu Trp Val Ala Tyr Ile
             35                  40                  45

Ser Ser Gly Ser Ser Thr Leu His Tyr Ala Asp Thr Val Lys Gly Arg
 50                  55                  60

Phe Thr Ile Ser Arg Asp Asn Pro Lys Asn Thr Leu Phe Leu Gln Met
 65                  70                  75                  80

Lys Leu Pro Ser Leu Cys Tyr Gly Leu Leu Gly Pro Arg Asp His Gly
                 85                  90                  95

His Ser Ser Gly Gly Gly Ser Gly Gly Gly Gly Ser Gly Gly Gly
            100                 105                 110

Gly Ser Glu Leu Thr Gln Ser Pro Ala Ser Leu Ala Val Ser Leu Gly
            115                 120                 125

Gln Arg Ala Thr Ile Ser Tyr Arg Ala Ser Lys Ser Val Ser Thr Ser
            130                 135                 140

```
Gly Tyr Ser Tyr Met His Trp Asn Gln Gln Lys Pro Gly Gln Pro Pro
145                 150                 155                 160

Arg Leu Leu Ile Tyr Leu Val Ser Asn Leu Glu Ser Gly Val Pro Ala
                165                 170                 175

Arg Phe Ser Gly Ser Gly Ser Gly Thr Asp Phe Thr Leu Asn Ile His
            180                 185                 190

Pro Val Glu Glu Asp Ala Ala Thr Tyr Tyr Cys Gln His Ile Arg
        195                 200                 205

Glu Leu Thr Arg Ser Glu Gly Ala Pro Ser Ser
    210                 215

<210> SEQ ID NO 31
<211> LENGTH: 250
<212> TYPE: PRT
<213> ORGANISM: Artificial Sequence
<220> FEATURE:
<223> OTHER INFORMATION: C10_VH4 Vk3 complete with IGk secretory signal
      and c-myc peptide

<400> SEQUENCE: 31

Met Gly Asp Asn Asp Ile His Phe Ala Phe Leu Ser Thr Gly Val His
1               5                   10                  15

Ser Gln Val Gln Leu Gln Gln Ser Gly Gly Leu Val Gln Pro Gly
            20                  25                  30

Gly Ser Arg Lys Leu Ser Cys Ala Ala Ser Gly Phe Thr Phe Ser Ser
            35                  40                  45

Phe Gly Met His Trp Val Arg Gln Ala Pro Glu Lys Gly Leu Glu Trp
    50                  55                  60

Val Ala Tyr Ile Ser Ser Gly Ser Ser Thr Leu His Tyr Ala Asp Thr
65                  70                  75                  80

Val Lys Gly Arg Phe Thr Ile Ser Arg Asp Asn Pro Lys Asn Thr Leu
                85                  90                  95

Phe Leu Gln Met Lys Leu Pro Ser Leu Cys Tyr Gly Leu Leu Gly Pro
            100                 105                 110

Arg Asp His Gly His Ser Ser Gly Gly Gly Ser Gly Gly Gly Gly
            115                 120                 125

Ser Gly Gly Gly Gly Ser Glu Leu Thr Gln Ser Pro Ala Ser Leu Ala
130                 135                 140

Val Ser Leu Gly Gln Arg Ala Thr Ile Ser Tyr Arg Ala Ser Lys Ser
145                 150                 155                 160

Val Ser Thr Ser Gly Tyr Ser Tyr Met His Trp Asn Gln Gln Lys Pro
                165                 170                 175

Gly Gln Pro Pro Arg Leu Leu Ile Tyr Leu Val Ser Asn Leu Glu Ser
            180                 185                 190

Gly Val Pro Ala Arg Phe Ser Gly Ser Gly Ser Gly Thr Asp Phe Thr
        195                 200                 205

Leu Asn Ile His Pro Val Glu Glu Asp Ala Ala Thr Tyr Tyr Cys
    210                 215                 220

Gln His Ile Arg Glu Leu Thr Arg Ser Glu Gly Ala Pro Ser Ser Glu
225                 230                 235                 240

Gln Lys Leu Ile Ser Glu Glu Asp Leu Asn
                245                 250

<210> SEQ ID NO 32
<211> LENGTH: 219
<212> TYPE: PRT
<213> ORGANISM: Artificial Sequence
```

<220> FEATURE:
<223> OTHER INFORMATION: C10_VH4 Vk3 full

<400> SEQUENCE: 32

Leu Gln Gln Ser Gly Gly Gly Leu Val Gln Pro Gly Gly Ser Arg Lys
1               5                   10                  15

Leu Ser Cys Ala Ala Ser Gly Phe Thr Phe Ser Phe Gly Met His
            20                  25                  30

Trp Val Arg Gln Ala Pro Glu Lys Gly Leu Glu Trp Val Ala Tyr Ile
        35                  40                  45

Ser Ser Gly Ser Ser Thr Leu His Tyr Ala Asp Thr Val Lys Gly Arg
    50                  55                  60

Phe Thr Ile Ser Arg Asp Asn Pro Lys Asn Thr Leu Phe Leu Gln Met
65                  70                  75                  80

Lys Leu Pro Ser Leu Cys Tyr Gly Leu Leu Gly Pro Arg Asp His Gly
                85                  90                  95

His Ser Ser Gly Gly Gly Gly Ser Gly Gly Gly Gly Ser Gly Gly Gly
            100                 105                 110

Gly Ser Glu Leu Thr Gln Ser Pro Ala Ser Leu Ala Val Ser Leu Gly
        115                 120                 125

Gln Arg Ala Thr Ile Ser Tyr Arg Ala Ser Lys Ser Val Ser Thr Ser
    130                 135                 140

Gly Tyr Ser Tyr Met His Trp Asn Gln Gln Lys Pro Gly Gln Pro Pro
145                 150                 155                 160

Arg Leu Leu Ile Tyr Leu Val Ser Asn Leu Glu Ser Gly Val Pro Ala
                165                 170                 175

Arg Phe Ser Gly Ser Gly Ser Gly Thr Asp Phe Thr Leu Asn Ile His
            180                 185                 190

Pro Val Glu Glu Glu Asp Ala Ala Thr Tyr Tyr Cys Gln His Ile Arg
        195                 200                 205

Glu Leu Thr Arg Ser Gly Ala Pro Ser Ser
    210                 215

<210> SEQ ID NO 33
<211> LENGTH: 354
<212> TYPE: DNA
<213> ORGANISM: Artificial Sequence
<220> FEATURE:
<223> OTHER INFORMATION: E6_VH1 heavy chain variable region

<400> SEQUENCE: 33
ctgcaggagt ctggaggagg cttggtgcaa cctggaggat ccatgaaact ctcctgtgtt     60
gcctctggat tcacttccag taactactgg ttgaactggg tccgccagtc tccagagagg    120
gggcttgagt gggttgctga aattagattg aaatctaata attatgcaac aaattatgcg    180
gagtctgtga aagggaggtt caccatctca agagacgatt ccaaaagtag tgtctacctg    240
caagtgaaca acttaagagc tgaagacact ggcatttatt actgtaccag gtcaacagct    300
cgggctaccc catactactt tgactactgg ggccaaggga ccacggtcac cgtc          354

<210> SEQ ID NO 34
<211> LENGTH: 353
<212> TYPE: DNA
<213> ORGANISM: Artificial Sequence
<220> FEATURE:
<223> OTHER INFORMATION: E6_VH7 heavy chain variable region

<400> SEQUENCE: 34

```
ctgcagcagt ctggaggagg cttggtgcaa cctggaggat ccatgaaact ctcctgtgtt     60
gcctctggat tcacttccag taactactgg ttgaactggg tccgccagtc tccagagagg    120
gggcttgagt gggttgctga aattagattg aaatctaata attatgcaac aaattatgcg    180
gagtctgtga aagggaggtt caccatctca agagacgatt ccaaaagtag tgtctacctg    240
caagtgaaca acttaagagc tgaagacact ggcatttatt actgtaccag gtcaacagct    300
cgggctaccc catactactt tgactactgg ggccaaggga ccacggtcac ctc           353
```

<210> SEQ ID NO 35
<211> LENGTH: 324
<212> TYPE: DNA
<213> ORGANISM: Artificial Sequence
<220> FEATURE:
<223> OTHER INFORMATION: E6_Vk9 light chain variable region

<400> SEQUENCE: 35

```
gagctcaccc agtctccatc ctccctggct gtgtcagccg gagagaaggt cactatgagc     60
tgcaaatcca gtcagagtct gctcaacagt agagcccgaa agaacttctt gacttggtac    120
cagcagaaac cagggcagtc tcctaaattg ctgatctatt gggcatccac tagggaatct    180
ggggtccctg atcgcttcac aggcagtgga tctgggacag atttcactct caccatcagc    240
agtgtgcagg ctgaagacct ggcagtttat tactgcaaac agtcttataa tctgtacacg    300
ttcggagggg gcaccaagct cgag                                           324
```

<210> SEQ ID NO 36
<211> LENGTH: 292
<212> TYPE: DNA
<213> ORGANISM: Artificial Sequence
<220> FEATURE:
<223> OTHER INFORMATION: C10_VH3 heavy chain variable region

<400> SEQUENCE: 36

```
ctgcaggagt ctgggggagg cttagtgcag cctggagggt cccggaaact ctcctgtgca     60
gcctctggat tcactttcag tagctttgga atgcactggg ttcgtcaggc tccagagaag    120
gggctggagt gggtcgcata cattagtagt ggcagtagta ccctccacta tgcagacaca    180
gtgaagggcc gattcaccat ctccagagac aatcccaaga acaccctgtt cctgcaaatg    240
aaactaccct cactatgcta tggactactg gggccaaggg accacggtca cc            292
```

<210> SEQ ID NO 37
<211> LENGTH: 292
<212> TYPE: DNA
<213> ORGANISM: Artificial Sequence
<220> FEATURE:
<223> OTHER INFORMATION: C10_VH4 heavy chain variable region

<400> SEQUENCE: 37

```
ctgcagcagt caggggggagg cttagtgcag cctggagggt cccggaaact ctcctgtgca    60
gcctctggat tcactttcag tagctttgga atgcactggg ttcgtcaggc tccagagaag    120
gggctggagt gggtcgcata cattagtagt ggcagtagta ccctccacta tgcagacaca    180
gtgaagggcc gattcaccat ctccagagac aatcccaaga acaccctgtt cctgcaaatg    240
aaactaccct cactatgcta tggactactg gggccaaggg accacggtca cc            292
```

<210> SEQ ID NO 38
<211> LENGTH: 317
<212> TYPE: DNA
<213> ORGANISM: Artificial Sequence
<220> FEATURE:
<223> OTHER INFORMATION: C10_Vk3 light chain variable region

<400> SEQUENCE: 38

| | |
|---|---|
| gagctcaccc agtctcctgc ttccttagct gtatctctgg ggcagagggc caccatctca | 60 |
| tacagggcca gcaaaagtgt cagtacatct ggctatagtt atatgcactg gaaccaacag | 120 |
| aaaccaggac agccacccag actcctcatc tatcttgtat ccaacctaga atctggggtc | 180 |
| cctgccaggt tcagtggcag tgggtctggg acagacttca ccctcaacat ccatcctgtg | 240 |
| gaggaggagg atgctgcaac ctattactgt cagcacatta gggagcttac acgttcggag | 300 |
| ggggcaccaa gctcgag | 317 |

<210> SEQ ID NO 39
<211> LENGTH: 836
<212> TYPE: DNA
<213> ORGANISM: Artificial Sequence
<220> FEATURE:
<223> OTHER INFORMATION: E6_VH1 Vk9 clone complete with Igk secretion
      signal and c-myc peptide

<400> SEQUENCE: 39

| | |
|---|---|
| atgggtgaca atgacatcca ctttgccttt ctctccacag gtgtccactc ccaggtccac | 60 |
| tgcaggagtc tggaggaggc ttggtgcaac ctggaggatc catgaaactc tcctgtgttg | 120 |
| cctctggatt cacttccagt aactactggt tgaactgggt ccgccagtct ccagagaggg | 180 |
| ggcttgagtg ggttgctgaa attagattga atctaataa ttatgcaaca aattatgcgg | 240 |
| agtctgtgaa agggaggttc accatctcaa gagacgattc caaaagtagt gtctacctgc | 300 |
| aagtgaacaa cttaagagct gaagacactg gcatttatta ctgtaccagg tcaacagctc | 360 |
| gggctacccc atactacttt gactactggg gccaagggac cacggtcacc gtctcctcag | 420 |
| gtggaggcgg ttcaggcgga ggtggctctg gcggtggcgg atcggacatc gagctcaccc | 480 |
| agtctccatc ctccctggct gtgtcagccg gagagaaggt cactatgagc tgcaaatcca | 540 |
| gtcagagtct gctaacagt agagcccgaa agaacttctt gacttggtac agcagaaac | 600 |
| cagggcagtc tcctaaattg ctgatctatt gggcatccac tagggaatct ggggtccctg | 660 |
| atcgcttcac aggcagtgga tctgggacag atttcactct caccatcagc agtgtgcagg | 720 |
| ctgaagacct ggcagtttat tactgcaaac agtcttataa tctgtacacg ttcggagggg | 780 |
| gcaccaagct cgagatcaaa cgggaacaaa aactcatctc agaagaggat ctgaat | 836 |

<210> SEQ ID NO 40
<211> LENGTH: 735
<212> TYPE: DNA
<213> ORGANISM: Artificial Sequence
<220> FEATURE:
<223> OTHER INFORMATION: E6_VH1 Vk9 clone full

<400> SEQUENCE: 40

| | |
|---|---|
| ctgcaggagt ctggaggagg cttggtgcaa cctggaggat ccatgaaact ctcctgtgtt | 60 |
| gcctctggat tcacttccag taactactgg ttgaactggg tccgccagtc tccagagagg | 120 |
| gggcttgagt gggttgctga aattagattg aaatctaata attatgcaac aaattatgcg | 180 |
| gagtctgtga aagggaggtt caccatctca agagacgatt ccaaaagtag tgtctacctg | 240 |
| caagtgaaca acttaagagc tgaagacact ggcatttatt actgtaccag gtcaacagct | 300 |
| cgggctaccc catactactt tgactactgg ggccaaggga ccacggtcac cgtctcctca | 360 |
| ggtggaggcg gttcaggcgg aggtggctct ggcggtggcg gatcggacat cgagctcacc | 420 |

```
cagtctccat cctccctggc tgtgtcagcc ggagagaagg tcactatgag ctgcaaatcc    480
agtcagagtc tgctcaacag tagagcccga agaacttct tgacttggta ccagcagaaa    540
ccagggcagt ctcctaaatt gctgatctat tgggcatcca ctagggaatc tggggtccct    600
gatcgcttca caggcagtgg atctgggaca gatttcactc tcaccatcag cagtgtgcag    660
gctgaagacc tggcagttta ttactgcaaa cagtcttata atctgtacac gttcggaggg    720
ggcaccaagc tcgag                                                    735
```

```
<210> SEQ ID NO 41
<211> LENGTH: 835
<212> TYPE: DNA
<213> ORGANISM: Artificial Sequence
<220> FEATURE:
<223> OTHER INFORMATION: E6_VH7 Vk9 clone complete with Igk secretion
      signal and c-myc peptide

<400> SEQUENCE: 41
atgggtgaca atgacatcca ctttgccttt ctctccacag gtgtccactc ccaggtccac     60
tgcagcagtc tggaggaggc ttggtgcaac ctggaggatc catgaaactc tcctgtgttg    120
cctctggatt cacttccagt aactactggt tgaactgggt ccgccagtct ccagagaggg    180
ggcttgagtg ggttgctgaa attagattga atctaataa ttatgcaaca aattatgcgg    240
agtctgtgaa agggaggttc accatctcaa gagacgattc caaaagtagt gtctacctgc    300
aagtgaacaa cttaagagct gaagacactg gcatttatta ctgtaccagg tcaacagctc    360
gggctacccc atactacttt gactactggg gccaagggac cacggtcacc tctcctcagg    420
tggaggcggt tcaggcggag gtggctctgg cggtggcgga tcggacatcg agctcaccca    480
gtctccatcc tccctggctg tgtcagccgg agagaaggtc actatgagct gcaaatccag    540
tcagagtctg ctcaacagta gagcccgaaa gaacttcttg acttggtacc agcagaaacc    600
agggcagtct cctaaattgc tgatctattg gcatccact agggaatctg ggtccctga    660 tcgcttcaca ggcagtggat ctgggacaga tttcactctc accatcagca gtgtgcaggc    720
tgaagacctg gcagtttatt actgcaaaca gtcttataat ctgtacacgt tcggagggg    780 caccaagctc gagatcaaac gggaacaaaa actcatctca gaagaggatc tgaat         835
```

```
<210> SEQ ID NO 42
<211> LENGTH: 734
<212> TYPE: DNA
<213> ORGANISM: Artificial Sequence
<220> FEATURE:
<223> OTHER INFORMATION: E6_VH7 Vk9 clone full

<400> SEQUENCE: 42
ctgcagcagt ctggaggagg cttggtgcaa cctggaggat ccatgaaact ctcctgtgtt     60
gcctctggat tcacttccag taactactgg ttgaactggg tccgccagtc tccagagagg    120
gggcttgagt gggttgctga aattagattg aatctaata attatgcaac aaattatgcg    180
gagtctgtga aagggaggtt caccatctca agagacgatt ccaaaagtag tgtctacctg    240
caagtgaaca acttaagagc tgaagacact ggcatttatt actgtaccag gtcaacagct    300
cgggctaccc catactactt tgactactgg ggccaaggga ccacggtcac ctctcctcag    360
gtggaggcgg ttcaggcgga ggtggctctg gcggtggcgg atcggacatc gagctcaccc    420
agtctccatc ctccctggct gtgtcagccg gagagaaggt cactatgagc tgcaaatcca    480
gtcagagtct gctcaacagt agagcccgaa agaacttctt gacttggtac cagcagaaac    540
```

```
cagggcagtc tcctaaattg ctgatctatt gggcatccac tagggaatct ggggtccctg    600
atcgcttcac aggcagtgga tctgggacag atttcactct caccatcagc agtgtgcagg    660
ctgaagacct ggcagtttat tactgcaaac agtcttataa tctgtacacg ttcggagggg    720
gcaccaagct cgag                                                      734

<210> SEQ ID NO 43
<211> LENGTH: 767
<212> TYPE: DNA
<213> ORGANISM: Artificial Sequence
<220> FEATURE:
<223> OTHER INFORMATION: C10_VH3 Vk3 clone complete with Igk secretion
      signal and c-myc peptide

<400> SEQUENCE: 43
atgggtgaca atgacatcca ctttgccttt ctctccacag gtgtccactc ccaggtccac     60
tgcaggagtc tgggggaggc ttagtgcagc ctggagggtc ccggaaactc tcctgtgcag    120
cctctggatt cactttcagt agctttggaa tgcactgggt tcgtcaggct ccagagaagg    180
ggctggagtg ggtcgcatac attagtagtg gcagtagtac cctccactat gcagacacag    240
tgaagggccg attcaccatc tccagagaca atcccaagaa caccctgttc ctgcaaatga    300
aactaccctc actatgctat ggactactgg ggccaaggga ccacggtcac ctcctcaggt    360
ggaggcggtt caggcggagg tggctctggc ggtggcggat cggacatcga gctcacccag    420
tctcctgctt ccttagctgt atctctgggg cagagggcca ccatctcata cagggccagc    480
aaaagtgtca gtacatctgg ctatagttat atgcactgga accaacagaa accaggacag    540
ccacccagac tcctcatcta tcttgtatcc aacctagaat ctggggtccc tgccaggttc    600
agtggcagtg ggtctgggac agacttcacc ctcaacatcc atcctgtgga ggaggaggat    660
gctgcaacct attactgtca gcacattagg gagcttacac gttcggaggg ggcaccaagc    720
tcgagatcaa cgggaacaa aaactcatct cagaagagga tctgaat                   767

<210> SEQ ID NO 44
<211> LENGTH: 666
<212> TYPE: DNA
<213> ORGANISM: Artificial Sequence
<220> FEATURE:
<223> OTHER INFORMATION: C10_VH3 Vk3 full clone

<400> SEQUENCE: 44
ctgcaggagt ctgggggagg cttagtgcag cctggagggt cccggaaact ctcctgtgca     60
gcctctggat tcactttcag tagctttgga atgcactggg ttcgtcaggc tccagagaag    120
gggctggagt gggtcgcata cattagtagt ggcagtagta ccctccacta tgcagacaca    180
gtgaagggcc gattcaccat ctccagagac aatcccaaga acaccctgtt cctgcaaatg    240
aaactaccct cactatgcta tggactactg gggccaaggg accacggtca cctcctcagg    300
tggaggcggt tcaggcggag gtggctctgg cggtggcgga tcggacatcg agctcaccca    360
gtctcctgct tccttagctg tatctctggg gcagagggcc accatctcat acagggccag    420
caaaagtgtc agtacatctg gctatagtta tatgcactgg aaccaacaga accaggacag    480 ccacccaga ctcctcatct atcttgtatc caacctagaa tctggggtcc ctgccaggtt    540
cagtggcagt gggtctggga cagacttcac cctcaacatc catcctgtgg aggaggagga    600
tgctgcaacc tattactgtc agcacattag ggagcttaca cgttcggagg gggcaccaag    660
ctcgag                                                              666
```

<210> SEQ ID NO 45
<211> LENGTH: 767
<212> TYPE: DNA
<213> ORGANISM: Artificial Sequence
<220> FEATURE:
<223> OTHER INFORMATION: C10_VH4 Vk3 clone complete with Igk secretion
      signal and c-myc peptide

<400> SEQUENCE: 45

```
atgggtgaca atgacatcca ctttgccttt ctctccacag gtgtccactc ccaggtccac      60
tgcagcagtc aggggagc ttagtgcagc ctggagggtc ccggaaactc tcctgtgcag       120
cctctggatt cactttcagt agctttggaa tgcactgggt tcgtcaggct ccagagaagg     180
ggctggagtg ggtcgcatac attagtagtg gcagtagtac cctccactat gcagacacag    240
tgaagggccg attcaccatc tccagagaca atcccaagaa caccctgttc ctgcaaatga    300
aactaccctc actatgctat ggactactgg ggccaaggga ccacggtcac ctcctcaggt    360
ggaggcggtt caggcggagg tggctctggc ggtggcggat cggacatcga gctcacccag   420
tctcctgctt ccttagctgt atctctgggg cagagggcca ccatctcata cagggccagc    480
aaaagtgtca gtacatctgg ctatagttat atgcactgga accaacagaa accaggacag   540
ccacccagac tcctcatcta tcttgtatcc aacctagaat ctggggtccc tgccaggttc    600
agtggcagtg ggtctgggac agacttcacc ctcaacatcc atcctgtgga ggaggaggat   660
gctgcaacct attactgtca gcacattagg gagcttacac gttcggaggg ggcaccaagc  720
tcgagatcaa acgggaacaa aaactcatct cagaagagga tctgaat                767
```

<210> SEQ ID NO 46
<211> LENGTH: 666
<212> TYPE: DNA
<213> ORGANISM: Artificial Sequence
<220> FEATURE:
<223> OTHER INFORMATION: C10_VH4 Vk3 clone full

<400> SEQUENCE: 46

```
ctgcagcagt caggggagg cttagtgcag cctggagggt cccggaaact ctcctgtgca      60
gcctctggat tcactttcag tagctttgga atgcactggg ttcgtcaggc tccagagaag    120
gggctggagt gggtcgcata cattagtagt ggcagtagta ccctccacta tgcagacaca    180
gtgaagggcc gattcaccat ctccagagac aatcccaaga caccctgtt cctgcaaatg     240 aaactacccct cactatgcta tggactactg gggccaaggg accacggtca cctcctcagg   300
tggaggcggt tcaggcggag gtggctctgg cggtggcgga tcggacatcg agctcaccca   360
gtctcctgct tccttagctg tatctctggg gcagagggcc accatctcat acagggccag   420
caaaagtgtc agtacatctg gctatagtta tatgcactgg aaccaacaga accaggaca    480 gccacccaga ctcctcatct atcttgtatc caacctagaa tctggggtcc ctgccaggtt    540
cagtggcagt gggtctggga cagacttcac cctcaacatc catcctgtgg aggaggagga   600
tgctgcaacc tattactgtc agcacattag ggagcttaca cgttcggagg gggcaccaag    660
ctcgag                                                                666
```

<210> SEQ ID NO 47
<211> LENGTH: 17
<212> TYPE: PRT
<213> ORGANISM: Artificial Sequence
<220> FEATURE:
<223> OTHER INFORMATION: Linker signal

<400> SEQUENCE: 47

Ser Ser Gly Gly Gly Gly Ser Gly Gly Gly Ser Gly Gly Gly Gly
1               5                   10                  15
Ser

<210> SEQ ID NO 48
<211> LENGTH: 20
<212> TYPE: PRT
<213> ORGANISM: Artificial Sequence
<220> FEATURE:
<223> OTHER INFORMATION: Secretory signal

<400> SEQUENCE: 48

Met Gly Asp Asn Asp Ile His Phe Ala Phe Leu Ser Thr Gly Val His
1               5                   10                  15
Ser Gln Val Gln
            20

<210> SEQ ID NO 49
<211> LENGTH: 414
<212> TYPE: PRT
<213> ORGANISM: Human

<400> SEQUENCE: 49

Met Ser Glu Tyr Ile Arg Val Thr Glu Asp Glu Asn Asp Glu Pro Ile
1               5                   10                  15

Glu Ile Pro Ser Glu Asp Asp Gly Thr Val Leu Leu Ser Thr Val Thr
                20                  25                  30

Ala Gln Phe Pro Gly Ala Cys Gly Leu Arg Tyr Arg Asn Pro Val Ser
            35                  40                  45

Gln Cys Met Arg Gly Val Arg Leu Val Glu Gly Ile Leu His Ala Pro
        50                  55                  60

Asp Ala Gly Trp Gly Asn Leu Val Tyr Val Val Asn Tyr Pro Lys Asp
65                  70                  75                  80

Asn Lys Arg Lys Met Asp Glu Thr Asp Ala Ser Ser Ala Val Lys Val
                85                  90                  95

Lys Arg Ala Val Gln Lys Thr Ser Asp Leu Ile Val Leu Gly Leu Pro
            100                 105                 110

Trp Lys Thr Thr Glu Gln Asp Leu Lys Glu Tyr Phe Ser Thr Phe Gly
        115                 120                 125

Glu Val Leu Met Val Gln Val Lys Lys Asp Leu Lys Thr Gly His Ser
130                 135                 140

Lys Gly Phe Gly Phe Val Arg Phe Thr Glu Tyr Glu Thr Gln Val Lys
145                 150                 155                 160

Val Met Ser Gln Arg His Met Ile Asp Gly Arg Trp Cys Asp Cys Lys
                165                 170                 175

Leu Pro Asn Ser Lys Gln Ser Gln Asp Glu Pro Leu Arg Ser Arg Lys
            180                 185                 190

Val Phe Val Gly Arg Cys Thr Glu Asp Met Thr Glu Asp Glu Leu Arg
        195                 200                 205

Glu Phe Phe Ser Gln Tyr Gly Asp Val Met Asp Val Phe Ile Pro Lys
210                 215                 220

Pro Phe Arg Ala Phe Ala Phe Val Thr Phe Ala Asp Asp Gln Ile Ala
225                 230                 235                 240

Gln Ser Leu Cys Gly Glu Asp Leu Ile Ile Lys Gly Ile Ser Val His
                245                 250                 255

-continued

Ile Ser Asn Ala Glu Pro Lys His Asn Ser Asn Arg Gln Leu Glu Arg
            260                 265                 270

Ser Gly Arg Phe Gly Gly Asn Pro Gly Gly Phe Gly Asn Gln Gly Gly
            275                 280                 285

Phe Gly Asn Ser Arg Gly Gly Ala Gly Leu Gly Asn Asn Gln Gly
            290                 295                 300

Ser Asn Met Gly Gly Gly Met Asn Phe Gly Ala Phe Ser Ile Asn Pro
305                 310                 315                 320

Ala Met Met Ala Ala Ala Gln Ala Ala Leu Gln Ser Ser Trp Gly Met
                325                 330                 335

Met Gly Met Leu Ala Ser Gln Gln Asn Gln Ser Gly Pro Ser Gly Asn
            340                 345                 350

Asn Gln Asn Gln Gly Asn Met Gln Arg Glu Pro Asn Gln Ala Phe Gly
            355                 360                 365

Ser Gly Asn Asn Ser Tyr Ser Gly Ser Asn Ser Gly Ala Ala Ile Gly
            370                 375                 380

Trp Gly Ser Ala Ser Asn Ala Gly Ser Gly Ser Gly Phe Asn Gly Gly
385                 390                 395                 400

Phe Gly Ser Ser Met Asp Ser Lys Ser Ser Gly Trp Gly Met
                405                 410

<210> SEQ ID NO 50
<211> LENGTH: 551
<212> TYPE: PRT
<213> ORGANISM: Human

<400> SEQUENCE: 50

Met Asp Glu Leu Phe Pro Leu Ile Phe Pro Ala Glu Pro Ala Gln Ala
1               5                   10                  15

Ser Gly Pro Tyr Val Glu Ile Ile Glu Gln Pro Lys Gln Arg Gly Met
            20                  25                  30

Arg Phe Arg Tyr Lys Cys Glu Gly Arg Ser Ala Gly Ser Ile Pro Gly
            35                  40                  45

Glu Arg Ser Thr Asp Thr Thr Lys Thr His Pro Thr Ile Lys Ile Asn
50                  55                  60

Gly Tyr Thr Gly Pro Gly Thr Val Arg Ile Ser Leu Val Thr Lys Asp
65                  70                  75                  80

Pro Pro His Arg Pro His Pro His Glu Leu Val Gly Lys Asp Cys Arg
                85                  90                  95

Asp Gly Phe Tyr Glu Ala Glu Leu Cys Pro Asp Arg Cys Ile His Ser
            100                 105                 110

Phe Gln Asn Leu Gly Ile Gln Cys Val Lys Lys Arg Asp Leu Glu Gln
            115                 120                 125

Ala Ile Ser Gln Arg Ile Gln Thr Asn Asn Asn Pro Phe Gln Val Pro
            130                 135                 140

Ile Glu Glu Gln Arg Gly Asp Tyr Asp Leu Asn Ala Val Arg Leu Cys
145                 150                 155                 160

Phe Gln Val Thr Val Arg Asp Pro Ser Gly Arg Pro Leu Arg Leu Pro
                165                 170                 175

Pro Val Leu Pro His Pro Ile Phe Asp Asn Arg Ala Pro Asn Thr Ala
            180                 185                 190

Glu Leu Lys Ile Cys Arg Val Asn Arg Asn Ser Gly Ser Cys Leu Gly
            195                 200                 205

Gly Asp Glu Ile Phe Leu Leu Cys Asp Lys Val Gln Lys Glu Asp Ile

```
            210                 215                 220
Glu Val Tyr Phe Thr Gly Pro Gly Trp Glu Ala Arg Gly Ser Phe Ser
225                 230                 235                 240

Gln Ala Asp Val His Arg Gln Val Ala Ile Val Phe Arg Thr Pro Pro
                245                 250                 255

Tyr Ala Asp Pro Ser Leu Gln Ala Pro Val Arg Val Ser Met Gln Leu
            260                 265                 270

Arg Arg Pro Ser Asp Arg Glu Leu Ser Glu Pro Met Glu Phe Gln Tyr
        275                 280                 285

Leu Pro Asp Thr Asp Asp Arg His Arg Ile Glu Glu Lys Arg Lys Arg
    290                 295                 300

Thr Tyr Glu Thr Phe Lys Ser Ile Met Lys Lys Ser Pro Phe Ser Gly
305                 310                 315                 320

Pro Thr Asp Pro Arg Pro Pro Arg Arg Ile Ala Val Pro Ser Arg
                325                 330                 335

Ser Ser Ala Ser Val Pro Lys Pro Ala Pro Gln Pro Tyr Pro Phe Thr
            340                 345                 350

Ser Ser Leu Ser Thr Ile Asn Tyr Asp Glu Phe Pro Thr Met Val Phe
        355                 360                 365

Pro Ser Gly Gln Ile Ser Gln Ala Ser Ala Leu Ala Pro Ala Pro Pro
    370                 375                 380

Gln Val Leu Pro Gln Ala Pro Ala Pro Ala Pro Ala Pro Ala Met Val
385                 390                 395                 400

Ser Ala Leu Ala Gln Ala Pro Ala Pro Val Pro Val Leu Ala Pro Gly
                405                 410                 415

Pro Pro Gln Ala Val Ala Pro Pro Ala Pro Lys Pro Thr Gln Ala Gly
            420                 425                 430

Glu Gly Thr Leu Ser Glu Ala Leu Leu Gln Leu Gln Phe Asp Asp Glu
        435                 440                 445

Asp Leu Gly Ala Leu Leu Gly Asn Ser Thr Asp Pro Ala Val Phe Thr
    450                 455                 460

Asp Leu Ala Ser Val Asp Asn Ser Glu Phe Gln Gln Leu Leu Asn Gln
465                 470                 475                 480

Gly Ile Pro Val Ala Pro His Thr Thr Glu Pro Met Leu Met Glu Tyr
                485                 490                 495

Pro Glu Ala Ile Thr Arg Leu Val Thr Gly Ala Gln Arg Pro Pro Asp
            500                 505                 510

Pro Ala Pro Ala Pro Leu Gly Ala Pro Gly Leu Pro Asn Gly Leu Leu
        515                 520                 525

Ser Gly Asp Glu Asp Phe Ser Ser Ile Ala Asp Met Asp Phe Ser Ala
    530                 535                 540

Leu Leu Ser Gln Ile Ser Ser
545                 550

<210> SEQ ID NO 51
<211> LENGTH: 17
<212> TYPE: PRT
<213> ORGANISM: Artificial Sequence
<220> FEATURE:
<223> OTHER INFORMATION: stanniocalcin signal sequence

<400> SEQUENCE: 51

Met Leu Gln Asn Ser Ala Val Leu Leu Leu Leu Val Ile Ser Ala Ser
1               5                   10                  15

Ala
```

```
<210> SEQ ID NO 52
<211> LENGTH: 22
<212> TYPE: PRT
<213> ORGANISM: Artificial Sequence
<220> FEATURE:
<223> OTHER INFORMATION: signal sequence

<400> SEQUENCE: 52

Met Pro Thr Trp Ala Trp Trp Leu Phe Leu Val Leu Leu Leu Ala Leu
1               5                   10                  15

Trp Ala Pro Ala Arg Gly
            20

<210> SEQ ID NO 53
<211> LENGTH: 20
<212> TYPE: PRT
<213> ORGANISM: Artificial Sequence
<220> FEATURE:
<223> OTHER INFORMATION: Ig  secretory signal

<400> SEQUENCE: 53

Met Gly Asp Asn Asp Ile His Phe Ala Phe Leu Ser Thr Gly Val His
1               5                   10                  15

Ser Gln Val Gln
            20
```

TDP-43-BINDING POLYPEPTIDES USEFUL FOR THE TREATMENT OF NEURODEGENERATIVE DISEASES

This application relates to TDP43 (TAR DNA-binding protein of 43 kDA)-specific binding constructs such as antibodies and fragments thereof that specifically bind to TDP-43. The application also relates to methods of using the TDP-43-binding polypeptides in the diagnosis and treatment of diseases characterized by TDP-43 proteinopathy such as amyotrophic lateral sclerosis, Alzheimer's disease, motor neuron disease, Parkinson's disease and frontotemporal lobar degeneration.

Neurodegenerative diseases are characterized by selective neurodegeneration in specific regions of the brain and spinal cord. Amyotrophic Lateral Sclerosis (ALS), commonly known as "Lou Gehrig's disease", is a progressive neurodegenerative disease of unknown etiology. The disease progressively impairs an individual's ability to control voluntary muscle movement. The disease tends to progress rapidly, leading to paralysis and death within 2-5 years of diagnosis in most cases.

A relatively recent discovery related to TDP-43 has provided fundamental insights into pathogenic mechanisms operative in ALS. TDP-43 was shown to be associated with the p65 sub-unit of the nuclear factor-κB (NF-κB) inflammation-regulating transcription factor in spinal cord samples obtained from ALS patients, but not from spinal cord sample of control patients (V. Swarup et al., 2011, J. Exp. Med., 208:2429-2447).

There are currently few therapeutic options for patients suffering from ALS. The only FDA approved drug for the treatment of ALS is Rilutek®, introduced in 1995, which extends life expectancy in individuals with ALS for a few months. There is therefore a need for new therapeutic approaches for neurodegenerative diseases such as ALS.

As the symptoms of neurodegenerative diseases characterized by TDP-43 proteinopathy are similar to those of other neuromuscular disorders, diseases such as ALS is difficult to diagnose. The diagnosis is usually based on a complete neurological examination and clinical tests. There is therefore a need for methods and reagents for evaluating a subject predisposed to developing a neurodegenerative disease such as ALS and FTLD-U or suffering from these neurodegenerative diseases.

Provided herein are antigen-binding constructs that bind to TDP-43 (TAR DNA-binding protein of 43 kDa), such as antibodies, including fragments, derivatives and variants. In one embodiment, the antigen-binding constructs specifically bind to the RRM-1 domain of TDP-43. In another embodiment, the antigen-binding constructs, when expressed in a cell, inhibits the binding of TDP-43 to the p65 subunit of NF-κB in the cell by at least 5%, 10%, 20%, 30%, 40%, 50% 50%, 70%, 80%, or 90%. In another embodiment, the antigen-binding constructs, when expressed in cells, attenuate the activation of NF-κB in response to LPS in the cells by at least 5%, 10%, 20%, 30%, 40%, 50% 50%, 70%, 80%, or 90%. In another embodiment, the antigen-binding constructs, when expressed in a cell, reduces the level of nuclear TDP-43 in the cell by at least 5%, 10%, 20%, 30%, 40%, 50% 50%, 70%, 80%, or 90%. In another embodiment, the antigen-binding constructs, when expressed in ethacrynic acid-treated Hek293 cells, reduce TDP-43 insolubility by at least 5%, 10%, 20%, 30%, 40%, 50% 50%, 70%, 80%, or 90%. In another embodiment, the antigen-binding constructs, when expressed in Hek 293 cells incubated with TNF alpha, reduce the level of lysine acetylation of cellular TDP-43 by at least 5%, 10%, 20%, 30%, 40%, 50% 50%, 70%, 80%, or 90%.

Provided herein are antigen-binding constructs that specifically bind to TDP-43 comprising at least one complementarity determining region (CDR) selected from the amino acid sequences set forth in (SEQ ID NO: 7), (SEQ ID NO: 8), (SEQ ID NO: 9), (SEQ ID NO: 10), (SEQ ID NO: 11), (SEQ ID NO: 12), (SEQ ID NO: 12), (SEQ ID NO: 14), (SEQ ID NO: 15), (SEQ ID NO: 16), (SEQ ID NO: 17), (SEQ ID NO: 18), (SEQ ID NO: 19), (SEQ ID NO: 20), (SEQ ID NO: 21), (SEQ ID NO: 22), (SEQ ID NO: 23) and (SEQ ID NO: 24).

Also provided herein are antigen-binding constructs that specifically bind to TDP-43 comprising at least one heavy chain variable region VH comprising three VH complementarity determining regions (CDRs), wherein the VH comprises one, two or three of:
 a CDR selected from E6_VH1 CDR1, E6_VH7 CDR1, C10_VH3 CDR1 or C10_VH4 CDR1;
 a CDR selected from E6_VH1 CDR2, E6_VH7 CDR2, C10_VH3 CDR2 or C10_VH4 CDR2; and/or
 a CDR selected from E6_VH1 CDR3, E6_VH7 CDR3, C10_VH3 CDR3 or C10_VH4 CDR3.

In some embodiments, the antigen-binding construct comprises one, two or three VH CDRs that are at least 80%, 85%, 90%, 95%, 96%, 97%, 98% or 99% identical to these VH CDRs. In some embodiments, the antigen-binding construct comprises the VH region of E6_VH1, E6_VH7, C10_VH3 or C10_VH4, or a VH region that is at least 80%, 85%, 90%, 95%, 96%, 97%, 98% or 99% identical to the VH of E6_VH1, E6_VH7, C10_VH3 or C10_VH4.

In some embodiments, the antigen-binding construct further comprise a variable light chain region VL, wherein the VL comprises three VL CDRs, and wherein the VL comprises one, two or three of:
 1. a CDR selected from E6_Vκ9 CDR1 and C10_Vκ3 CDR1;
 2. a CDR selected from E6_Vκ9 CDR2 and C10_Vκ3 CDR2; and/or
 3. a CDR selected from E6_Vκ9 CDR3 or C10_Vκ3 CDR3.

as well as antigen-binding constructs comprising a CDR that is at least 80%, 85%, 90%, 95%, 96%, 97%, 98% or 99% identical to these VL CDRs. In some embodiments, the antigen-binding construct comprises the VL of E6_Vκ9 or C10_Vκ3, or an antigen-binding construct having a VL that is at least 80%, 85%, 90%, 95%, 96%, 97%, 98% or 99% identical to the VL of E6_Vκ9 or C10_Vκ3.

In some embodiments, the antigen binding construct comprises the VH region of E6_VH1 or E6_VH7 and the VL region of E6_Vκ9. In other embodiments, the antigen binding construct comprises the VH region of C10_VH3 or C10_VH4 and the VL region of C10_Vκ3. In other embodiments, the antigen-binding construct comprises the VH of E6_VH7 and the VL of E6_Vκ9, the VH of E6_VH1 and the VL of E6_Vκ9, the VH of C10_VH3 and the VL of C10_Vκ3, or the VH of C10_VH4 and the VL of C10_Vκ3.

In some embodiments, the antigen-binding construct comprises a peptide linker between the VH and VL, optionally the amino acid sequence SSGGGGSGGGGSGGGGS.

In some embodiments, the antigen-binding construct are E6_Vh7Vκ9, E6_Vh1Vκ9, C10_VH3Vκ3 or C10_VH4Vκ3.

In some embodiments, the antigen-binding constructs comprise the six CDRs of E6_VH7Vκ9. In some embodiments, the antigen-binding constructs comprise the six CDRs of E6_Vh1Vκ9. In some embodiments, the antigen-binding constructs comprise the six CDRs of C10_VH3Vκ3. In some embodiments, the antigen-binding constructs comprise the six CDRs of C10_VH4Vκ3.

In some embodiments, the TDP-43 antigen-binding construct comprises a secretory signal peptide. In a specific embodiment, the secretory signal peptide is M G D N D I H F A F L S T G V H S Q V Q. In some embodiments, the TDP-43 antigen-binding construct have an scFv format. In other embodiments, the TDP-43 antigen-binding constructs have an Fab format. In one embodiment, the TDP-43 antigen binding construct has a single domain antibody (camelid) format. In some embodiments, the TDP-43 antigen-binding construct has an (Fab')$_2$ format. The TDP-43 antigen-binding constructs may also comprise an Fc domain. The antigen-binding constructs may also be humanized, or de-immunized.

Also encompassed herein are antigen-binding constructs that specifically bind to an RRM-1 domain of TDP-43, comprising a VH and a VL, such that the construct, when expressed in cells, reduces the interaction of an intracellular TDP-43 polypeptide with an intracellular NF-κB p65 polypeptide, and/or reduces the activation of NF-κB in cells in response to LPS. In some embodiments, the interaction of intracellular TDP-43 polypeptide with intracellular NF-κB p65 polypeptide is reduced 5%, 10%, 20%, 30%, 40%, 50%, 60%, 70%, 80% or 90% or more. In some embodiments, the activation of NF-κB in cells in response to LPS is reduced by 5%, 10%, 20%, 30%, 40%, 50%, 60%, 70%, 80% or 90% or more.

Also provided herein is an antigen-binding construct that blocks by 50%, 60%, 70%, 80% or 90% or more the binding of any of E6_VH1Vk9, E6_VH7Vk9, C10_VH3Vk3 or C10_VH4Vk3 to either TDP-43 or to the RRM-1 domain of TDP-43.

Also described herein are pharmaceutical compositions comprising the antigen-binding construct described above, and pharmaceutically acceptable excipient.

Also described are methods of treating or preventing a disease or disorder characterized by TDP-43 proteinopathy in a subject in need thereof, comprising administering to the subject a therapeutically effective amount of the TDP-43 antigen-binding constructs provided herein.

Provided herein are methods of treating or preventing a disease or disorder characterized by TDP-43 proteinopathy in a subject in need thereof, comprising administering to the subject a therapeutically effective amount of an adeno-associated viral (AAV) vector comprising at least one nucleic acid sequence that encodes at least one TDP-43 antigen-binding construct.

Provided herein is a use of the antigen-binding constructs as defined herein for the manufacture of a medicament for the treatment or prevention of a disease or disorder characterized by TDP-proteinopathy.

Provided herein is a use of the antigen-binding constructs as described herein for the treatment or prevention of a disease or disorder characterized by TDP-proteinopathy.

In some embodiments, the disease or disorder being treated is amyotrophic lateral sclerosis (ALS), Alzheimer's disease, motor neuron disease, Parkinson's disease, fronto-temporal lobar degeneration (FTLD), mild cognitive impairment (MCI), Lewy body disease, brain trauma or cerebral ischemia.

Also provided are methods of producing the antigen-binding constructs comprising culturing a host cell under conditions suitable for expressing the antigen-binding construct, wherein the host cell comprises a polynucleotide encoding a TDP-43 antigen binding construct, and purifying the construct.

Also provided herein are polynucleotide or set of isolated polynucleotides comprising at least one nucleic acid sequence that encodes at least one of the TDP-43 antigen-binding constructs. In one embodiment, the polynucleotide is a cDNA.

Also described herein is vector or set of vectors comprising one or more of the polynucleotides or sets of polynucleotides encoding the antigen-binding constructs.

In some embodiments, the vector is a plasmid, a viral vector, a non-episomal mammalian vector, an expression vector, and a recombinant expression vector. In a specific embodiment, the vector is an adeno-associated viral (AAV) vector. Also described is an isolated host cell comprising one or more polynucleotides encoding TDP-43 antigen binding constructs.

FIG. 2 is a bar graph showing the results of an ELISA assay demonstrating that human recombinant p65_His-Tag directly interacts with human recombinant TDP-43_GST Tag. The results are shown as the Absorbance (ABS) at 450 nm read for varying concentrations amount of human recombinant TDP-43 added to the assay from 0.01 to 0.8 μg/ml.

FIG. 3 is a bar graph showing the results of an ELISA assay demonstrating that interaction between recombinant TDP-43 and NF-κB p65 is blocked by exemplary monoclonal anti-TDP-43 antibodies C10, G8, and E6. The results are shown as the Absorbance (ABS) at 450 nm read for the different recombinant anti-TDP-43 antibodies.

Figure 1:
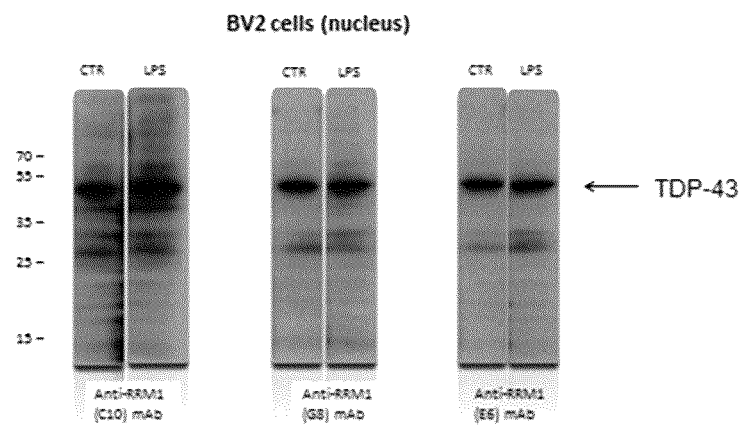
FIG. 1 is an immunoblot of nuclear extracts of BV-2 cells that were fractionated by SDS-PAGE and treated with three exemplary monocloncal anti-TDP-43 antibodies, C10, G8 and E6, raised against the RRMI domain of TDP-43. The three antibodies detected TDP-43 in nuclear extracts of BV-2 cells that were stimulated with LPS or not.

FIG. 4 is a schematic representation of vectors encoding exemplary anti-TDP-43 scFv antibodies. The scFv vectors were constructed in a VH-linker-Vκ format together with a flexible 20-amino acid linker (Gly4Ser)3. The scFv constructs contain a murine immunoglobulin (Ig) κ-secretory signal for efficient secretion and a human c-myc epitope to facilitate detection.

FIG. 5 is an immunoblot of an SDS PAGE gel of nuclear and cytoplasmic fractions of Hek293 cells transfected with an ScFv9 expression plasmids encoding anti-TDP-43 antigen-binding constructs E6_VH1Vκ9 and E6_VH7Vκ9.

FIG. 6 is a dot blot showing that the E6_VH1Vκ9 and E6_VH7Vκ9 antigen-binding constructs bind to amino acids 1-206 of TDP-43.

FIG. 7 shows the results of an ELISA assay demonstrating that exemplary anti-TDP-43 antibodies E6_VH1Vκ9 and E6_VH7Vκ9 having an scFv format block the interaction between recombinant TDP-43 and NF-κB p65.

FIG. 8 shows that an exemplary anti-TDP-43 antibody E6_VH1Vκ9 in an scFv format co-immunoprecipitate with TDP-43 as detected by polyclonal antibodies against TDP-43. (expressed into the medium of Hek293 cells following transfection with ScFv9 expression plasmids encoding E6_VH1Vκ9).

FIG. 9 shows that exemplary anti-TDP-43 antibody E6_VH1Vκ9 having an scFv format blocks the interaction of TDP-43 with NF-κB p65 in Hek293 cells. This was revealed by an assay in which cell extracts from Hek293 cells expressing E6_VH1Vκ9 were immunoprecipitated with anti-TDP-43 polyclonal antibodies, revealing a decreased level of NF-κB p65 for cells expressing VH1Vκ9 compared to cells transfected with an empty ScFv9 expression vector.

FIG. 10 shows the ability of expression vectors encoding exemplary scFv antibodies against TDP-43 to attenuate NF-κB activity in response to LPS as measured by a NF-κB-luciferase reporter construct stably integrated into BV2 microglial cells.

FIG. 11 shows the reduction in levels of nuclear TDP-43 caused by expression of scFv anti-TDP-43 antibodies in Neuro2A cells.

FIG. 12 shows the ability of anti-TDP-43 antibody to reduce TDP-43 insolubility in E6_VH1Vκ9 and E6_VH7Vκ9 transfected Hek293 cells treated with ethacrynic acid. (A) shows a western blot. (B) shows a dot blot analysis.

FIG. 13 shows the ability of anti-TDP-43 antibodies to protect TDP-43 from lysine acetylation in E6_VH1Vκ9 and E6_VH7Vκ9 transfected Hek293 cells.

Disclosed herein are TDP-43-binding constructs and their uses in the diagnosis and therapy of neurodegenerative diseases characterized by TDP-43 proteinopathy.

TDP-43

As used herein, the terms "TDP43," refers to transactivation responsive-DNA binding protein of 43 kDa, or TAR-DNA binding protein of 43 kDA, and is used to refer to all types and forms of TPD-43, including the native form as well as other conformers of TDP-43, including for example, phosphorylated forms of TDP-43, aggregates of TDP-43, ubiquitin-associated aggregates of TDP-43 and TDP-43 variants that have one or more mutations compared to native TDP-43, and pathogenic forms. TDP-43 also includes fragments of TDP-43 polypeptide. TDP-43 is a DNA/RNA-binding protein that contains an N-terminal domain, two RNA-recognition motifs and a glycine-rich C-terminal domain thought to be important for mediating protein-protein interactions The amino acid sequence of human TDP-43 is known in the art; see, e.g., Strausberg et al., TARDBP protein (Homo sapiens) GenBank Pubmed: An amino acid sequence of human TDP 43 is shown in AAH71657 version GL47939520 herein incorporated by reference in its entirety. The amino acid sequence of native human TDP-43 is as shown below and in Table A (SEQ ID NO: 29). The RRM1 domain corresponds to amino acids 101 to 176.

```
                                                    (SEQ ID NO: 50)
      MDELFPLIFPAEPAQASGPYVEIIEQPKQRGMRFRYKCEG

RSAGSIPGERSTDTTKTHPTIKINGYTGPGTVRISLVTKD

PPHRPHPHELVGKDCRDGFYEAELCPDRCIHSFQNLGIQC

VKKRDLEQAISQRIQTNNNPFQVPIEEQRGDYDLNAVRLC

FQVTVRDPSGRPLRLPPVLPHPIFDNRAPNTAELKICRVN

RNSGSCLGGDEIFLLCDKVQKEDIEVYFTGPGWEARGSFS

QADVHRQVAIVFRTPPYADPSLQAPVRVSMQLRRPSDREL

SEPMEFQYLPDTDDRHRIEEKRKRTYETFKSIMKKSPFSG

PTDPRPPPRRIAVPSRSSASVPKPAPQPYPFTSSLSTINY

DEFPTMVFPSGQISQASALAPAPPQVLPQAPAPAPAPAMV

SALAQAPAPVPVLAPGPPQAVAPPAPKPTQAGEGTLSEAL

LQLQFDDEDLGALLGNSTDPAVFTDLASVDNSEFQQLLNQ

GIPVAPHTTEPMLMEYPEATTRLVTGAQRPPDPAPAPLGA

PGLPNGLLSGDEDFSSIADMDFSALLSQISS
```

Neurodegenerative Diseases Characterized by TDP-43 Proteinopathy

The term "TDP-43 proteinopathy" relates to the nervous system diseases, in particular to neurodegenerative diseases, and are known as a heterologous group of disorders linked by association with TDP-43 abnormalities, and particularly with accumulation and/or aggregation of abnormal or misfolded TDP-43 polypeptides. TDP proteinopathies include, but are not limited to amyotrophic lateral sclerosis (ALS), Parkinson's disease, frontotemporal lobar degeneration (FTLD) motor neuron disease, Alzheimer's disease, dementia with Lewy bodies, Huntington's disease, or Lewy body disease. Abnormal TDP-43 accumulations may also be triggered by nerve injury, brain trauma, brain ischemia (stroke).

The term "frontotemporal lobar degeneration disease" refers to a group of disorders associated with atrophy in the frontal and temporal lobes. Frontotemporal lobar degeneration disease (FTLD) can include FTLD-tau characterized by tau inclusion, FTLD-TDP43 characterized by ubiquitin and TDP-43 inclusion (FTLD-U), FTLD-FUS characterized by FUS cytoplasmic inclusions and dementia lacking distinctive histology (DLDH).

```
                                                    (SEQ ID NO: 49)
  1   MSEYIRVTED ENDEPIEIPS EDDGTVLLST VTAQFPGACG LRYRNPVSQC MRGVRLVEGI

61   LHAPDAGWGN LVYVVNYPKD NKRKMDETDA SSAVKVKRAV QKTSDLIVLG LPWKTTEQDL

121   KEYFSTFGEV LMVQVKKDLK TGHSKGFGFV RFTEYETQVK VMSQRHMIDG RWCDCKLPNS

181   KQSQDEPLRS RKVFVGRCTE DMTEDELREF FSQYGDVMDV FIPKPFRAFA FVTFADDQIA

241   QSLCGEDLII KGISVHISNA EPKHNSNRQL ERSGRFGGNP GGFGNQGGFG NSRGGGAGLG

301   NNQGSNMGGG MNFGAFSINP AMMAAAQAAL QSSWGMMGML ASQQNQSGPS GNNQNQGNMQ

361   REPNQAFGSG NNSYSGSNSG AAIGWGSASN AGSGSGFNGG FGSSMDSKSS GWGM
```

NF-kB p65

As used herein the term "NFkB p65 or "NFκB" refers to nuclear factor kappa B, and "NF-kB p65" or "p65" are used interchangeably herein to refer to the p65 subunit or chain of NFkB p65. p65 polypeptides as well as polynucleotides are known in the art. For example see NCBI M62399.1. An amino acid sequence for human NF-κB p65 is shown below. Reference to p65 herein also includes fragments of p65.

The term "amyotrophic lateral sclerosis" (ALS) is used herein to refer to any neurodegenerative disease that usually attacks both upper and lower motor neurons and causes degeneration throughout the brain and spinal cord.

Antigen Binding Constructs

Described herein are antigen-binding constructs that bind to TDP-43 (TAR DNA-binding protein of 43 kDa), such as antibodies, including fragments, derivatives and variants of antibodies that are capable of specifically binding to TDP-43. By "specifically binding to TDP-43", "antibody specific to/for TDP-43" and "anti-TDP-43 antibody" and "TDP-43 antibody" is meant specifically, generally, and collectively, antibodies to TDP-43, or misfolded or oligomeric or aggregated or posttranslationally modified TDP-43 or variants of TDP-43. According to one embodiment, antibodies as described herein (including antigen-binding antibody fragments and derivatives) specifically binds to the RRM-1 domain of TDP-43. In one embodiment, the TDP-43 specific antigen binding construct is an antibody (including antigen-binding fragments or derivatives thereof) having an immunological binding characteristic of the antibodies described herein. In some embodiments, the antigen-binding constructs block the binding of TPD-43 to NF-κB p65.

Described herein are antigen-binding constructs that specifically bind to TDP-43 comprising at least one heavy chain variable region VH comprising three VH complementarity determining regions (CDRs), wherein the VH comprises one, two or three of:
    a CDR selected from E6_VH1 CDR1, E6_VH7 CDR1, C10_VH3 CDR1 or C10_VH4 CDR1;
    a CDR selected from E6_VH1 CDR2, E6_VH7 CDR2, C10_VH3 CDR2 or C10_VH4 CDR2; and/or
    a CDR selected from E6_VH1 CDR3, E6_VH7 CDR3, C10_VH3 CDR3 or C10_VH4 CDR3.

In some embodiments, the antigen-binding construct comprises one, two or three VH CDRs that are at least 80%, 85%, 90%, 95%, 96%, 97%, 98% or 99% identical to the those VH CDRs. In some embodiments, the antigen-binding construct comprises the VH of E6_VH1, E6_VH7, C10_VH3 or C10_VH4, or a VH that is at least 80%, 85%, 90%, 95%, 96%, 97%, 98% or 99% identical to the VH of E6_VH1, E6_VH7, C10_VH3 or C10_VH4.

In some embodiments, the antigen-binding construct of further comprising a variable light chain region VL, wherein the VL comprises three VL CDRs, and wherein the VL comprises one, two or three of:
    a CDR selected from E6_Vκ9 CDR1 and C10_Vκ3 CDR1;
    a CDR selected from E6_Vκ9 CDR2 and C10_Vκ3 CDR2; and/or
    a CDR selected from E6_Vκ9 CDR3 or C10_Vκ3 CDR3;
as well as antigen-binding constructs comprising a CDR that is at least 80%, 85%, 90%, 95%, 96%, 97%, 98% or 99% identical to those VL CDRs. In some embodiments, the antigen-binding construct comprises the VL of E6_Vκ9 or C10_Vκ3, or an antigen-binding construct having a VL that is at least 80%, 85%, 90%, 95%, 96%, 97%, 98% or 99% identical to the VL of E6_Vκ9 or C10_Vκ3.

In some embodiments, the antigen binding construct comprises the VH region of E6_VH1 or E6_VH7 and the VL region of E6_Vκ9. In other embodiments, the antigen binding construct comprises the VH region of C10_VH3 or C10_VH4 and the VL region of C10_Vκ3. In other embodiments, the antigen-binding construct comprises the VH of E6_VH7 and the VL of E6_Vκ9, the VH of E6_VH1 and the VL of E6_Vκ9, the VH of C10_VH3 and the VL of C10_Vκ3, or the VH of C10_VH4 and the VL of C10_Vκ3.

In some embodiments, the antigen-binding construct comprises the six CDRs selected from:
    (a) the CDR1 (SEQ ID NO. 7), CDR2 (SEQ ID NO. 8) and CDR3 (SEQ ID NO. 9), of E6_VH1 and the CDR1 (SEQ ID NO. 7), CDR2 (SEQ ID NO. 8) and CDR3 (SEQ ID NO. 9) of E_6Vκ9;
    (b) the CDR1 (SEQ ID NO. 10), CDR2 (SEQ ID NO. 11) and CDR3 (SEQ ID NO12) of E6_VH7 and the CDR1 (SEQ ID NO. 7), CDR2 (SEQ ID NO. 8) and CDR3 (SEQ ID NO. 9) of E_6Vκ9;
    (c) the CDR1 (SEQ ID NO16), CDR2 (SEQ ID NO. 17) and CDR3 (SEQ ID NO. 18) of C10_VH3, and the CDR1 (SEQ ID NO. 22), CDR2 (SEQ ID NO. 23 and CDR3 (SEQ ID NO. 24) of C10_Vκ3;
    (d) the CDR1 (SEQ ID NO19), CDR2 (SEQ ID NO. 20) and CDR3 (SEQ ID NO. 21) of C10_VH4 and the CDR1 (SEQ ID NO. 22), CDR2 (SEQ ID NO. 23 and CDR3 (SEQ ID NO. 24) of C10_Vκ3.

In some embodiments, the antigen-binding construct comprises a peptide linker between the VH and VL, optionally the amino acid sequence SSGGGGSGGGGSGGGGS.

In some embodiments, the antigen-binding construct comprises E6_Vh7Vκ9, E6_Vh1Vκ9, C10_VH3Vκ3 or C10_VH4Vκ3.

In some embodiments, the antigen-binding construct comprises a secretory signal peptide. In a specific embodiment, the secretory signal peptide is M G D N D I H F A F L S T G V H S Q V Q.

In some embodiments, the antigen-binding construct have an scFv format. In other embodiments, the antigen-binding constructs have an Fab format. In one embodiment, the antigen binding construct has a single domain antibody (for example, a camelid) format. In some embodiments, the antigen-binding construct has an (Fab')$_2$ format. In another embodiment, the antigen-binding construct has an Fab' format. The antigen-binding constructs may also comprise an Fc domain. The antigen-binding constructs may also be humanized, or de-immunized.

Also provided herein are antigen-binding constructs that specifically bind to an RRM-1 domain of TDP-43, comprising a VH and a VL, such that the construct, when expressed in cells, reduces the interaction of an intracellular TDP-43 polypeptide with an intracellular NF-κB p65 polypeptide and/or reduces the activation of NF-κB in cells in response to LPS. In some embodiments, the interaction of intracellular TDP-43 polypeptide with intracellular NF-κB p65 polypeptide is reduced 5%, 10%, 20%, 30%, 40%, 50%, 60%, 70%, 80% or 90% or more. In some embodiments, the activation of NF-κB in cells in response to LPS is reduced by 5%, 10%, 20%, 30%, 40%, 50%, 60%, 70%, 80% or 90% or more.

Also provided herein are antigen-binding constructs that specifically bind to an RRM-1 domain of TDP-43, comprising a VH and a VL, wherein the construct, when expressed in a cell,
    i) reduces the interaction of an intracellular TDP-43 polypeptide with an intracellular NF-κB p65 polypeptide in Hek293 cells by 10% or more; or
    ii) reduces the activation of NF-κB in the BV-2 cells in response to LPS by 10% or more; or
    iii) reduces the level of nuclear TDP-43 in Neuro2A cells; or
    iv) reduces the lysine acetylation of TDP-43 in Hek293 cells in response to TNF alpha by 10% or more; or
    v) reduces the insolubility of TDP-43 in Hek293 cells incubated with ethacrynic acid.

Also provided herein are antigen-binding construct that blocks by 50%, 60%, 70%, 80% or 90% or more the binding of any of E6_VH1Vκ9, E6_VH7Vκ9, C10_VH3Vk3 or C10_VH4Vk3 to either TDP-43 or to the RRM-1 domain of TDP-43. In some embodiments, the antigen-binding construct blocks the binding of any of E6_VH1Vk9, E6_VH7Vk9, C10_VH3Vk3 or C10_VH4Vk3 to either TDP-43 or to the RRM-1 domain of TDP-43 by 50% or more.

The term "antigen binding construct" also refers to any agent, e.g., polypeptide or polypeptide complex capable of binding to an antigen. In some aspects an antigen binding construct is a polypeptide the specifically binds to an antigen of interest. An antigen binding construct can be a monomer, dimer, multimer, a protein, a peptide, or a protein or peptide complex; an antibody, an antibody fragment, or an antigen binding fragment thereof; an scFv and the like. An antigen binding construct can be a polypeptide construct that is monospecific, bispecific, or multispecific. In some aspects, an antigen binding construct can include, e.g., one or more antigen binding components (e.g., Fabs or scFvs) linked to one or more Fc. Further examples of antigen binding constructs are described below and provided in the Examples.

The term "bispecific" is intended to include any agent, e.g., an antigen binding construct or antibody, which has two different binding specificities.

The term "multispecific" or "heterospecific" is intended to include any agent, e.g., an antigen binding construct or antibody, which has two or more different binding specificities. Accordingly, embodiments of the antigen-binding constructs described herein, are inclusive of, but not limited to, bispecific, trispecific, tetraspecific, and other multispecific molecules.

An antigen binding construct can be an antibody or antigen binding portion thereof. As used herein, an "antibody" or "immunoglobulin" refers to a polypeptide substantially encoded by an immunoglobulin gene or immunoglobulin genes, or fragments thereof, which specifically bind and recognize an analyte (e.g., antigen). The recognized immunoglobulin genes include the kappa, lambda, alpha, gamma, delta, epsilon and mu constant region genes, as well as the myriad immunoglobulin variable region genes. Light chains are classified as either kappa or lambda. The "class" of an antibody or immunoglobulin refers to the type of constant domain or constant region possessed by its heavy chain. There are five major classes of antibodies: IgA, IgD, IgE, IgG, and IgM, and several of these may be further divided into subclasses (isotypes), e.g., IgGi, $IgG_2$, $IgG_3$, $IgG_4$, IgAi, and $IgA_2$. The heavy chain constant domains that correspond to the different classes of immunoglobulins are called α, δ, ε, γ, and μ, respectively.

An exemplary immunoglobulin (antibody) structural unit is composed of two pairs of polypeptide chains, each pair having one "light" (about 25 kD) and one "heavy" chain (about 50-70 kD). The N-terminal domain of each chain defines a variable region of about 100 to 110 or more amino acids primarily responsible for antigen recognition. The terms variable light chain (VL) and variable heavy chain (VH) refer to these light and heavy chain domains respectively. The IgG1 heavy chain comprises the VH, CH1, CH2 and CH3 domains respectively from the N to C-terminus. The light chain comprises the VL and CL domains from N to C terminus. The IgG1 heavy chain comprises a hinge between the CH1 and CH2 domains. In certain embodiments, the immunoglobulin constructs comprise at least one immunoglobulin domain from IgG, IgM, IgA, IgD, or IgE connected to a therapeutic polypeptide. In some embodiments, the immunoglobulin domain found in an antigen binding construct provided herein, is from or derived from an immunoglobulin based construct such as a diabody, or a nanobody. In certain embodiments, the immunoglobulin constructs described herein comprise at least one immunoglobulin domain from a heavy chain antibody such as a camelid antibody. In certain embodiments, the immunoglobulin constructs provided herein comprise at least one immunoglobulin domain from a mammalian antibody such as a bovine antibody, a human antibody, a camelid antibody, a mouse antibody or any chimeric antibody.

The term "hypervariable region" or "HVR", as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the complementarity determining regions (CDRs), the latter being of highest sequence variability and/or involved in antigen recognition. With the exception of CDR1 in VH, CDRs generally comprise the amino acid residues that form the hypervariable loops. Hypervariable regions (HVRs) are also referred to as "complementarity determining regions" (CDRs), and these terms are used herein interchangeably in reference to portions of the variable region that form the antigen binding regions. This particular region has been described by Kabat et al., U.S. Dept. of Health and Human Services, Sequences of Proteins of Immunological Interest (1983) and by Chothia et al., J Mol Biol 196:901-917 (1987), where the definitions include overlapping or subsets of amino acid residues when compared against each other. Nevertheless, application of either definition to refer to a CDR of an antibody or variants thereof is intended to be within the scope of the term as defined and used herein. The exact residue numbers which encompass a particular CDR will vary depending on the sequence and size of the CDR. Those skilled in the art can routinely determine which residues comprise a particular CDR given the variable region amino acid sequence of the antibody.

An "Fab molecule" or a "Fab" refers to a protein or polypeptide construct consisting of the VH and CH1 domain of the heavy chain (the "Fab heavy chain") and the VL and CL domain of the light chain (the "Fab light chain") of an immunoglobulin. A Fab is monovalent.

An "F(ab')$_2$" molecule refers to a protein or polypeptide construct consisting of two Fabs linked together by part of a hinge region, but is missing the most of the Fc. An F(ab')$_2$ molecule may be obtained by digesting an immunoglobulin with papain or pepsin.

As used herein, the term "single-chain" refers to a molecule comprising amino acid monomers linearly linked by peptide bonds. In certain embodiments, one of the antigen binding moieties is a single-chain Fab molecule, i.e. a Fab molecule wherein the Fab light chain and the Fab heavy chain are connected by a peptide linker to form a single peptide chain. In a particular such embodiment, the C-terminus of the Fab light chain is connected to the N-terminus of the Fab heavy chain in the single-chain Fab molecule. In certain other embodiments, one of the antigen binding moieties is a single-chain Fv molecule (scFv). As described in more detail herein, an "scFv" has a variable domain of light chain (VL) connected from its C-terminus to the N-terminal end of a variable domain of heavy chain (VH) by a polypeptide chain, or alternately the C-terminal end of the VH is connected to the N-terminal end of VL by a polypeptide chain. Antibodies of this type are referred to herein as having an "scFv format".

In some embodiments described herein, an scFv format is used in an antigen-binding construct (i.e. antigen-binding domains composed of a heavy chain variable domain and a light chain variable domain). In one embodiment said scFv molecules are human. In another embodiment said scFv molecules are humanized. In one embodiment said scFv molecules are murine. The variable regions may be connected directly or, typically, via a linker peptide that allows the formation of a functional antigen-binding moiety. Typical peptide linkers comprise about 2-20 amino acids, and are described herein or known in the art. Suitable, non-immunogenic linker peptides include, for example, (G4S)n, (SG4) n, (G4S)n, G4(SG4)n or G2(SG2)n linker peptides, wherein n is generally a number between 1 and 10, typically between 2 and 4. The scFv molecule may be further stabilized by disulfide bridges between the heavy and light chain variable domains, for example as described in Reiter et al. (Nat Biotechnol 14, 1239-1245 (1996)). As is known in the art, scFvs can also be stabilized by mutation of CDR sequences, as described in [Miller et al., Protein Eng Des Sel. 2010 July; 23(7):549-57; Igawa et al., MAbs. 2011 May-June; 3(3): 243-5; Perchiacca & Tessier, Annu Rev Chem Biomol Eng. 2012; 3:263-86.]. In some embodiments, an TDP-43 antigen-binding construct in an scFv format is preferred for its ability to cross cell membranes and enter cells. A schematic representation of an scFv format antibody is shown in FIG. 4B.

In some embodiments, a TDP-43 antigen-binding construct may consist of a single VH polypeptide (camelid format).

By a "crossover" Fab molecule (also termed "Crossfab") is meant a Fab molecule wherein either the variable regions or the constant regions of the Fab heavy and light chain are exchanged, i.e. the crossover Fab molecule comprises a peptide chain composed of the light chain variable region and the heavy chain constant region, and a peptide chain composed of the heavy chain variable region and the light chain constant region. For clarity, in a crossover Fab molecule wherein the variable regions of the Fab light chain and the Fab heavy chain are exchanged, the peptide chain comprising the heavy chain constant region is referred to herein as the "heavy chain" of the crossover Fab molecule. Conversely, in a crossover Fab molecule wherein the constant regions of the Fab light chain and the Fab heavy chain are exchanged, the peptide chain comprising the heavy chain variable region is referred to herein as the "heavy chain" of the crossover Fab molecule.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The antigen-binding constructs may comprise an Fc region or domain, e.g., a dimeric Fc.

The term "Fc domain" or "Fc region" herein is used to define a C-terminal region of an immunoglobulin heavy chain that contains at least a portion of the constant region. The term includes native sequence Fc regions and variant Fc regions. Unless otherwise specified herein, numbering of amino acid residues in the Fc region or constant region is according to the EU numbering system, also called the EU index, as described in Kabat et al, Sequences of Proteins of Immunological Interest, 5th Ed. Public Health Service, National Institutes of Health, Bethesda, Md., 1991. A "subunit" of an Fc domain as used herein refers to one of the two polypeptides forming the dimeric Fc domain, i.e. a polypeptide comprising C-terminal constant regions of an immunoglobulin heavy chain, capable of stable self-association. For example, a subunit of an IgG Fc domain comprises an IgG $C_{H2}$ and an IgG $C_{H3}$ constant domain.

In some aspects, the Fc comprises at least one or two $C_{H3}$ sequences. In some aspects, the Fc is a homodimeris Fc. In some aspects the Fc is heterodimeric FC. In some aspects, the Fc is a human Fc. In some aspects, the Fc is a murine Fc. In some aspects, the Fc is a human IgG or IgG1 Fc. In some aspects, the Fc comprises at least one or two $C_{H2}$ sequences.

In some aspects, the Fc comprises one or more modifications in at least one of the $C_{H3}$ sequences. In some aspects, the Fc comprises one or more modifications in at least one of the $C_{H3}$ sequences. In some aspects, the Fc comprises one or more modifications in at least one of the $C_{H2}$ sequences. In some aspects, an Fc is a single polypeptide. In some aspects, an Fc is multiple peptides, e.g., two polypeptides.

Fused or linked means that the components (e.g. a Fab molecule or an scFv molecule and an Fc domain subunit) are linked by peptide bonds, either directly or via one or more peptide linkers.

Antigen-binding constructs bind antigen. As used herein, the term "antigenic determinant" is synonymous with "antigen" and "epitope," and refers to a site (e.g. a contiguous stretch of amino acids or a conformational configuration made up of different regions of non-contiguous amino acids) on a polypeptide macromolecule to which an antigen-binding moiety binds, forming an antigen-binding moiety-antigen complex. The antigen bound by the antigen-binding constructs described herein is TPD-43, and in some embodiments, the RRM-1 domain of TDP-43.

"Specifically binds", "specific binding" or "selective binding" means that the binding is selective for the antigen and can be discriminated from unwanted or non-specific interactions. The ability of an antigen-binding moiety to bind to a specific antigenic determinant can be measured either through an enzyme-linked immunosorbent assay (ELISA) or other techniques familiar to one of skill in the art, e.g. surface plasmon resonance (SPR) technique (analyzed on a BIAcore instrument) (Liljeblad et al, Glyco J 17, 323-329 (2000)), and traditional binding assays (Heeley, Endocr Res 28, 217-229 (2002)). In one embodiment, the extent of binding of an antigen-binding moiety to an unrelated protein is less than about 10% of the binding of the antigen-binding moiety to the antigen as measured, e.g., by SPR. In certain embodiments, an antigen-binding moiety that binds to the antigen, or an antigen-binding molecule comprising that antigen-binding moiety, has a dissociation constant ($K_D$) of <1 μM, <100 nM, <10 nM, <1 nM, <0.1 nM, <0.01 nM, or <0.001 nM (e.g. $10^{-8}$ M or less, e.g. from $10^{-8}$ M to $10^{-13}$ M, e.g., from $10^{-9}$ M to $10^{-13}$ M).

An antibody "which binds" an antigen of interest is one capable of binding that antigen with sufficient affinity such that the antibody is useful as a diagnostic and/or therapeutic agent.

"Affinity" refers to the strength of the sum total of non-covalent interactions between a single binding site of a molecule (e.g., a receptor) and its binding partner (e.g., a ligand). Unless indicated otherwise, as used herein, "binding affinity" refers to intrinsic binding affinity which reflects a 1:1 interaction between members of a binding pair (e.g., an antigen-binding construct and an antigen, or a receptor and its ligand). The affinity of a molecule X for its partner Y can generally be represented by the dissociation constant ($K_D$), which is the ratio of dissociation and association rate constants ($k_{off}$ and $k_{on}$, respectively). Thus, equivalent affinities may comprise different rate constants, as long as the ratio of the rate constants remains the same. Affinity can be measured by well-established methods known in the art, including those described herein. A particular method for measuring affinity is Surface Plasmon Resonance (SPR).

The antigen-binding constructs described herein include at least one antigen-binding polypeptide that binds TDP-43. Table A shows the amino acid sequences of exemplary anti-TDP-43 antigen binding polypeptides. ( )=Igk secretory signal; { }=linker sequence; [ ]=c-myc detection signal.

Also provided herein are nucleic acid sequences encoding the exemplary antigen-binding constructs. Table B shows these exemplary nucleic acid sequences.

TABLE A

SEQUENCES

| SEQ ID NO | DESCRIPTION | SEQUENCE AMINO ACID |
|---|---|---|
| 1 | E6_VH1 heavy chain variable region | LQESGGGLVQPGGSMetKLSCVASGFTSSNYWLNWVRQSPERGLEWVAEIRLKSNNYATNYAESVKGRFTISRDDSKSSVYLQVNNLRAEDTGIYYCTRSTARATPYYFDYWGQGTTVTV |
| 2 | E6_VH7 heavy chain variable region | LQQSGGGLVQPGGSMetKLSCVASGFTSSNYWLNWVRQSPERGLEINVAEIRLKSNNYATNYAESVKGRFTISRDDSKSSVYLQVNNLRAEDTGIYYCTRSTARATPYYFDYINGQGTTVTV |
| 3 | E6_Vκ9 light chain variable region | ELTQSPSSLAVSAGEKVTMetSCKSSQSLLNSRARKNFLTWYQQKPGQSPKLLIYWASTRESGVPDRFTGSGSGTDFTLTISSVQAEDLAVYYCKQSYNLYTFGGGTKLE |
| 4 | C10_VH3 heavy chain variable region | LQESGGGLVQPGGSRKLSCAASGFTFSSFGMetHWVRQAPEKGLEINVAYISSGSSTLHYADTVKGRFTISRDNPKNTLFLQMetKLPSLCYGLLGPRDHGH |
| 5 | C10_VH4 heavy chain variable region | LQQSGGGLVQPGGSRKLSCAASGFTFSSFGMetHWVRQAPEKGLEINVAYISSGSSTLHYADTVKGRFTISRDNPKNTLFLQMetKLPSLCYGLLGPRDHGH |
| 6 | C10_Vκ3 light chain variable region | ELTQSPASLAVSLGQRATISYRASKSVSTSGYSYMetHWNQQKPGQPPRLLIYLVSNLESGVPARFSGSGSGTDFTLNIHPVEEEDAATYYCQHIRELTRSEGAPSS |
| 7 | E6_VH1 CDR1 | SSNYWLNW |
| 8 | E6_VH1 CDR2 | EIRLKSNNYATNYAE |
| 9 | E6_VH1 CDR3 | RATPYYFDY |
| 10 | E6_VH7 CDR1 | SSNYWLNW |
| 11 | E6_VH7 CDR2 | EIRLKSNNYATNYAE |
| 12 | E6_VH7 CDR3 | RATPYYFDY |
| 13 | E6_Vκ9 CDR1 | KSSQSLLNSRARKNFLT |
| 14 | E6_Vκ9 CDR2 | YWASTRES |
| 15 | E6_Vκ9 CDR3 | KQSYNLYT |
| 16 | C10_VH3 CDR1 | SSFGMetHW |
| 17 | C10_VH3 CDR2 | YISSGSSTLHYAD |
| 18 | C10_VH3 CDR3 | FLQMetKLPSL |
| 19 | C10_VH4 CDR1 | SSFGMetHW |
| 20 | C10_VH4 CDR2 | YISSGSSTLHYAD |
| 21 | C10_VH4 CDR3 | FLQMetKLPSL |
| 22 | C10_Vκ3 CDR1 | RASKSVSTSGYSYMetH |
| 23 | C10_Vκ3 CDR2 | YLVSNLES |
| 24 | C10_Vκ3 CDR3 | QHIRELTR |
| 25 | E6_VH1Vκ9 complete with IGk secretory signal and c-myc peptide | (MGDNDIHFAFLSTGVHSQVQ)LQESGGGLVQPGGSMetKLSCVASGFTSSNYWLNWVRQSPERGLEWVAEIRLKSNNYATNYAESVKGRFTISRDDSKSSVYLQVNNLRAEDTGIYYCTRSTARATPYYFDYWGQGTTVTVSSGG{GGSGGGGSGGGGSDI}ELTQSPSSLAVSAGEKVTMetSCKSSQSLLNSRARKNFLTWYQQKPGQSPKLLIYWASTRESGVPDR |

TABLE A-continued

SEQUENCES

| SEQ ID NO | DESCRIPTION | SEQUENCE AMINO ACID |
|---|---|---|
| | | FTGSGSGTDFTLTISSVQAEDLAVYYCKQSYN LYTFGGGTKLE[EQKLISEEDLN]. |
| 26 | E6_VH1Vκ9 full | LQESGGGLVQPGGSMetKLSCVASGFTSSNYW LNWVRQSPERGLEWVAEIRLKSNNYATNYAE SVKGRFTISRDDSKSSVYLQVNNLRAEDTGIY YCTRSTARATPYYFDYWGQGTTVTVSSGG{GGS GGGGSGGGGSDI}ELTQSPSSLAVSAGEKVTMetS CKSSQSLLNSRARKNFLTWYQQKPGQSPKLL IYWASTRESGVPDRFTGSGSGTDFTLTISSVQ AEDLAVYYCKQSYNLYTFGGGTKLE |
| 27 | E6_VH7Vκ9 complete with IGk secretory signal and c-myc peptide | (MGDNDIHFAFLSTGVHSQVQ)LQQSGGGLVQPG GSMetKLSCVASGFTSSNYWLNWVRQSPERG LEWVAEIRLKSNNYATNYAESVKGRFTISRD DSKSSVYLQVNNLRAEDTGIYYCTRSTARAT PYYFDYWGQGTTVTV{SSGGGGSGGGGSGGGGSD I}ELTQSPSSLAVSAGEKVTMetSCKSSQSLLN SRARKNFLTWYQQKPGQSPKLLIYWASTRE SGVPDRFTGSGSGTDFTLTISSVQAEDLAVY YCKQSYNLYTFGGGTKLE[EQKLISEEDLN] |
| 28 | E6_VH7Vκ9 full | LQQSGGGLVQPGGSMetKLSCVASGFTSSNY WLNWVRQSPERGLEWVAEIRLKSNNYATNY AESVKGRFTISRDDSKSSVYLQVNNLRAEDT GIYYCTRSTARATPYYFDYWGQGTTVTV{SSG GGGSGGGGSGGGGSDI}ELTQSPSSLAVSAGEKV TMetSCKSSQSLLNSRARKNFLTWYQQKPGQ SPKLLIYWASTRESGVPDRFTGSGSGTDFTL TISSVQAEDLAVYYCKQSYNLYTFGGGTKLE |
| 29 | C10_VH3Vκ3 complete with IGk secretory signal and c-myc peptide | (MGDNDIHFAFLSTGVHSQVQ)LQESGGGLVQPG GSRKLSCAASGFTFSSFGMetHWVRQAPEKG LEWVAYISSGSSTLHYADTVKGRFTISRDNP KNTLFLQMetKLPSLCYGLLGPRDHGH{SSGGG GSGGGGSGGGGS}ELTQSPASLAVSLGQRATISY RASKSVSTSGYSYMetHWNQQKPGQPPRLLI YLVSNLESGVPARFSGSGSGTDFTLNIHPVE EEDAATYYCQHIRELTRSEGAPSS[EQKLISEE DLN] |
| 30 | C10_VH3Vκ3 full | LQESGGGLVQPGGSRKLSCAASGFTFSSF GMetHWVRQAPEKGLEWVAYISSGSSTLHYA DTVKGRFTISRDNPKNTLFLQMetKLPSLCYG LLGPRDHGH{SSGGGGSGGGGSGGGGS}ELTQSPA SLAVSLGQRATISYRASKSVSTSGYSYMetHW NQQKPGQPPRLLIYLVSNLESGVPARFSGSG SGTDFTLNIHPVEEEDAATYYCQHIRELTRSE GAPSS |
| 31 | C10_VH4Vκ3 complete with IGk secretory signal and c-myc peptide | (MGDNDIHFAFLSTGVHSQVQ)LQQSGGGLVCIPG GSRKLSCAASGFTFSSFGMetHWVRQAPEKG LEWVAYISSGSSTLHYADTVKGRFTISRDNP KNTLFLQMetKLPSLCYGLLGPRDHGH{SSGGG GSGGGGSGGGGS}ELTQSPASLAVSLGQRATISY RASKSVSTSGYSYMetHWNQQKPGQPPRLLI YLVSNLESGVPARFSGSGSGTDFTLNIHPVE EEDAATYYCQHIRELTRSEGAPSS[EQKLISEE DLN] |
| 32 | C10_VH4Vκ3 full | LQQSGGGLVQPGGSRKLSCAASGFTFSSF GMetHWVRQAPEKGLEWVAYISSGSSTLHYA DTVKGRFTISRDNPKNTLFLQMetKLPSLCYG LLGPRDHGH{SSGGGGSGGGGSGGGGS}ELTQSPA SLAVSLGQRATISYRASKSVSTSGYSYMetHW NQQKPGQPPRLLIYLVSNLESGVPARFSGSG SGTDFTLNIHPVEEEDAATYYCQHIRELTRSE GAPSS |
| 49 | TDP-43 | MSEYIRVTED ENDPEIEIPS EDDGTVLLST VTAQFPGACG LRYRNPVSQC MRGVRLVEGI LHAPDAGWGN LVYVVNYPKD NKRKMDETDA SSAVKVKRAV QKTSDLIVLG LPWKTTEQDL KEYFSTFGEV LMVQVKKDLK TGHSKGFGFV RFTEYETQVK VMSQRHMIDG RWCDCKLPNS KQSQDEPLRS RKVFVGRCTE |

TABLE A-continued

SEQUENCES

| SEQ ID NO | DESCRIPTION | SEQUENCE AMINO ACID |
|---|---|---|
| | | DMTEDELREF FSQYGDVMDV FIPKPFRAFA FVTFADDQIA QSLCGEDLII KGISVHISNA EPKHNSNRQL ERSGRFGGNP GGFGNQGGFG NSRGGGAGLG NNQGSNMGGG MNFGAFSINP AMMAAAQAAL QSSWGMMGML ASQQNQSGPS GNNQNQGNMQ REPNQAFGSG NNSYSGSNSG AAIGWGSASN AGSGSGFNGG FGSSMDSKSS GWGM |
| 50 | NF-κB p65 | MDELFPLIFPAEPAQASGPYVEIIEQPKQRGMRFRYKCEGRSAG SIPGERSTDTTKTHPTIKINGYTGPGTVRISLVTKDPPHRPHPHELVGKDCRDGFYEA ELCPDRCIHSFQNLGIQCVKKRDLEQAISQRIQTNNNPFQVPIEEQRGDYDLNAVRLC FQVTVRDPSGRPLRLPPVLPHPIFDNRAPNTAELKICRVNRNSGSCLGGDEIFLLCDK VQKEDIEVYFTGPGWEARGSFSQADVHRQVAIVFRTPPYADPSLQAPVRVSMQLRRPS DRELSEPMEFQYLPDTDDRHRIEEKRKRTYETFKSIMKKSPFSGPTDPRPPPRRIAVP SRSSASVPKPAPQPYPFTSSLSTINYDEFPTMVFPSGQISQASALAPAPPQVLPQAPA PAPAPAMVSALAQAPAPVPVLAPGPPQAVAPPAPKPTQAGEGTLSEALLQLQFDDEDL GALLGNSTDPAVFTDLASVDNSEFQQLLNQGIPVAPHTTEPMLMEYPEATTRLVTGAQ RPPDPAPAPLGAPGLPNGLLSGDEDFSSIADMDFSALLSQISS |

TABLE B

SEQUENCES

| SEQ ID NO | DESCRIPTION | SEQUENCE NUCLEIC ACID |
|---|---|---|
| 33 | E6_VH1 heavy chain variable region | CTGCAGGAGTCTGGAGGAGGCTTGGTGCAACCTGGAGGATCCATGAAACTC TCCTGTGTTGCCTCTGGATTCACTTCCAGTAACTACTGGTTGAACTGGGTCCG CCAGTCTCCAGAGAGGGGGCTTGAGTGGGTTGCTGAAATTAGATTGAAATCT AATAATTATGCAACAAATTATGCGGAGTCTGTGAAAGGGAGGTTCACCATCT CAAGAGACGATTCCAAAAGTAGTGTCTACCTGCAAGTGAACAACTTAAGAG CTGAAGACACTGGCATTTATTACTGTACCAGGTCAACAGCTCGGGCTACCCC ATACTACTTTGACTACTGGGGCCAAGGGACCACGGTCACCGTC |
| 34 | E6_VH7 heavy chain variable region | CTGCAGCAGTCTGGAGGAGGCTTGGTGCAACCTGGAGGATCCATGAAACTCT CCTGTGTTGCCTCTGGATTCACTTCCAGTAACTACTGGTTGAACTGGGTCCGC CAGTCTCCAGAGAGGGGGCTTGAGTGGGTTGCTGAAATTAGATTGAAATCTA ATAATTATGCAACAAATTATGCGGAGTCTGTGAAAGGGAGGTTCACCATCTC AAGAGACGATTCCAAAAGTAGTGTCTACCTGCAAGTGAACAACTTAAGAGC TGAAGACACTGGCATTTATTACTGTACCAGGTCAACAGCTCGGGCTACCCCA TACTACTTTGACTACTGGGGCCAAGGGACCACGGTCACCTC |
| 35 | E6_Vκ9 light chain variable region | GAGCTCACCCAGTCTCCATCCTCCCTGGCTGTGTCAGCCGGAGAGAAGGTCA CTATGAGCTGCAAATCCAGTCAGAGTCTGCTCAACAGTAGAGCCCGAAAGA ACTTCTTGACTTGGTACCAGCAGAAACCAGGGCAGTCTCCTAAATTGCTGAT CTATTGGGCATCCACTAGGGAATCTGGGGTCCCTGATCGCTTCACAGGCAGT GGATCTGGGACAGATTTCACTCTCACCATCAGCAGTGTGCAGGCTGAAGACC TGGCAGTTTATTACTGCAAACAGTCTTATAATCTGTACACGTTCGGAGGGGG CACCAAGCTCGAG |
| 36 | C10_VH3 heavy chain variable region | CTGCAGGAGTCTGGGGGAGGCTTAGTGCAGCCTGGAGGGTCCCGGAAACTC TCCTGTGCAGCCTCTGGATTCACTTTCAGTAGCTTTGGAATGCACTGGGTTCG TCAGGCTCCAGAGAAGGGGCTGGAGTGGGTCGCATACATTAGTAGTGGCAG TAGTACCCTCCACTATGCAGACACAGTGAAGGGCCGATTCACCATCTCCAGA GACAATCCCAAGAACACCCTGTTCCTGCAAATGAAACTACCCTCACTATGCT ATGGACTACTGGGGCCAAGGGACCACGGTCACC |
| 37 | C10_VH4 heavy chain variable region | CTGCAGCAGTCAGGGGAGGCTTAGTGCAGCCTGGAGGGTCCCGGAAACTC TCCTGTGCAGCCTCTGGATTCACTTTCAGTAGCTTTGGAATGCACTGGGTTCG TCAGGCTCCAGAGAAGGGGCTGGAGTGGGTCGCATACATTAGTAGTGGCAG TAGTACCCTCCACTATGCAGACACAGTGAAGGGCCGATTCACCATCTCCAGA GACAATCCCAAGAACACCCTGTTCCTGCAAATGAAACTACCCTCACTATGCT ATGGACTACTGGGGCCAAGGGACCACGGTCACC |
| 38 | C10_Vκ3 light chain variable region | GAGCTCACCCAGTCTCCTGCTTCCTTAGCTGTATCTCTGGGGCAGAGGGCCA CCATCTCATACAGGGCCAGCAAAAGTGTCAGTACATCTGGCTATAGTTATAT GCACTGGAACCAACAGAAACAGGACAGCCACCCAGACTCCTCATCTATTAT GTATCCAACCTAGAATCTGGGGTCCCTGCCAGGTTCAGTGGCAGTGGGTCTG GGACAGACTTCACCCTCAACATCCATCCTGTGGAGGAGGAGGATGCTGCAA CCTATTACTGTCAGCACATTAGGGAGCTTACACGTTCGGAGGGGGCACCAAG CTCGAG |

TABLE B-continued

SEQUENCES

| SEQ ID NO | DESCRIPTION | SEQUENCE NUCLEIC ACID |
|---|---|---|
| 39 | E6_VH1Vκ9 clone complete with Igk secretion signal and c-myc peptide | atggggtgacaatgacatccactttgcctttctctccacaggtgtccactcccaggtccaCTGCAGG AGTCTGGAGGAGGCTTGGTGCAACCTGGAGGATCCATGAAACTCTCCTGTGT TGCCTCTGGATTCACTTCCAGTAACTACTGGTTGAACTGGGTCCGCCAGTCTC CAGAGAGGGGGCTTGAGTGGGTTGCTGAAATTAGATTGAAATCTAATAATTA TGCAACAAATTATGCGGAGTCTGTGAAAGGGAGGTTCACCATCTCAAGAGA CGATTCCAAAAGTAGTGTCTACCTGCAAGTGAACAACTTAAGAGCTGAAGA CACTGGCATTTATTACTGTACCAGGTCAACAGCTCGGGCTACCCCATACTAC TTTGACTACTGGGGCCAAGGGACCACGGTCACCGTCtcctcaggtggaggcggttc aggcggaggtggctctggcggtggcggatcggacatcGAGCTCACCCAGTCTCCATCCT CCCTGGCTGTGTCAGCCGGAGAGAAGGTCACTATGAGCTGCAAATCCAGTCA GAGTCTGCTCAACAGTAGAGCCCGAAAGAACTTCTTGACTTGGTACCAGCAG AAACCAGGGCAGTCTCCTAAATTGCTGATCTATTGGGCATCCACTAGGGAAT CTGGGGTCCCTGATCGCTTCACAGGCAGTGGATCTGGGACAGATTTCACTCT CACCATCAGCAGTGTGCAGGCTGAAGACCTGGCAGTTTATTACTGCAAACAG TCTTATAATCTGTACACGTTCGGAGGGGGCACCAAGCTCGAGatcaaacgggaa caaaaaactcatctcagaagaggatctgaat |
| 40 | E6_VH1Vκ9 clone full | CTGCAGGAGTCTGGAGGAGGCTTGGTGCAACCTGGAGGATCCATGAAACTC TCCTGTGTTGCCTCTGGATTCACTTCCAGTAACTACTGGTTGAACTGGGTCCG CCAGTCTCCAGAGAGGGGGCTTGAGTGGGTTGCTGAAATTAGATTGAAATCT AATAATTATGCAACAAATTATGCGGAGTCTGTGAAAGGGAGGTTCACCATCT CAAGAGACGATTCCAAAAGTAGTGTCTACCTGCAAGTGAACAACTTAAGAG CTGAAGACACTGGCATTTATTACTGTACCAGGTCAACAGCTCGGGCTACCCC ATACTACTTTGACTACTGGGGCCAAGGGACCACGGTCACCGTCtcctcaggtgga ggcggttcaggcggaggtggctctggcggtggcggatcggacatcGAGCTCACCCAGTCT CCATCCTCCCTGGCTGTGTCAGCCGGAGAGAAGGTCACTATGAGCTGCAAAT CCAGTCAGAGTCTGCTCAACAGTAGAGCCCGAAAGAACTTCTTGACTTGGTA CCAGCAGAAACCAGGGCAGTCTCCTAAATTGCTGATCTATTGGGCATCCACT AGGGAATCTGGGGTCCCTGATCGCTTCACAGGCAGTGGATCTGGGACAGATT TCACTCTCACCATCAGCAGTGTGCAGGCTGAAGACCTGGCAGTTTATTACTG CAAACAGTCTTATAATCTGTACACGTTCGGAGGGGGCACCAAGCTCGAG |
| 41 | E6_VH7Vκ9 clone complete with Igk secretion signal and c-myc peptide | atgggtgacaatgacatccactttgcctttctctccacaggtgtccactcccaggtccaCTGCAGC AGTCTGGAGGAGGCTTGGTGCAACCTGGAGGATCCATGAAACTCTCCTGTGT TGCCTCTGGATTCACTTCCAGTAACTACTGGTTGAACTGGGTCCGCCAGTCTC CAGAGAGGGGGCTTGAGTGGGTTGCTGAAATTAGATTGAAATCTAATAATTA TGCAACAAATTATGCGGAGTCTGTGAAAGGGAGGTTCACCATCTCAAGAGA CGATTCCAAAAGTAGTGTCTACCTGCAAGTGAACAACTTAAGAGCTGAAGA CACTGGCATTTATTACTGTACCAGGTCAACAGCTCGGGCTACCCCATACTAC TTTGACTACTGGGGCCAAGGGACCACGGTCACCTCtcctcaggtggaggcggttca ggcggaggtggctctggcggtggcggatcggacatcGAGCTCACCCAGTCTCCATCCTC CCTGGCTGTGTCAGCCGGAGAGAAGGTCACTATGAGCTGCAAATCCAGTCA GAGTCTGCTCAACAGTAGAGCCCGAAAGAACTTCTTGACTTGGTACCAGCAG AAACCAGGGCAGTCTCCTAAATTGCTGATCTATTGGGCATCCACTAGGGAAT CTGGGGTCCCTGATCGCTTCACAGGCAGTGGATCTGGGACAGATTTCACTCT CACCATCAGCAGTGTGCAGGCTGAAGACCTGGCAGTTTATTACTGCAAACAG TCTTATAATCTGTACACGTTCGGAGGGGGCACCAAGCTCGAGatcaaacgggaa caaaaaactcatctcagaagaggatctgaat |
| 42 | E6_VH7Vκ9 clone full | CTGCAGCAGTCTGGAGGAGGCTTGGTGCAACCTGGAGGATCCATGAAACTCT CCTGTGTTGCCTCTGGATTCACTTCCAGTAACTACTGGTTGAACTGGGTCCGC CAGTCTCCAGAGAGGGGGCTTGAGTGGGTTGCTGAAATTAGATTGAAATCTA ATAATTATGCAACAAATTATGCGGAGTCTGTGAAAGGGAGGTTCACCATCTC AAGAGACGATTCCAAAAGTAGTGTCTACCTGCAAGTGAACAACTTAAGAGC TGAAGACACTGGCATTTATTACTGTACCAGGTCAACAGCTCGGGCTACCCCA TACTACTTTGACTACTGGGGCCAAGGGACCACGGTCACCTCtcctcaggtggagg cggttcaggcggaggtggctctggcggtggcggatcggacatcGAGCTCACCCAGTCTCC ATCCTCCCTGGCTGTGTCAGCCGGAGAGAAGGTCACTATGAGCTGCAAATCC AGTCAGAGTCTGCTCAACAGTAGAGCCCGAAAGAACTTCTTGACTTGGTACC AGCAGAAACCAGGGCAGTCTCCTAAATTGCTGATCTATTGGGCATCCACTAG GGAATCTGGGGTCCCTGATCGCTTCACAGGCAGTGGATCTGGGACAGATTTC ACTCTCACCATCAGCAGTGTGCAGGCTGAAGACCTGGCAGTTTATTACTGCA AACAGTCTTATAATCTGTACACGTTCGGAGGGGGCACCAAGCTCGAG |
| 43 | C10_VH3Vκ3 clone complete with Igk secretion signal and c-myc peptide | atgggtgacaatgacatccactttgcctttctctccacaggtgtccactcccaggtccaCTGCAGG AGTCTGGGGGAGGCTTAGTGCAGCCTGGAGGGTCCCGGAAACTCTCCTGTGC AGCCTCTGGATTCACTTTCAGTAGCTTTGGAATGCACTGGGTTCGTCAGGCTC CAGAGAAGGGGCTGGAGTGGGTCGCATACATTAGTAGTGGCAGTAGTACCC TCCACTATGCAGACACAGTGAAGGGCCGATTCACCATCTCCAGAGACAATCC CAAGAACACCCTGTTCCTGCAAATGAAACTACCCTCACTATGCTATGGACTA CTGGGGCCAAGGGACCACGGTCACCtcctcaggtggaggcggttcaggcggaggtggc tctggcggtggcggatcggacatcGAGCTCACCCAGTCTCCTGCTTCCTTAGCTGTAT CTCTGGGGCAGAGGGCCACCATCTCATACAGGGCCAGCAAAAGTGTCAGTA |

TABLE B-continued

SEQUENCES

| SEQ ID NO | DESCRIPTION | SEQUENCE NUCLEIC ACID |
|---|---|---|
| | | CATCTGGCTATAGTTATATGCACTGGAACCAACAGAAACCAGGACAGCCAC<br>CCAGACTCCTCATCTATCTTGTATCCAACCTAGAATCTGGGTCCCTGCCAG<br>GTTCAGTGGCAGTGGGTCTGGGACAGACTTCACCCTCAACATCCATCCTGTG<br>GAGGAGGAGGATGCTGCAACCTATTACTGTCAGCACATTAGGGAGCTTACA<br>CGTTCGGAGGGGGCACCAAGCTCGAGatcaaacgggaacaaaaactcatctcagaaga<br>ggatctgaat |
| 44 | C10_VH3Vκ3 clone full | CTGCAGGAGTCTGGGGGAGGCTTAGTGCAGCCTGGAGGGTCCCGGAAACTC<br>TCCTGTGCAGCCTCTGGATTCACTTTCAGTAGCTTTGGAATGCACTGGGTTCG<br>TCAGGCTCCAGAGAAGGGGCTGGAGTGGGTCGCATACATTAGTAGTGGCAG<br>TAGTACCCTCCACTATGCAGACACAGTGAAGGGCCGATTCACCATCTCCAGA<br>GACAATCCCAAGAACACCCTGTTCCTGCAAATGAAACTACCCTCACTATGCT<br>ATGGACTACTGGGGCCAAGGGACCACGGTCACCtcctcaggtggaggcggttcagg<br>cggaggtggctctggcggtggcggatcggacatcGAGCTCACCCAGTCTCCTGCTTCCT<br>TAGCTGTATCTCTGGGGCAGAGGGCCACCATCTCATACAGGGCCAGCAAAA<br>GTGTCAGTACATCTGGCTATAGTTATATGCACTGGAACCAACAGAAACCAGG<br>ACAGCCACCCAGACTCCTCATCTATCTTGTATCCAACCTAGAATCTGGGGTC<br>CCTGCCAGGTTCAGTGGCAGTGGGTCTGGGACAGACTTCACCCTCAACATCC<br>ATCCTGTGGAGGAGGAGGATGCTGCAACCTATTACTGTCAGCACATTAGGGA<br>GCTTACACGTTCGGAGGGGGCACCAAGCTCGAG |
| 45 | C10_VH4Vκ3 clone complete with Igk secretion signal and c-myc peptide | atgggtgacaatgacatccactttgcctttctctccacaggtgtccactcccaggtccaCTGCAGC<br>AGTCAGGGGGAGGCTTAGTGCAGCCTGGAGGGTCCCGGAAACTCTCCTGTG<br>CAGCCTCTGGATTCACTTTCAGTAGCTTTGGAATGCACTGGGTTCGTCAGGCT<br>CCAGAGAAGGGGCTGGAGTGGGTCGCATACATTAGTAGTGGCAGTAGTACC<br>CTCCACTATGCAGACACAGTGAAGGGCCGATTCACCATCTCCAGAGACAATC<br>CCAAGAACACCCTGTTCCTGCAAATGAAACTACCCTCACTATGCTATGGACT<br>ACTGGGGCCAAGGGACCACGGTCACCtcctcaggtggaggcggttcaggcggaggtg<br>gctctggcggtggcggatcggacatcGAGCTCACCCAGTCTCCTGCTTCCTTAGCTGT<br>ATCTCTGGGGCAGAGGGCCACCATCTCATACAGGGCCAGCAAAAGTGTCAG<br>TACATCTGGCTATAGTTATATGCACTGGAACCAACAGAAACCAGGACAGCC<br>ACCCAGACTCCTCATCTATCTTGTATCCAACCTAGAATCTGGGGTCCCTGCCA<br>GGTTCAGTGGCAGTGGGTCTGGGACAGACTTCACCCTCAACATCCATCCTGT<br>GGAGGAGGAGGATGCTGCAACCTATTACTGTCAGCACATTAGGGAGCTTAC<br>ACGTTCGGAGGGGGCACCAAGCTCGAGatcaaacgggaacaaaaactcatctcagaag<br>aggatctgaat |
| 46 | C10_VH4Vκ3 clone full | CTGCAGCAGTCAGGGGGAGGCTTAGTGCAGCCTGGAGGGTCCCGGAAACTC<br>TCCTGTGCAGCCTCTGGATTCACTTTCAGTAGCTTTGGAATGCACTGGGTTCG<br>TCAGGCTCCAGAGAAGGGGCTGGAGTGGGTCGCATACATTAGTAGTGGCAG<br>TAGTACCCTCCACTATGCAGACACAGTGAAGGGCCGATTCACCATCTCCAGA<br>GACAATCCCAAGAACACCCTGTTCCTGCAAATGAAACTACCCTCACTATGCT<br>ATGGACTACTGGGGCCAAGGGACCACGGTCACCtcctcaggtggaggcggttcagg<br>cggaggtggctctggcggtggcggatcggacatcGAGCTCACCCAGTCTCCTGCTTCCT<br>TAGCTGTATCTCTGGGGCAGAGGGCCACCATCTCATACAGGGCCAGCAAAA<br>GTGTCAGTACATCTGGCTATAGTTATATGCACTGGAACCAACAGAAACCAGG<br>ACAGCCACCCAGACTCCTCATCTATCTTGTATCCAACCTAGAATCTGGGGTC<br>CCTGCCAGGTTCAGTGGCAGTGGGTCTGGGACAGACTTCACCCTCAACATCC<br>ATCCTGTGGAGGAGGAGGATGCTGCAACCTATTACTGTCAGCACATTAGGGA<br>GCTTACACGTTCGGAGGGGGCACCAAGCTCGAG |
| 47 | Linker signal | SSGGGGSGGGGSGGGGS |
| 48 | Secretory signal | MGDNDIHFAFLSTGVHSQVQ |

Polypeptides and Polynucleotides

The antigen-binding constructs described herein comprise at least one TDP-43-binding polypeptide. Also described are polynucleotides encoding the TDP-43-binding polypeptides described herein.

As used herein, "isolated" means an agent (e.g., a polypeptide or polynucleotide) that has been identified and separated and/or recovered from a component of its natural cell culture environment. Contaminant components of its natural environment are materials that would interfere with diagnostic or therapeutic uses for the antigen-binding construct, and may include enzymes, hormones, and other proteinaceous or non-proteinaceous solutes. Isolated also refers to an agent that has been synthetically produced, e.g., via human intervention.

The terms "polypeptide," "peptide" and "protein" are used interchangeably herein to refer to a polymer of amino acid residues. That is, a description directed to a polypeptide applies equally to a description of a peptide and a description of a protein, and vice versa. The terms apply to naturally occurring amino acid polymers as well as amino acid polymers in which one or more amino acid residues is a non-naturally encoded amino acid. As used herein, the terms encompass amino acid chains of any length, including full length proteins, wherein the amino acid residues are linked by covalent peptide bonds.

The term "amino acid" refers to naturally occurring and non-naturally occurring amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, praline, serine, threonine, tryptophan, tyrosine, and valine) and pyrrolysine and selenocysteine. Amino acid analogs refers to compounds that have the same basic chemical structure as a naturally occurring amino acid, i.e., an a carbon that is bound to a hydrogen, a carboxyl group, an amino group, and an R group, such as, homoserine, norleucine, methionine sulfoxide, methionine methyl sulfonium. Such analogs have modified R groups (such as, norleucine) or modified peptide backbones, but retain the same basic chemical structure as a naturally occurring amino acid. Reference to an amino acid includes, for example, naturally occurring proteogenic L-amino acids; D-amino acids, chemically modified amino acids such as amino acid variants and derivatives; naturally occurring non-proteogenic amino acids such as β-alanine, ornithine, etc.; and chemically synthesized compounds having properties known in the art to be characteristic of amino acids. Examples of non-naturally occurring amino acids include, but are not limited to, α-methyl amino acids (e.g. ca-methyl alanine), D-amino acids, histidine-like amino acids (e.g., 2-amino-histidine, β-hydroxy-histidine, homohistidine), amino acids having an extra methylene in the side chain ("homo" amino acids), and amino acids in which a carboxylic acid functional group in the side chain is replaced with a sulfonic acid group (e.g., cysteic acid). The incorporation of non-natural amino acids, including synthetic non-native amino acids, substituted amino acids, or one or more D-amino acids into the proteins as described herein may be advantageous in a number of different ways. D-amino acid-containing peptides, etc., exhibit increased stability in vitro or in vivo compared to L-amino acid-containing counterparts. Thus, the construction of peptides, etc., incorporating D-amino acids can be particularly useful when greater intracellular stability is desired or required. More specifically, D-peptides, etc., are resistant to endogenous peptidases and proteases, thereby providing improved bioavailability of the molecule, and prolonged lifetimes in vivo when such properties are desirable. Additionally, D-peptides, etc., cannot be processed efficiently for major histocompatibility complex class II-restricted presentation to T helper cells, and are therefore, less likely to induce humoral immune responses in the whole organism.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

Also included are polynucleotides encoding polypeptides of the antigen-binding constructs. The term "polynucleotide" or "nucleotide sequence" is intended to indicate a consecutive stretch of two or more nucleotide molecules. The nucleotide sequence may be of genomic, cDNA, RNA, semisynthetic or synthetic origin, or any combination thereof.

The term "nucleic acid" refers to deoxyribonucleotides, deoxyribonucleosides, ribonucleosides, or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless specifically limited otherwise, the term also refers to oligonucleotide analogs including PNA (peptidonucleic acid), analogs of DNA used in antisense technology (phosphorothioates, phosphoroamidates, and the like). Unless otherwise indicated, a particular nucleic acid sequence also implicitly encompasses conservatively modified variants thereof (including but not limited to, degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); Rossolini et al., Mol. Cell. Probes 8:91-98 (1994)).

"Conservatively modified variants" applies to both amino acid and nucleic acid sequences. With respect to particular nucleic acid sequences, "conservatively modified variants" refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of ordinary skill in the art will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of ordinary skill in the art will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the deletion of an amino acid, addition of an amino acid, or substitution of an amino acid with a chemically similar amino acid. Conservative substitution tables providing functionally similar amino acids are known to those of ordinary skill in the art. Such conservatively modified variants are in addition to and do not exclude polymorphic variants, interspecies homologs, and alleles as described herein.

Conservative substitution tables providing functionally similar amino acids are known to those of ordinary skill in the art. The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and [0139] 8) Cysteine (C), Methionine (M) (see, e.g., Creighton, Proteins: Structures and Molecular Properties (W H Freeman & Co.; 2nd edition (December 1993)).

The terms "identical" or percent "identity," in the context of two or more nucleic acids or polypeptide sequences, refer to two or more sequences or subsequences that are the same. Sequences are "substantially identical" if they have a percentage of amino acid residues or nucleotides that are the same (i.e., about 60% identity, about 65%, about 70%, about 75%, about 80%, about 85%, about 90%, or about 95% identity over a specified region), when compared and aligned for maximum correspondence over a comparison window, or designated region as measured using one of the following sequence comparison algorithms (or other algorithms available to persons of ordinary skill in the art) or by manual alignment and visual inspection. This definition also refers to the complement of a test sequence. The identity can exist over a region that is at least about 50 amino acids or nucleotides in length, or over a region that is 75-100 amino acids or nucleotides in length, or, where not specified, across the entire sequence of a polynucleotide or polypeptide. A polynucleotide encoding a polypeptide as described herein, including homologs from species other than human, may be obtained by a process comprising the steps of screening a library under stringent hybridization conditions with a labeled probe having a polynucleotide sequence as described herein or a fragment thereof, and isolating full-length cDNA and genomic clones containing said polynucleotide sequence. Such hybridization techniques are well known to the skilled artisan.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are known to those of ordinary skill in the art. Optimal alignment of sequences for comparison can be conducted, including but not limited to, by the local homology algorithm of Smith and Waterman (1970) Adv. Appl. Math. 2:482c, by the homology alignment algorithm of Needleman and Wunsch (1970) J. Mol. Biol. 48:443, by the search for similarity method of Pearson and Lipman (1988) Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., Current Protocols in Molecular Biology (1995 supplement)).

One example of an algorithm that is suitable for determining percent sequence identity and sequence similarity are the BLAST and BLAST 2.0 algorithms, which are described in Altschul et al. (1997) Nuc. Acids Res. 25:3389-3402, and Altschul et al. (1990) J. Mol. Biol. 215:403-410, respectively. Software for performing BLAST analyses is publicly available through the National Center for Biotechnology Information available at the World Wide Web at ncbi.nlm.nih.gov. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1992) Proc. Natl. Acad. Sci. USA 89:10915) alignments (B) of 50, expectation (E) of 10, M=5, N=−4, and a comparison of both strands. The BLAST algorithm is typically performed with the "low complexity" filter turned off.

The BLAST algorithm also performs a statistical analysis of the similarity between two sequences (see, e.g., Karlin and Altschul (1993) Proc. Natl. Acad. Sci. USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, or less than about 0.01, or less than about 0.001.

The phrase "selectively (or specifically) hybridizes to" refers to the binding, duplexing, or hybridizing of a molecule only to a particular nucleotide sequence under stringent hybridization conditions when that sequence is present in a complex mixture (including but not limited to, total cellular or library DNA or RNA).

The phrase "stringent hybridization conditions" refers to hybridization of sequences of DNA, RNA, or other nucleic acids, or combinations thereof under conditions of low ionic strength and high temperature as is known in the art. Typically, under stringent conditions a probe will hybridize to its target subsequence in a complex mixture of nucleic acid (including but not limited to, total cellular or library DNA or RNA) but does not hybridize to other sequences in the complex mixture. Stringent conditions are sequence-dependent and will be different in different circumstances. Longer sequences hybridize specifically at higher temperatures. An extensive guide to the hybridization of nucleic acids is found in Tijssen, Laboratory Techniques in Biochemistry and Molecular Biology—Hybridization with Nucleic Probes, "Overview of principles of hybridization and the strategy of nucleic acid assays" (1993).

As used herein, the terms "engineer, engineered, engineering", are considered to include any manipulation of the peptide backbone or the post-translational modifications of a naturally occurring or recombinant polypeptide or fragment thereof. Engineering includes modifications of the amino acid sequence, of the glycosylation pattern, or of the side chain group of individual amino acids, as well as combinations of these approaches. The engineered proteins are expressed and produced by standard molecular biology techniques.

By "isolated nucleic acid molecule or polynucleotide" is intended a nucleic acid molecule, DNA or RNA, which has been removed from its native environment. For example, a recombinant polynucleotide encoding a polypeptide contained in a vector is considered isolated. Further examples of an isolated polynucleotide include recombinant polynucleotides maintained in heterologous host cells or purified (partially or substantially) polynucleotides in solution. An isolated polynucleotide includes a polynucleotide molecule contained in cells that ordinarily contain the polynucleotide molecule, but the polynucleotide molecule is present extra-chromosomally or at a chromosomal location that is different from its natural chromosomal location. Isolated RNA molecules include in vivo or in vitro RNA transcripts, as well as positive and negative strand forms, and double-stranded forms. Isolated polynucleotides or nucleic acids described herein, further include such molecules produced synthetically, e.g., via PCR or chemical synthesis. In addition, a polynucleotide or a nucleic acid, in certain embodiments, include a regulatory element such as a promoter, ribosome binding site, or a transcription terminator.

The term "polymerase chain reaction" or "PCR" generally refers to a method for amplification of a desired nucleotide sequence in vitro, as described, for example, in U.S. Pat. No. 4,683,195. In general, the PCR method involves repeated cycles of primer extension synthesis, using oligonucleotide primers capable of hybridising preferentially to a template nucleic acid.

By a nucleic acid or polynucleotide having a nucleotide sequence at least, for example, 95% "identical" to a reference nucleotide sequence as described herein, it is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These alterations of the reference sequence may occur at the 5' or 3' terminal positions of the reference nucleotide sequence or anywhere between those terminal positions, interspersed either individually among residues in the reference sequence or in one or more contiguous groups within the reference sequence. As a practical matter, whether any particular polynucleotide sequence is at least 80%, 85%, 90%, 95%, 96%, 97%, 98% or 99% identical to a nucleotide sequence as described herein can be determined conventionally using known computer programs, such as the ones discussed above for polypeptides (e.g. ALIGN-2).

A derivative, or a variant of a polypeptide is said to share "homology" or be "homologous" with the peptide if the amino acid sequences of the derivative or variant has at least 50% identity with a 100 amino acid sequence from the original peptide. In certain embodiments, the derivative or variant is at least 75% the same as that of either the peptide or a fragment of the peptide having the same number of amino acid residues as the derivative. In certain embodiments, the derivative or variant is at least 85% the same as that of either the peptide or a fragment of the peptide having the same number of amino acid residues as the derivative. In certain embodiments, the amino acid sequence of the derivative is at least 90% the same as the peptide or a fragment of the peptide having the same number of amino acid residues as the derivative. In some embodiments, the amino acid sequence of the derivative is at least 95% the same as the peptide or a fragment of the peptide having the same number of amino acid residues as the derivative. In certain embodiments, the derivative or variant is at least 99% the same as that of either the peptide or a fragment of the peptide having the same number of amino acid residues as the derivative.

The term "modified," as used herein refers to any changes made to a given polypeptide, such as changes to the length of the polypeptide, the amino acid sequence, chemical structure, co-translational modification, or post-translational modification of a polypeptide. The form "(modified)" term means that the polypeptides being discussed are optionally modified, that is, the polypeptides under discussion can be modified or unmodified.

In some aspects, an antigen-binding construct comprises an amino acids sequence that is at least 80, 85, 90, 91, 92, 93, 94, 95, 96, 97, 98, 99, or 100% identical to a relevant amino acid sequence or fragment thereof set forth in the Table(s) or accession number(s) disclosed herein. In some aspects, an isolated antigen-binding construct comprises an amino acids sequence encoded by a polynucleotide that is at least 80, 85, 90, 91, 92, 93, 94, 95, 96, 97, 98, 99, or 100% identical to a relevant nucleotide sequence or fragment thereof set forth in Table(s) or accession number(s) disclosed herein.

In certain embodiments the antigen-binding polypeptide is derived from humanized, or chimeric versions of these antibodies.

"Humanized" forms of non-human (e.g., rodent) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also may comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992). In some embodiments, the anti-TDP-43 antigen binding constructs are humanized. In one embodiment, the humanized anti-TDP-43 antibodies comprise the amino acids of murine CDRs.

De-immunization can also be used to decrease the immunogemcity of an antibody.

As used herein, the term "de-immunization" includes alteration of an antibody to modify T cell epitopes; see, e.g., international Application Publication Nos. WO98/52976 and WO00/34317. For example, VH and VL sequences from the starting antibody are analyzed and a human T cell epitope "map" from each V region showing the location of epitopes in relation to complementarity determining regions (CDRs) and other key residues within the sequence. Individual T cell epitopes from the T cell epitope map are analyzed in order to identify alternative amino acid substitutions with a low risk of altering activity of the final antibody. A range of alternative VH and VL sequences are designed comprising combinations of amino acid substitutions and these sequences are subsequently incorporated into a range of binding polypeptides, e.g., TDP-43-specific antibodies, including immunospecific fragments thereof, for use in the diagnostic and treatment methods disclosed herein, which are then tested for function. Typically, between 12 and 24 variant antibodies are generated and tested. Complete heavy and light chain genes comprising modified V and/or C regions are then cloned into expression vectors and the subsequent plasmids introduced into cell lines for the production of whole antibody. The antibodies are then compared in appropriate biochemical and biological assays, and the optimal variant is identified.

Pharmaceutical Compositions

Also provided herein are pharmaceutical compositions comprising an antigen-binding constructs described herein. Such compositions comprise the construct and a pharmaceutically acceptable carrier.

The term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. In some aspects, the carrier is a man-made carrier not found in nature. Water can be used as a carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

In certain embodiments, the composition comprising the construct is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

In certain embodiments, the compositions described herein are formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxide isopropylamine, triethylamine, 2-ethylamino ethanol, histidine, procaine, etc.

Methods of Preparation of TDP-43 Antigen-Binding Constructs

Also described herein are methods of producing the anti-TDP-43 antigen-binding constructs. In certain embodiments the antigen-binding constructs are produced as recombinant molecules by expression in a cell, e.g., yeast, a microorganism such as a bacterium, or a human or animal cell line. In embodiments, the anti-TDP-43 antigen-binding constructs are secreted from the cells.

The antigen-binding constructs can be expressed in a host cell using an expression cassette coding for the antigen-binding construct. The term "expression cassette" refers to a polynucleotide generated recombinantly or synthetically, with a series of specified nucleic acid elements that permit transcription of a particular nucleic acid in a target cell. The recombinant expression cassette can be incorporated into a vector, e.g., a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter. In certain embodiments, the expression cassette as described herein comprises polynucleotide sequences that encode antigen-binding constructs as described herein or fragments thereof.

The term "vector" or "expression vector" is synonymous with "expression construct" and refers to a nucleic acid molecule that is used to introduce and direct the expression of a specific gene to which it is operably associated in a target cell. The term includes the vector as a self-replicating nucleic acid structure as well as the vector incorporated into the genome of a host cell into which it has been introduced. The expression vector as described herein comprises an expression cassette. Expression vectors allow transcription of large amounts of stable mRNA. Once the expression vector is inside the target cell, the ribonucleic acid molecule or protein that is encoded by the gene is produced by the cellular transcription and/or translation machinery. In one embodiment, the expression vector as described herein comprises an expression cassette that comprises polynucleotide sequences that encode antigen-binding constructs as described herein or fragments thereof. Exemplary vectors are described herein.

Typically a host cell is transformed with an expression vector coding for an antigen-binding construct. "Cell", "host cell", "cell line" and "cell culture" are used interchangeably herein and all such terms should be understood to include progeny resulting from growth or culturing of a cell. "Transformation" and "transfection" are used interchangeably to refer to the process of introducing DNA into a cell. Host cells include "transformants" and "transformed cells," which include the primary transformed cell and progeny derived therefrom without regard to the number of passages. In certain embodiments, progeny are not completely identical in nucleic acid content to a parent cell, but may contain mutations. Mutant progeny that have the same function or biological activity as screened or selected for in the originally transformed cell are included herein.

A host cell is any type of cellular system that can be used to generate the antigen-binding constructs as described herein. Host cells include cultured cells, e.g. mammalian cultured cells, such as CHO cells, BHK cells, NS0 cells, SP2/0 cells, YO myeloma cells, P3X63 mouse myeloma cells, PER cells, PER.C6 cells or hybridoma cells, bacteria (for example *E. coli* and *Bacillus subtilis*), yeasts (for example *Saccharomyces cerevisiae, Kluyveromyces lactis* and *Pichia pastoris*, filamentous fungi (for example *Aspergillus*), insect cells, and plant cells, to name only a few, but also cells comprised within a transgenic animal, transgenic plant or cultured plant or animal tissue. Additional examples of host cells are described herein.

In some embodiments, the antigen-binding construct is produced in a mammalian cell. In select embodiments, the mammalian cell is selected from the group consisting of a VERO, HeLa, HEK, NS0, Chinese Hamster Ovary (CHO), W138, BHK, COS-7, Caco-2 and MDCK cell, and subclasses and variants thereof.

Expression Vectors

Provided are vectors containing polynucleotides encoding an antigen-binding construct described herein, host cells, and the production of the antigen-binding construct proteins by synthetic and recombinant techniques. The vector may be, for example, a phage, plasmid, viral, or retroviral vector. Retroviral vectors may be replication competent or replication defective. In the latter case, viral propagation generally will occur only in complementing host cells.

In certain embodiments, the polynucleotides encoding antigen-binding construct proteins described herein are joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

In certain embodiments, the polynucleotide insert is operatively linked to an appropriate promoter, such as the phage lambda PL promoter, the *E. coli* lac, trp, phoA and rac promoters, the SV40 early and late promoters and promoters of retroviral LTRs, to name a few. Other suitable promoters will be known to the skilled artisan. The expression constructs will further contain sites for transcription initiation, termination, and, in the transcribed region, a ribosome binding site for translation. The coding portion of the transcripts expressed by the constructs will preferably include a translation initiating codon at the beginning and a termination codon (UAA, UGA or UAG) appropriately positioned at the end of the polypeptide to be translated.

As indicated, the expression vectors will preferably include at least one selectable marker. Such markers include dihydrofolate reductase, G418, glutamine synthase, or neomycin resistance for eukaryotic cell culture, and tetracycline, kanamycin or ampicillin resistance genes for culturing in *E. coli* and other bacteria. Representative examples of appropriate hosts include, but are not limited to, bacterial cells, such as *E. coli, Streptomyces* and *Salmonella typhimurium* cells; fungal cells, such as yeast cells (e.g., *Saccharomyces cerevisiae* or *Pichia pastoris* (ATCC Accession No. 201178)); insect cells such as *Drosophila* S2 and *Spodoptera* Sf9 cells; animal cells such as CHO, COS, NSO, 293, and Bowes melanoma cells; and plant cells. Appropriate culture mediums and conditions for the above-described host cells are known in the art.

Among vectors preferred for use in bacteria include pQE70, pQE60 and pQE-9, available from QIAGEN, Inc.; pBluescript vectors, Phagescript vectors, pNH8A, pNH16a, pNH18A; pNH46A, available from Stratagene Cloning Systems, Inc.; and ptrc99a, pKK223-3, pKK233-3, pDR540, pRIT5 available from Pharmacia Biotech, Inc. Among preferred eukaryotic vectors are pWLNEO, pSV2CAT, pOG44, pXT1 and pSG available from Stratagene; and pSVK3, pBPV, pMSG and pSVL available from Pharmacia. Preferred expression vectors for use in yeast systems include, but are not limited to pYES2, pYD1, pTEF1/Zeo, pYES2/GS, pPICZ, pGAPZ, pGAPZalph, pPIC9, pPIC3.5, pHIL-D2, pHIL-S1, pPIC3.5K, pPIC9K, and PAO815 (all available from Invitrogen, Carlsbad, Calif.). Other suitable vectors will be readily apparent to the skilled artisan.

In one embodiment, polynucleotides encoding an antigen-binding construct described herein are fused to signal sequences that will direct the localization of a protein as described herein to particular compartments of a prokaryotic or eukaryotic cell and/or direct the secretion of a protein as described herein from a prokaryotic or eukaryotic cell. For example, in *E. coli*, one may wish to direct the expression of the protein to the periplasmic space. Examples of signal sequences or proteins (or fragments thereof) to which the antigen-binding construct proteins are fused in order to direct the expression of the polypeptide to the periplasmic space of bacteria include, but are not limited to, the pelB signal sequence, the maltose binding protein (MBP) signal sequence, MBP, the ompA signal sequence, the signal sequence of the periplasmic *E. coli* heat-labile enterotoxin B-subunit, and the signal sequence of alkaline phosphatase. Several vectors are commercially available for the construction of fusion proteins which will direct the localization of a protein, such as the pMAL series of vectors (particularly the pMAL-.rho. series) available from New England Biolabs. In a specific embodiment, polynucleotides encoding proteins as described herein may be fused to the pelB pectate lyase signal sequence to increase the efficiency of expression and purification of such polypeptides in Gram-negative bacteria. See, U.S. Pat. Nos. 5,576,195 and 5,846,818, the contents of which are herein incorporated by reference in their entireties.

Examples of signal peptides that are fused to an antigen-binding construct protein in order to direct its secretion in mammalian cells include, but are not limited to, the MPIF-1 signal sequence (e.g., amino acids 1-21 of GenBank Accession number AAB51134), the stanniocalcin signal sequence (MLQNSAVLLLLVISASA (SEQ ID NO: 51)), and a consensus signal sequence (MPTWAWWLFLVLLLALWA-PARG (SEQ ID NO: 52)). A suitable signal sequence that may be used in conjunction with baculoviral expression systems is the gp67 signal sequence (e.g., amino acids 1-19 of GenBank Accession Number AAA72759). In one embodiment, the signal sequence is an Igκ secretory signal comprising the amino acid sequence (M G D N D I H F A F L S T G V H S Q V Q (SEQ ID NO: 53)). In one embodiment the Igκ secretory signal is fused to the N-terminal of an TDP-43-binding polypeptide.

Vectors which use glutamine synthase (GS) or DHFR as the selectable markers can be amplified in the presence of the drugs methionine sulphoximine or methotrexate, respectively. An advantage of glutamine synthase based vectors are the availability of cell lines (e.g., the murine myeloma cell line, NSO) which are glutamine synthase negative. Glutamine synthase expression systems can also function in glutamine synthase expressing cells (e.g., Chinese Hamster Ovary (CHO) cells) by providing additional inhibitor to prevent the functioning of the endogenous gene. A glutamine synthase expression system and components thereof are detailed in PCT publications: WO87/04462; WO86/05807; WO89/10036; WO89/10404; and WO91/06657, which are hereby incorporated in their entireties by reference herein. Additionally, glutamine synthase expression vectors can be obtained from Lonza Biologics, Inc. (Portsmouth, N.H.). Expression and production of monoclonal antibodies or antigen-binding constructs using a GS expression system in murine myeloma cells is described in Bebbington et al., Bio/technology 10:169(1992) and in Biblia and Robinson Biotechnol. Prog. 11:1(1995) which are herein incorporated by reference.

Host Cells

Also provided are host cells containing vector constructs described herein, and additionally host cells containing nucleotide sequences that are operably associated with one or more heterologous control regions (e.g., promoter and/or enhancer) using techniques known of in the art. The host cell can be a higher eukaryotic cell, such as a mammalian cell (e.g., a human derived cell), or a lower eukaryotic cell, such as a yeast cell, or the host cell can be a prokaryotic cell, such as a bacterial cell. A host strain may be chosen which modulates the expression of the inserted gene sequences, or modifies and processes the gene product in the specific fashion desired. Expression from certain promoters can be elevated in the presence of certain inducers; thus expression of the genetically engineered polypeptide may be controlled. Furthermore, different host cells have characteristics and specific mechanisms for the translational and post-translational processing and modification (e.g., phosphorylation, cleavage) of proteins. Appropriate cell lines can be chosen to ensure the desired modifications and processing of the foreign protein expressed.

Mammalian cell lines available as hosts for expression are well known in the art and include many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), human epithelial kidney 293 cells, and a number of other cell lines. Cell lines of particular preference are selected through determining which cell lines have high expression levels and produce antibodies with constitutive ManLAM binding properties.

Introduction of the nucleic acids and nucleic acid constructs as described herein into the host cell can be effected by calcium phosphate transfection; DEAE-dextran mediated transfection, cationic lipid-mediated transfection, electroporation, transduction, infection, or other methods. Such methods are described in many standard laboratory manuals, such as Davis et al., Basic Methods In Molecular Biology (1986). It is specifically contemplated that the polypeptides as described herein may in fact be expressed by a host cell lacking a recombinant vector.

In addition to encompassing host cells containing the vector constructs discussed herein, one embodiment also encompasses primary, secondary, and immortalized host cells of vertebrate origin, particularly mammalian origin, that have been engineered to delete or replace endogenous genetic material (e.g., the coding sequence corresponding to a Cargo polypeptide is replaced with an antigen-binding construct protein corresponding to the Cargo polypeptide), and/or to include genetic material. The genetic material operably associated with the endogenous polynucleotide may activate, alter, and/or amplify endogenous polynucleotides.

In addition, techniques known in the art may be used to operably associate heterologous polynucleotides (e.g., polynucleotides encoding a protein, or a fragment or variant thereof) and/or heterologous control regions (e.g., promoter and/or enhancer) with endogenous polynucleotide sequences encoding a therapeutic protein via homologous recombination (see, e.g., U.S. Pat. No. 5,641,670, issued Jun. 24, 1997; International Publication Number WO 96/29411; International Publication Number WO 94/12650; Koller et al., Proc. Natl. Acad. Sci. USA 86:8932-8935 (1989); and Zijlstra et al., Nature 342:435-438 (1989), the disclosures of each of which are incorporated by reference in their entireties).

Purification

Antigen-binding construct proteins described herein can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography such as with protein A, hydroxylapatite chromatography, hydrophobic charge interaction chromatography and lectin chromatography. Most preferably, high performance liquid chromatography ("HPLC") is employed for purification.

In certain embodiments the antigen-binding construct proteins as described herein are purified using Anion Exchange Chromatography including, but not limited to, chromatography on Q-sepharose, DEAE sepharose, poros HQ, poros DEAF, Toyopearl Q, Toyopearl QAE, Toyopearl DEAE, Resource/Source Q and DEAE, Fractogel Q and DEAE columns.

In certain embodiments the proteins described herein may be purified using Cation Exchange Chromatography including, but not limited to, SP-sepharose, CM sepharose, poros HS, poros CM, Toyopearl SP, Toyopearl CM, Resource/Source S and CM, Fractogel S and CM columns and their equivalents and comparables.

Chemical Synthesis and Cell-Free Expression

In addition, antigen-binding construct proteins described herein can be chemically synthesized using techniques known in the art (e.g., see Creighton, 1983, Proteins: Structures and Molecular Principles, W. H. Freeman & Co., N.Y and Hunkapiller et al., Nature, 310:105-111 (1984)). For example, a polypeptide corresponding to a fragment of a polypeptide can be synthesized by use of a peptide synthesizer. Furthermore, if desired, nonclassical amino acids or chemical amino acid analogs can be introduced as a substitution or addition into the polypeptide sequence. Nonclassical amino acids include, but are not limited to, to the D-isomers of the common amino acids, 2,4diaminobutyric acid, alpha-amino isobutyric acid, 4aminobutyric acid, Abu, 2-amino butyric acid, g-Abu, e-Ahx, 6amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogs in general. Furthermore, the amino acid can be D (dextrorotary) or L (levorotary).

In certain embodiments, cell-free protein expression systems are utilized to co-express polypeptides (e.g., heavy and light chain polypeptides) without the use of living cells. Instead, all components needed to transcribe DNA to RNA and translate the RNA to protein (e.g. ribosomes, tRNAs, enzymes, cofactors, amino acids) are provided in solution for use in vitro. In certain embodiments, the in vitro expression requires (1) the genetic template (mRNA or DNA) encoding the heavy and light chain polypeptides and (2) a reaction solution containing the necessary transcriptional and translational molecular machinery. In certain embodiments, cell extracts substantially supply components of the reaction solution, for instance: RNA polymerases for mRNA transcription, ribosomes for polypeptide translation, tRNA, amino acids, enzymatic cofactors, an energy source, and cellular components essential for proper protein folding. Cell-free protein expression systems can be prepared using lysates derived from bacterial cells, yeast cells, insect cells, plant cells, mammalian cells, human cells or combinations thereof. Such cell lysates can provide the correct composition and proportion of enzymes and building blocks required for translation. In some embodiments, cell membranes are removed to leave only the cytosolic and organelle components of the cell.

Several cell-free protein expression systems are known in the art as reviewed in Carlson et al. (2012) Biotechnol. Adv. 30:1185-1194. For example, cell-free protein expression systems are available based on prokaryotic or eukaryotic cells. Examples of prokaryotic cell-free expression systems include those from *E. coli*. Eukaryotic cell-free protein expression systems are available based on extracts from rabbit reticulocytes, wheat germ, and insect cells, for example. Such prokaryotic and eukaryotic cell-free protein expression systems are commercially available from companies such as Roche, Invitrogen, Qiagen, and Novagen. One skilled in the art would readily be able to select suitable cell-free protein expression systems that would produce polypeptides (e.g., heavy chain and light chain polypeptides) that are capable of pairing with each other. Further, the cell-free protein expression system can also be supplemented with chaperones (e.g. BiP) and isomerases (e.g. disulphide isomerase) to improve the efficiency of IgG folding.

In some embodiments, cell-free expression systems are utilized to co-express the heavy and light chain polypeptides from DNA templates (transcription and translation) or mRNA templates (translation only).

Expression in Yeast

In some embodiments, the antigen-binding construct is produced in a yeast cell. The yeasts are transformed with a coding sequence for the desired protein in any of the usual ways, for example electroporation. Methods for transformation of yeast by electroporation are disclosed in Becker & Guarente (1990) Methods Enzymol. 194, 182.

Useful yeast plasmid vectors include pRS403-406 and pRS413-416 and are generally available from Stratagene Cloning Systems, La Jolla, Calif. 92037, USA. Plasmids pRS403, pRS404, pRS405 and pRS406 are Yeast Integrating plasmids (YIps) and incorporate the yeast selectable markers HIS3, 7RP1, LEU2 and URA3. Plasmids pRS413-416 are Yeast Centromere plasmids (Ycps).

Exemplary genera of yeast contemplated to be useful in one embodiment as hosts for expressing the proteins are Pichua (formerly classified as *Hansenula*), *Saccharomyces*, *Kluyveromyces*, *Aspergillus*, *Candida*, *Torulopsis*, *Torulaspora*, *Schizosaccharomyces*, *Citeromyces*, *Pachysolen*, *Zygosaccharomyces*, *Debaromyces*, *Trichoderma*, *Cephalosporium*, *Humicola*, *Mucor*, *Neurospora*, *Yarrowia*, *Metschunikowia*, *Rhodosporidium*, *Leucosporidium*, *Botryoascus*, *Sporidiobolus*, *Endomycopsis*, and the like. Preferred genera are those selected from the group consisting of *Saccharomyces*, *Schizosaccharomyces*, *Kluyveromyces*, *Pichia* and *Torulaspora*. Examples of *Saccharomyces* spp. are *S. cerevisiae*, *S. italicus* and *S. rouxii*.

Examples of *Kluyveromyces* spp. are *K. fragilis*, *K. lactis* and *K. marxianus*. A suitable Torulaspora species is *T. delbrueckii*. Examples of *Pichia* (*Hansenula*) spp. are *P. angusta* (formerly *H. polymorpha*), *P. anomala* (formerly *H. anomala*) and *P. pastoris*. Methods for the transformation of *S. cerevisiae* are taught generally in EP 251 744, EP 258 067 and WO 90/01063, all of which are incorporated herein by reference.

Exemplary species of *Saccharomyces* useful for the synthesis of antigen-binding constructs described herein include *S. cerevisiae*, *S. italicus*, *S. diastaticus*, and *Zygosaccharomyces rouxii*. Preferred exemplary species of *Kluyveromyces* include *K. fragilis* and *K. lactis*. Preferred exemplary species of *Hansenula* include *H. polymorpha* (now *Pichia angusta*), *H. anomala* (now *Pichia anomala*), and *Pichia capsulata*. Additional preferred exemplary species of *Pichia* include *P. pastoris*. Preferred exemplary species of *Aspergillus* include *A. niger* and *A. nidulans*. Preferred exemplary species of *Yarrowia* include *Y. lipolytica*. Many preferred yeast species are available from the ATCC. For example, the following preferred yeast species are available from the ATCC and are useful in the expression of proteins: *Saccharomyces cerevisiae*, Hansen, teleomorph strain BY4743 yap3 mutant (ATCC Accession No. 4022731); *Saccharomyces cerevisiae* Hansen, teleomorph strain BY4743 hsp150 mutant (ATCC Accession No. 4021266); *Saccharomyces cerevisiae* Hansen, teleomorph strain BY4743 pmt1 mutant (ATCC Accession No. 4023792); *Saccharomyces cerevisiae* Hansen, teleomorph (ATCC Accession Nos. 20626; 44773; 44774; and 62995); *Saccharomyces diastaticus* Andrews et Gilliland ex van der Walt, teleomorph (ATCC Accession No. 62987); *Kluyveromyces lactis* (Dombrowski) van der Walt, teleomorph (ATCC Accession No. 76492); *Pichia angusta* (Teunisson et al.) Kurtzman, teleomorph deposited as *Hansenula polymorpha* de Morais et Maia, teleomorph (ATCC Accession No. 26012); *Aspergillus niger* van Tieghem, anamorph (ATCC Accession No. 9029); *Aspergillus niger* van Tieghem, anamorph (ATCC Accession No. 16404); *Aspergillus nidulans* (Eidam) Winter, anamorph (ATCC Accession No. 48756); and *Yarrowia lipolytica* (Wickerham et al.) van der Walt et von Arx, teleomorph (ATCC Accession No. 201847).

Suitable promoters for *S. cerevisiae* include those associated with the PGKI gene, GAL1 or GAL10 genes, CYCI, PH05, TRP1, ADH1, ADH2, the genes for glyceraldehyde-3-phosphate dehydrogenase, hexokinase, pyruvate decarboxylase, phosphofructokinase, triose phosphate isomerase, phosphoglucose isomerase, glucokinase, alpha-mating factor pheromone, [a mating factor pheromone], the PRBI promoter, the GUT2 promoter, the GPDI promoter, and hybrid promoters involving hybrids of parts of 5' regulatory regions with parts of 5' regulatory regions of other promoters or with upstream activation sites (e.g. the promoter of EP-A-258 067).

Convenient regulatable promoters for use in *Schizosaccharomyces pombe* are the thiamine-repressible promoter from the nmt gene as described by Maundrell (1990) J. Biol. Chem. 265, 10857-10864 and the glucose repressible jbp1 gene promoter as described by Hoffman & Winston (1990) Genetics 124, 807-816.

Methods of transforming *Pichia* for expression of foreign genes are taught in, for example, Cregg et al. (1993), and various Phillips patents (e.g. U.S. Pat. No. 4,857,467, incorporated herein by reference), and *Pichia* expression kits are commercially available from Invitrogen BV, Leek, Netherlands, and Invitrogen Corp., San Diego, Calif. Suitable promoters include AOX1 and AOX2. Gleeson et al. (1986) J. Gen. Microbiol. 132, 3459-3465 include information on *Hansenula* vectors and transformation, suitable promoters being MOX1 and FMD1; whilst EP 361 991, Fleer et al. (1991) and other publications from Rhone-Poulenc Rorer teach how to express foreign proteins in *Kluyveromyces* spp., a suitable promoter being PGKI.

The transcription termination signal is preferably the 3' flanking sequence of a eukaryotic gene which contains proper signals for transcription termination and polyadenylation. Suitable 3' flanking sequences may, for example, be those of the gene naturally linked to the expression control sequence used, i.e. may correspond to the promoter. Alternatively, they may be different in which case the termination signal of the *S. cerevisiae* ADHI gene is preferred.

In certain embodiments, the desired antigen-binding construct protein is initially expressed with a secretion leader sequence, which may be any leader effective in the yeast chosen. Leaders useful in *S. cerevisiae* include that from the mating factor alpha polypeptide (MFα-1) and the hybrid leaders of EP-A-387 319. Such leaders (or signals) are cleaved by the yeast before the mature protein is released into the surrounding medium. Further such leaders include those of *S. cerevisiae* invertase (SUC2) disclosed in JP 62-096086 (granted as 911036516), acid phosphatase (PH05), the pre-sequence of MFα-1, 0 glucanase (BGL2) and killer toxin; *S. diastaticus* glucoarnylase II; *S. carlsbergensis* α-galactosidase (MEL1); *K. lactis* killer toxin; and *Candida* glucoarnylase.

Post-Translational Modifications

In certain embodiments are antigen-binding constructs described herein, which are differentially modified during or after translation. In some embodiments, the modification is at least one of: glycosylation, acetylation, phosphorylation, amidation, derivatization by known protecting/blocking groups, proteolytic cleavage and linkage to an antibody molecule or antigen-binding construct or other cellular ligand. In some embodiments, the antigen-binding construct is chemically modified by known techniques, including but not limited, to specific chemical cleavage by cyanogen bromide, trypsin, chymotrypsin, papain, V8 protease, NaBH$_4$; acetylation, formylation, oxidation, reduction; and metabolic synthesis in the presence of tunicamycin.

Additional post-translational modifications of antigen-binding constructs described herein include, for example, N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of procaryotic host cell expression. The antigen-binding constructs described herein are modified with a detectable label, such as an enzymatic, fluorescent, isotopic or affinity label to allow for detection and isolation of the protein. In certain embodiments, examples of suitable enzyme labels include horseradish peroxidase, alkaline phosphatase, beta-galactosidase, or acetylcholinesterase; examples of suitable prosthetic group complexes include streptavidin biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include iodine, carbon, sulfur, tritium, indium, technetium, thallium, gallium, palladium, molybdenum, xenon, fluorine.

In specific embodiments, antigen-binding constructs described herein are attached to macrocyclic chelators that associate with radiometal ions.

In some embodiments, the antigen-binding constructs described herein are modified by either natural processes, such as post-translational processing, or by chemical modification techniques which are well known in the art. In certain embodiments, the same type of modification may be present in the same or varying degrees at several sites in a given polypeptide. In certain embodiments, polypeptides from antigen-binding constructs described herein are branched, for example, as a result of ubiquitination, and in some embodiments are cyclic, with or without branching. Cyclic, branched, and branched cyclic polypeptides are a result from posttranslation natural processes or made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W. H. Freeman and Company, New York (1993); POST-TRANSLATIONAL COVALENT MODIFICATION OF PROTEINS, B. C. Johnson, Ed., Academic Press, New York, pgs. 1-12 (1983); Seifter et al., Meth. Enzymol. 182:626-646 (1990); Rattan et al., Ann. N.Y. Acad. Sci. 663:48-62 (1992)).

In certain embodiments, antigen-binding constructs described herein are attached to solid supports, which are particularly useful for immunoassays or purification of polypeptides that are bound by, that bind to, or associate with proteins as described herein. Such solid supports include, but are not limited to, glass, cellulose, polyacrylamide, nylon, polystyrene, polyvinyl chloride or polypropylene.

Use of the Antigen-Binding Constructs in the Treatment of Neurodegenerative Diseases In certain embodiments, provided is a method of treating a disease or disorder characterized by TDP-43 proteinopathy comprising administering to a subject in which such treatment, prevention or amelioration is desired, an TDP-43 antigen-binding construct described herein, in an amount effective to treat, prevent or ameliorate the disease or disorder.

"Disorder" or "disease" refers to any condition that would benefit from treatment with an anti-TDP-43 antibody or method as described herein. This includes chronic and acute disorders or diseases including those pathological conditions which predispose the mammal to the disorder in question. In a preferred embodiment, the diseases being treated with the antigen-binding constructs described herein are associated with TDP proteinopathy. These include, without limitation, amyotophic lateral sclerosis (ALS), Parkinson's disease, frontotemporal lobar degeneration (FTLD) motor neuron disease, Alzheimer's disease, dementia with Lewy bodies, Huntington's disease, Lewy body disease, mild cognitive impairment (MCI), or TDP-43 abnormalities triggered by nerve injury, brain trauma, brain ischemia (stroke).

The term "subject" refers to an animal, in some embodiments a mammal, which is the object of treatment, observation or experiment. An animal may be a human, a non-human primate, a companion animal (e.g., dogs, cats, and the like), farm animal (e.g., cows, sheep, pigs, horses, and the like) or a laboratory animal (e.g., rats, mice, guinea pigs, and the like).

The term "mammal" as used herein includes but is not limited to humans, non-human primates, canines, felines, murines, bovines, equines, and porcines. In some embodiments, the subject being treated with the anti-TDP-43 antigen-binding constructs is a mouse or a human.

"Treatment" refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishing of any direct or indirect pathological consequences of the disease, decreasing the rate of disease progression, amelioration or palliation of the disease state, and remission or improved prognosis. In some embodiments, antigen-binding constructs as described herein are used to delay development of a disease or disorder.

Desirable effects of treatment include, but are not limited to, preventing occurrence or recurrence of disease, alleviation of symptoms, diminishment of any direct or indirect pathological consequences of the disease, decreasing the rate of disease progression, amelioration or palliation of the disease state, and remission or improved prognosis. In some embodiments, constructs described herein are used to delay development of a disease or to slow the progression of a disease.

The term "effective amount" as used herein refers to that amount of construct being administered, which will accomplish the goal of the recited method, e.g., relieve to some extent one or more of the symptoms of the disease, condition or disorder being treated. The amount of the composition described herein which will be effective in the treatment, inhibition and prevention of a disease or disorder associated with aberrant expression and/or activity of a therapeutic protein can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses are extrapolated from dose-response curves derived from in vitro or animal model test systems.

The TDP-43 antigen-binding constructs described herein are administered to the subject. Various delivery systems are known and can be used to administer an antigen-binding construct formulation described herein, e.g., encapsulation in liposomes, microparticles, microcapsules, recombinant cells capable of expressing the compound, receptor-mediated endocytosis (see, e.g., Wu and Wu, J. Biol. Chem. 262:4429-4432 (1987)), construction of a nucleic acid as part of a retroviral or other vector, etc. Methods of introduction include but are not limited to intradermal, intramuscular, intraperitoneal, intrathecal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

In addition, in certain embodiments, it is desirable to introduce the antigen-binding construct compositions described herein into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it is desirable to administer the antigen-binding constructs, or compositions described herein locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antigen-binding construct, as described herein, care must be taken to use materials to which the protein does not absorb.

In another embodiment, the antigen-binding constructs or composition can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid).

In yet another embodiment, the antigen-binding constructs or composition can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled release system can be placed in proximity of the therapeutic target, e.g., the brain, thus requiring only a fraction of the systemic dose (see, e.g., Goodson, in Medical Applications of Controlled Release, vol. 2, pp. 115-138 (1984)).

Gene Therapy

In some embodiments, nucleic acid encoding antigen-binding constructs described herein can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., Proc. Natl. Acad. Sci. USA 88:1864-1868 (1991)), etc. Alternatively, a nucleic acid can be introduced intracellularly and incorporated within host cell DNA for expression, by homologous recombination.

In a specific embodiment, the nucleic acid encoding the antigen-binding construct is inserted into an adeno-associated virus (AAV) vector (see Patel et al., Molecular Therapy 22 (3) 498-510 (2014) and Example 12 herein). The viral vector may be administered to the subject systemically or locally, for example by intrathecal injection.

In certain embodiments an antigen-binding construct described herein is administered as a combination with antigen-binding constructs with non-overlapping binding target epitopes on TDP-43.

The amount of the antigen-binding construct which will be effective in the treatment, inhibition and prevention of a disease or disorder can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses are extrapolated from dose-response curves derived from in vitro or animal model test systems.

Also included herein is a method of preventing or delaying the onset of at least one symptom of a TDP-43 proteinopathy in a subject in need thereof comprising administering a therapeutically effective amount of an TDP-43 antigen binding construct described herein. In one embodiment, the subject is an experimental organism, such as, but not limited to, a transgenic mouse. In one embodiment, the subject is a human.

The antigen-binding constructs described herein may be administered alone or in combination with other types of treatments used for neurodegenerative diseases, such as Rilutek®.

Methods of Characterizing Antigen-Binding Constructs

TDP-43 antigen-binding constructs described herein can be characterized using any in vivo or in vitro models of TDP-43 proteinopathies. A person skilled in the art understands that an TDP-43 antigen-binding construct can be characterized in a mouse model for TDP-43 proteinopathies, for example, one of the animal models for TDP-43 proteinopathies described in Swarup et al. Brain 134: 2610-2626 (2011). Swarup et al. 2011 describes three transgenic mouse models for TDP proteinopathies: wild type, G348C and A315T. These transgenic mice exhibit motor and cognitive impairment (as measured by the Barnes maze test, the step through passive avoidance test and the accelerating rotarod test). Additionally, the mice exhibit cytoplasmic TDP-43-positive ubiquitinated inclusions, intermediate filament abnormalities, axonopathy and neuroinflammation. Additional animal models are described in Wegorzewska et al, Proc. Natl. Acad. Sci. U.S.A. 106 (2009), 18809-14; Gurney et al, Science 264 (1994), 1 772-75; Shan et al, Neurophar-macol. Letters 458 (2009), 70-74; Wils et al, Proc. Natl. Acad. Sci. USA. 106 (2010), 3858-63; Duchen and Strich, J. Neurol. Neurosurg, Psychiatry 31 (1968), 535-42; Dennis and Citron, Neuroscience 185 (2009), 745-50; Swamp et al, Brain 134 (2011), 2610-2626; Sgaz et al, J Clin invest. 121(2):726-38 (2011); Caccamo et al. Am J Pathol. 180(1): 293-302 (2012), Cannon et al, Acta Neuropathol. 123(6): 807-23 (2012), Custer et al, Hum Moi Genet. 19(9): 1741-55 (2010): and Tatom et al, oL Ther. 17 (2009), 607-613. These animal models may be used to evaluate the TDP-43 antigen-binding constructs described herein.

An experimental model of TDP-43 proteinopathy can be used in a preventative setting or it can be used in a therapeutic setting. In a preventative setting, the dosing of animals starts prior to the onset of the TDP-43 proteinopathy or symptoms thereof. An TDP-43 antigen-binding construct described herein may be evaluated for its ability to prevent, reduce or delay the onset of TDP-43 proteinopathy or symptoms thereof. In a therapeutic model, the dosing of animals starts after the onset of TDP-43 proteinopathy or a symptom thereof. In a therapeutic setting, an TDP-43 antigen-binding constructs is evaluated for its ability to treat, reduce or alleviate the TDP-43 proteinopathy or a symptom thereof. Symptoms of the TDP-43 proteinopathies include, but are not limited to, accumulation of pathological TDP-43 deposits, pathological TDP-43 distribution, phosphorylated TDP-43, or insoluble TDP-43 fractions in the neurons, brain, spinal cord, cerebrospinal fluid or serum of the experimental object. A positive preventative or therapeutic outcome in any animal model of TDP-43 proteinopathies indicates that the particular TDP-43 antigen-binding construct can be used for preventative or therapeutic purposes in a subject other than the experimental model organism, for example, it can be used to treat TDP-43 proteinopathies in a human subject in need thereof.

In one embodiment, an TDP-43 antigen-binding construct can be administered to a TDP-43 proteinopathy mouse model and corresponding control wild type mice. The antigen-binding construct administered can be a murine antibody, or a human-murine chimera. The TDP-43 antigen-binding constructs can be administered by any means known in the art, for example, by intraperitoneal, intracranial, intramuscular, intrathecal, intravenous, subcutaneous, oral, and aerosol administration. Experimental animals can be given one, two, three, four, five or more doses of the TDP-43 antigen-binding constructs or a control composition, such as PBS. In one embodiment, experimental animals will be administered one or two doses of an TDP-43 antigen-binding construct. In another embodiment, the animals are chronically dosed with the TDP-43 antigen-binding constructs over several weeks or months. A skilled, artisan can readily design a dosing regimen that fits the experimental purpose, for example, dosing regimen for acute studies, dosing regimen for chronic studies, dosing regimen for toxicity studies, dosing regimen for preventative or therapeutic studies. The presence of the TDP-43 antigen-binding constructs in a particular tissue compartment of the experimental animals, for example, but not limited to, serum, blood, cerebrospinal fluid, brain or spinal cord tissue, can be established using well know methods of the art. In one embodiment, a TDP-43 antigen-binding construct is capable of penetrating the blood brain barrier. In another embodiment, a TDP-43 antigen-binding constructs is capable of entering neurons. By adjusting the dose of the TDP-43 antigen-binding construct and the dosing frequency, a desired concentration can be maintained in the experimental animals. Any effect of a TDP-43 antigen-binding construct as described herein in the TDP-43 proteinopathy models can be assessed by comparing the level, biochemical characteristics or distribution of TDP-43 in the treated and control animals. In one embodiment, a TDP-43 antigen-binding construct is capable of reducing the level, amount or concentration of TDP-43 inclusions in the brain or spinal cord in an animal model. The construct can reduce the level, amount or concentration of TDP-43 inclusions by at least about 5%, 10%, 20%, 30%, 50%, 70%, 90% or more. In another embodiment, a TDP-43 antigen-binding construct is capable of reducing the number or frequency of TDP-43 inclusion-positive neurons in the brain or spinal cord in an animal model, for example, by at least about 5%, 10%, 20%, 30%, 50% o, 70%, 90% or more. The effect of a TDP-43 antigen-binding construct can also be assessed by examining the distribution and biochemical properties of TDP-43 following administration. In one embodiment, a TDP-43 antigen-binding construct is capable of reducing the amount or concentration of cytoplasmic or nuclear TDP-43 protein in the brain or spinal cord of an animal model, for example, by at least about 5%, 10%, 20%, 30%, 50%, 70%, 90% or more, in another embodiment, it is capable of reducing the amount or concentration of neuritic TDP-43 protein in the brain or spinal cord of an animal model, for example, by at least about 5%, 10%, 20%, 30%, 50%, 70%. 90% or more, in a further embodiment, it can reduce the amount or concentration of phosphorylated TDP-43 protein in the brain or spinal cord in an animal model, for example, by at least about 5%, 10%, 20%, 30%, 50%, 70%, 90% or more. Phosphorylated TDP-43 can be detected using antibodies specific for pathologically phosphorylated forms of TDP-43, such as p403/p404 and p409/p410. Hasegawa et al., Ann Neurol, 64: 60-70 (2008). A TDP-43 antigen-binding construct can also alter, for example, reduce or increase TDP-43 concentration in the blood, serum or cerebrospinal fluid of an animal model, for example, by at least about 5%, 10%, 20%, 30%, 50%, 70%, 90% or more, in one embodiment, the % reduction or increase is relative compared to the level, number, frequency, amount or concentration that existed before treatment, or to the level, number, frequency, amount or concentration that, exist in an untreated/control treated subject.

In one embodiment, a TDP-43 antigen-binding construct can prevent or delay the onset of at least one symptom of a TDP-43 proteinopathy in a subject. In one embodiment, a TDP-43 antigen-binding construct can reduce or eliminate at least one symptom of a TDP-43 proteinopathy in a subject. The symptom can be the formation of pathological TDP-43 deposits, phosphorylated TDP-43 deposits, or insoluble TDP-43 deposits. The symptom can also be the presence, or elevated concentration or amount, of TDP-43 in the serum, blood, urine or cerebrospinal fluid, wherein elevated concentration amount is compared to a healthy subject. In one specific embodiment, the symptom is the presence of TDP-43-associated NF-kB. The symptom can be a neurological symptom., for example, loss of motor function or cognitive impairment. In one embodiment, memory impairment is assessed using the Barnes maze test or the step through passive avoidance test. In one embodiment motor function impairment is assessed using the accelerating rotarod test. In one embodiment, at least one symptom is reduced by at least about 5%, 10%, 15%, 20%, 30%, 50%, 70%, or 90%. In another embodiment, the latency time on the rotarod apparatus is significantly higher in a treated subject than in a control subject. In a specific embodiment, the rotarod latency time is increased by at least about 5%, 10%, 20%, 30%, 40%, 50%, 60%, 70%, 80%, or 90%.

Kits and Articles of Manufacture

Also described herein are kits comprising one or more anti-TDP-43 antigen binding constructs. Individual components of the kit would be packaged in separate containers and, associated with such containers, can be a notice in the form prescribed by a governmental agency regulating the manufacture, use or sale of pharmaceuticals or biological products, which notice reflects approval by the agency of manufacture, use or sale. The kit may optionally contain instructions or directions outlining the method of use or administration regimen for the antigen binding construct.

When one or more components of the kit are provided as solutions, for example an aqueous solution, or a sterile aqueous solution, the container means may itself be an inhalant, syringe, pipette, eye dropper, or other such like apparatus, from which the solution may be administered to a subject or applied to and mixed with the other components of the kit.

The components of the kit may also be provided in dried or lyophilized form and the kit can additionally contain a suitable solvent for reconstitution of the lyophilized components. Irrespective of the number or type of containers, the kits described herein also may comprise an instrument for assisting with the administration of the composition to a patient. Such an instrument may be an inhalant, nasal spray device, syringe, pipette, forceps, measured spoon, eye dropper or similar medically approved delivery vehicle.

In another aspect described herein, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is a T cell activating antigen binding construct described herein. The label or package insert indicates that the composition is used for treating the condition of choice. Moreover, the article of manufacture may comprise (a) a first container with a composition contained therein, wherein the composition comprises an antigen-binding construct described herein; and (b) a second container with a composition contained therein, wherein the composition comprises a further cytotoxic or otherwise therapeutic agent. The article of manufacture in this embodiment described herein may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Use of the TDP-43-Binding Constructs in the Diagnosis and Monitoring of TDP-43 Proteinopathies TDP-43 antigen-binding constructs may be used in the diagnosis of TDP-43 proteinopathies, particularly amyotrophic lateral sclerosis and/or frontotemporal lobar degeneration. Provided herein is the use of the TDP-43 antigen-binding constructs in the diagnosis and/or monitoring of a subject predisposed or suspected of developing a neurodegenerative disease or suffering from a neurodegenerative disease. The TDP-43 antigen-binding constructs may also be used in monitoring the efficacy of a treatment administered to a subject suffering from a TDP proteinopathy.

Assay methods are provided in co-owned patent application published as WO 2012/174666A1 (herein incorporated by reference) for determining the level of interaction between a TDP-43 polypeptide or fragment thereof and a NF-kB p65 polypeptide or fragment thereof in a biological sample of the subject. Such assay methods may employ a TDP-43 binding construct described herein. An elevated level of interaction between TDP-43 polypeptide or fragment thereof and p65 polypeptide or fragment thereof in the biological sample relative to a reference level of interaction between TDP-43 polypeptide or fragment thereof and p65 polypeptide or fragment thereof indicates that the subject is predisposed or suspected of developing a neurodegenerative disease or is suffering from a neurodegenerative disease. Further methods of using the TDP-43 antigen-binding constructs described herein to detect the association of TDP-43 and NF-kB are provided in the Examples below.

In another embodiment the TDP-43 antigen-binding constructs or nucleic acids encoding them may be used in a diagnostic composition as reagents in immuno- or nucleic acid-based diagnostic methods. The TDP-43 antigen-binding constructs as described herein are, for example, suited for use in immunoassays in which they can be utilized in liquid phase or bound to a solid phase carrier. Examples of immunoassays which can utilize the TDP-43 antigen-binding constructs as described herein are competitive and non-competitive immunoassays in either a direct or indirect format. Examples of such immunoassays are the radioimmunoassay (RIA), the sandwich (immunometric assay), flow cytometry and the Western blot assay.

The antigen-binding constructs as described herein may be labeled for use in an assay. There are many different labels and methods of labeling known to those of ordinary skill in the art. Examples of the types of labels which can be used in one embodiment include enzymes, radioisotopes, colloidal metals, fluorescent compounds, chemiluminescent compounds, and bioluminescent compounds.

In a further embodiment, the TDP-43 antigen-binding constructs as described herein can also be used in a method for the diagnosis of a disorder in an individual by obtaining a sample from the tested individual which can be a blood sample, a lymph sample, cerebrospinal fluid, or a neural tissue biopsy sample and contacting the sample with a TDP-43 antigen-binding constructs under conditions enabling the formation of antibody-antigen complexes. The level of such complexes is then determined by methods known in the art. A level significantly higher than that formed in a control sample indicating the disease in the tested individual. One embodiment, is a method of diagnosing a TDP-43 proteinopathy in a subject, the method comprising: (a) assessing the level of TDP-43 in a sample from the subject to be diagnosed with an TDP-43 antigen-binding construct, and (b) comparing the level of TDP-43 observed to a reference standard that indicates the level of the TDP-43 in one or more control subjects, wherein a difference or similarity between the level of the TDP-43 and the reference standard indicates that the subject suffers from a TDP-43 proteinopathy. The subject to be diagnosed can be asymptomatic or preclinical for the disease. In one embodiment, the control subject has a TDP-43 proteinopathy, for example ALS or FTLD, wherein a similarity between the level of TDP-43 and the reference standard indicates that the subject, to be diagnosed has a TDP-43 proteinopathy.

The level of TDP-43 can be assessed by any suitable method known in the art comprising, e.g., analyzing TDP-43 by one or more techniques chosen from Western blot, immunoprecipitation, enzyme-linked immunosorbent assay (ELISA), radioimmunoassay (RIA), fluorescent activated cell sorting (FACS), or gel electrophoresis.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for. The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, Biochemistry (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences*, 18th Edition (Easton, Pa.: Mack Publishing Company, 1990); Carey and Sundberg *Advanced Organic Chemistry* $3^{rd}$ Ed. (Plenum Press) Vols A and B(1992).

Example 1: Generation of Exemplary Monoclonal Antibodies Against the TDP-43 RRM1 Domain of TDP-43

A series of exemplary monoclonal antibodies against a recombinant protein encoding the RRMI domain of TDP-43 were generated. The TDP-43 fragment used as antigen was generated and purified as follows. The EcoR1-Not1 428 bp hTDP43 cDNA fragment encoding RRM1 was PCR-amplified and cloned into the pGEX-6P-1 vector (GE Healthcare). This recombinant plasmid was used to transform the *E. coli* host BL21 for the expression of the 136 aa protein encoding all the RRM1 domain of hTDP43. The 15.68 kDa recombinant protein was subsequently purified using the Glutathione S-transferase (GST) gene fusion system (GE Healthcare).

C57B16 mice were immunized with this polypeptide fragment, comprising amino acids 40-176 of TDP-43 (see Table A for sequence). The exemplary anti-TDP-43 monoclonal antibodies that were obtained using standard hybridoma technology yielded an immunodetection signal for TDP-43 protein when tested by immunoblotting after SDS-PAGE of spinal cord extracts from non-transgenic mice, as well as from transgenic mice over-expressing human TDP-43 (data not shown). Antibodies from three hybridoma clones C10, G8 and E6 also detected TDP-43 on immunoblots of nuclear extracts from mouse microglial BV-2 cells fractionated by SDS-PAGE (shown in FIG. 1).

Example 2: Human Recombinant NF-κB p65 Interacts Directly with Human Recombinant TDP-43

BSA 0.8 ug/ml or human recombinant TDP-43 in serial dilutions from 0.8 ug/ml to 0.0125 ug/ml were prepared in PBS, loaded on ELISA microplates (6 wells per conditions) and incubated overnight. Human recombinant p65-His-Tag (Enzo Life Sciences) was prepared at the concentration of 0.2 ug/ml, added to all wells and incubated 2 h. After 2 h incubation in Blocking Buffer, anti-His-Tag-HRP (1:10.000) (Abcam) was prepared in Diluent Solutions, loaded on the plate and incubated 2h. Substrate Solution was added and Absorbance read at 450 nm. The results are shown in FIG. 2. Values are expressed as mean±sem.

Example 3: Interaction Between Recombinant TDP-43 and NF-κB p65 is Inhibited by Exemplary Bivalent Monoclonal Anti-RRM1-TDP-43 Antibodies C10, G8 and E6

Human recombinant TDP-43 was prepared at the concentration of 0.2 ug/ml, loaded on ELISA microplates and incubated overnight. p65-His-Tag (0.4 ug/ml) was mixed 1:1 with PBS, BSA (0.4 ug/ml), anti-TDP-43 polyclonal antibodies (Proteintech) (0.4 ug/ml IgG) or anti-RRM1-TDP-43 monoclonal antibodies (C10, G8 or E6 monoclonals having an Fab/Fab format with an Fc domain) (0.4 ug/ml IgG) to reach the final concentration of 0.2 ug/ml p65 and 0.2 ug/ml interfering antibody. Mixed solutions were loaded on the plate (8 wells per condition) and incubated 2 h. After 2 h incubation in Blocking Buffer, anti-His-Tag-HRP (1:10.000) is prepared in Diluent Solutions, loaded on the plate and incubated 2 h. Substrate Solution is added and Absorbance read at 450 nm. The results are shown in FIG. 3, and demonstrate that all 3 of the monoclonal antibodies C10, G8 and E6 block the interaction between TDP-43 and NF-κB p65 to a much greater extent than the polyclonal anti-TDP antibody. Values are expressed as mean±sem.

Example 4: Derivation of Single Chain Anti-TDP-43 Antibodies

The mRNAs were isolated from the appropriate hybridoma cell lines from Example 1 to derive cDNAs encoding scFv antibodies under the control of a CMV promoter. The variable regions of heavy chain (VH) and light chain (Vk) were amplified separately from first-strand cDNA by using a mixture of PCR primers and were cloned into the pBZUT7 (as described in Patel et al. Mol Ther., 22 (3), 498-510 2014) vector and sequenced. The VH and Vk domains were assembled and linked together to yield a full-length scFv gene. The scFv gene was constructed in a VH-linker-Vk format together with a standard flexible 20-amino acid linker (Gly4Ser)3 and it was then subcloned upstream of the Myc-tagged Psw1 scFVD1.3 Tag1 expression vector (Patel et al. op. cit.) to generate scFv-TDP-43. Exemplary clones were then sequenced. The scFv generated contained a murine immunoglobulin (Ig) κ-secretory signal for efficient secretion and a human c-myc epitope to facilitate detection. A schematic drawing of these constructs is shown in FIG. 4.

Example 5: Anti-TDP-43 Antibodies Having an scFv Format Localize in the Cytoplasm and Nucleus of HEK 293 Cells, and are Secreted Hek 293 cells were transiently transfected with pScFv9 expression plasmid containing Igκ domain, Myc-tag and a combination of the two VH and Vκ obtained from the E6 clone, i.e. VH1Vk9, VH1Vk11, VH7Vk9 and VH7Vk11. A schematic representation of the constructs is shown in FIG. 4A. Cells were transfected with 4 μg of plasmid for 48 h and then collected. Cytoplasmic and nuclear fractions were obtained and loaded on a 12% gel. Rabbit polyclonal anti-myc antibody (Abcam) was used to detect the ScFv antibodies inside the cells. Media of transfected cells were collected, centrifuged at 5000 rpm for 15 min at 4° C. to eliminate debris and precipitated over-night at −20° C. The pellet was resuspended in loading buffer and loaded on 12% gel. The scFv antibodies were detected by blotting the membrane with mouse monoclonal anti-myc antibody (Santa Cruz). The results show that E6_VH1Vκ9 and E6_VH7Vκ9 scFv antibodies localized in both the cytoplasm and the nucleus of Hek 293 cells (FIG. 5). The scFv antibodies were also secreted into the medium (FIG. 5).

Example 6: Anti-TDP-43 Antibodies Having an scFv Format Detect TDP-43 RRM1 Domain Different concentrations of TDP-43 1-206 amino acid fragment, containing the RRM1 domain were loaded onto membranes by dot blot. Membranes were incubated overnight with media from Hek293 cells that had been transfected with pScFv9 expression plasmid containing the nucleic acids encoding E6_VH1Vk9 and E6_VH7Vk9. The myc signal was detected using anti-myc HRP antibody incubation. The results, shown in FIG. 6, demonstrate that E6_VH1Vk9 and E6_VH7Vk9 scFv antibodies are able to recognize specifically TDP-43.

Example 7: E6_VH1Vk9 and E6_VH7Vk9 Exemplary Antigen-Binding Constructs in an scFv Format Block the Interaction of TDP-43 with NF-κB p65

An ELISA assay was performed as described in EXAMPLE 2 using the conditioned medium from E6_VH1Vk9- and E6_VH7Vk9-expressing cells as a source of the antibodies. Medium from HEK293 cells that had been transfected with an empty pScFv9 cells, or an irrelevant insert (D1.3) were used as controls. The results show that both E6_VH1Vk9 and E6_VH7Vk9 are capable of blocking the TDP-43 interaction with NF-κB p65 (FIG. 7). The bivalent Fab/Fab format antibody E6 at a concentration of 0.4 ug/ml inhibited the TDP-43 interaction with NF-κB p65 to an even greater extent, and a TDP-43 polyclonal antibody inhibited, but to a lesser degree than the monoclonals.

Example 8: Antibodies Expressed in HEK293 Cells Interact with TDP-43 Intracellularly Cell lysates were made from E6_VH1Vk9- and E6_VH7Vk9-expressing HEK293 cells. The lysates were exposed to polyclonal anti-TDP 43 to immunoprecipate cellular TDP-43. Immunopreciptates were resolved using PAGE. The results are shown in FIG. 8, demonstrating that the scFv antibodies E6_VH1Vk9 and E6_VH7Vk9 (detected by a myc tag) were co-immunoprecipitated with TDP-43. This demonstrates that the antigen-binding constructs E6_VH1Vκ9 and E6_VH7Vκ9 bound to intracellular TDP-43.

Example 9: VH1Vk9 Antibody Blocks the Interaction of TDP-43 with NF-κB p65 in HEK293 Cells Cell lysates were made from E6_VH1Vk9-expressing HEK293 cells which have been treated with TNFα 4 hours. The lysates were exposed to polyclonal anti-TDP 43 antibody to immunoprecipate cellular TDP-43. Immunoprecipitates were resolved using PAGE. FIG. 9 shows an immunoblot in which an antibody against p65 was used to detect immunoprecipitates. The results show that decreased levels of NF-κB p65 were present when VH1Vk9 was expressed in the HEK293 cells. This indicates that VH1Vk9 interfered with the binding of TPD-43 to NF-κB p65 in the cell.

Example 10: Inhibition of NF-κB Activation by scFv Exemplary Antibodies Against TDP-43 in Cultured Cell Systems A cell line was previously generated by stable transfection of BV-2 microglial cells with stable insertion of a luciferase reporter 4 kBwt luciferase plasmid and subsequent selection with hygomycin (Swamp, 2011 J. Exp. Med. op cit.). Expression plasmid vectors encoding scFv anti-TDP-43 antibodies were transfected into these BV-2 cultured cells and transiently expressed for 48 hours. During the final 4 hours, cells were exposed to either PBS (control) or 500 ng/ml LPS. Cells were lysed with Glo Buffer (Promega) and 50 µl of lysates were loaded in replicates on a 96 well plate. Luciferase substrate was added following the assay procedures (Bright-Glo Luciferase Assay, Promega). RLU (relative light units) of luminescence were determined using an automatic plate reader and normalized on total proteins (µg) present in the well, as determined by protein quantification (Biorad).

The results shown in FIG. 10 demonstrate the activation of the NF-κB reporter gene was reduced after treatment with LPS in BV2 cells expressing either scFv antibody VH1Vκ9 or E6_VH7Vκ9. There was no effect of the antibodies on viability of BV2 cells (data not shown). We note that the scFv VH7-Vk9 antibody was more effective in reducing NF-κB activity of BV2 cells than the scFv VH1Vk9 antibody. The scFv VH7-Vk9 attenuated NF-κB activity by 32% whereas scFv VH1Vk9 reduced NF-κB activity by 13%. This is intriguing because these two scFv antibodies differ by only one amino acid, a Q (glutamine) instead of E (glutamic acid) in the scFv VH7-Vk9. Somehow this minor sequence variation appears to enhance the propensity of scFv E6_VH7Vκ9 to distribute in the nucleus (as shown in FIG. 5), a factor that may explain a more efficient inhibition of TDP-43 interaction with NF-κB p65 in the nucleus.

Example 11: Expression of scFv Antibodies in Neuro2A Cells Caused Reduction in Levels of Nuclear TDP-43

Neuro 2A cells were transiently transfected with E6_VH1Vk9, E6_Vh7Vk9 or an empty vector as in Example 5. After 48 hours, nuclear extracts were obtained from the cells and the amount of nuclear TDP-43 was quantified by ponceau staining. The results are shown in FIG. 11. Both E6_VH1Vk9, E6_Vh7Vk9 reduced the amount of nuclear TDP-43 significantly. In ALS, there is an upregulation of TDP-43 mRNA and protein levels (Swarup et al. J Exp med 2011). This result suggests that anti-TDP-43 scFv antibodies might confer protection by attenuating the upregulation of TDP-43 in ALS.

Example 12: Production of Adeno-Associated Viral AAV Vectors Containing scFv Antibodies The following protocol was used to produce pscAAV vectors containing E6-derived single chain antibodies. First, to produce unsecreted single chain antibodies (–IgK), a 773 bp fragment was obtained from pScFv9_E6VH1Vk9 and pScFv9_E6VHVk9 by PCR introducing XbaI restriction site before the VH sequence and NotI at the end of the myc sequence. Digestion of the scAAV-CMV-EGFP (described in McCarty et al. Gene Ther. 8: 1248-1254, 2001) with XbaI and NotI restriction enzymes allowed replacing the EGFP sequence with E6VH1Vk9(–IgK) and E6VH7Vk9(–IgK). Subsequently, the IgK sequence was obtained by pscFv9 plasmid using HindIII and PstI restriction enzymes. A XbaI/PstI fragment containing HindIII restriction site was inserted into corresponding restriction sites of pscAAV_E6VH1Vk9_NS and E6VH7Vk9 NS plasmids before the VH sequence. Finally, pscAAV plasmids were digested with HindIII and PstI and the IgK sequence was inserted to obtain pscAAV_E6VH1Vk9 and E6VH7Vk9 with a secretion signal. The secreted single chain antibodies were obtained by a standard method (Rabinowitz et al. J Virol., 76: 791-801 (2002)). Briefly, the fragment encompassing the ScFv expression cassette in pscFv9-E6VH1Vk9 and E6VH7Vk9 was excised using HindIII and EcoRV and cloned into the plasmid Bluescript SK(–) (Stratagene, Canada). It was then recloned as a SalI/NotI fragment into the XhoI/NotI digested scAAV-CMV-EGFP plasmid (McCarty et al. Gene Ther., 2011) replacing the EGFP encoding sequence and creating the pscAAV_E6VH1Vk9 and pscAAV_E6VH7Vk9 plasmids to be used in production of AAV recombinant viruses. Sequencing confirmed the correct insertions inside the plasmids.

Figure 12A:
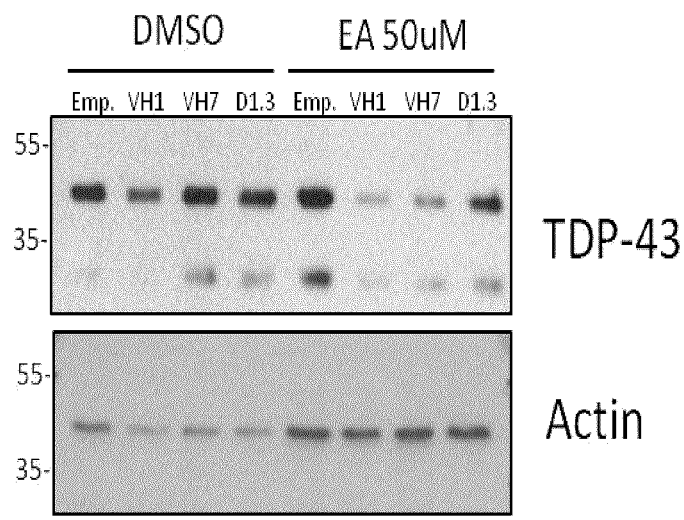
Figure 12B:
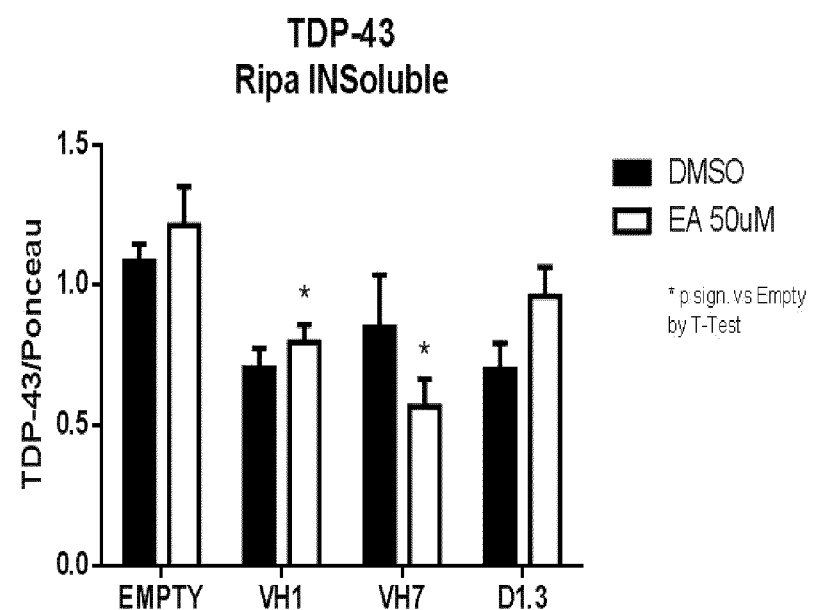

Example 13: E6 scFv Antibodies Reduce TDP-43 Insolubility in Ethacrynic Acid-Treated Cells Hek293 cells were transfected 72h in Optimem with 2 µg DNA and 5 µl Lipofectamine 2000 reagent (Invitrogen) with E6_V1 and E6_V7 scFv antibodies, empty plasmid or anti D1.3 scFv antibody and treated overnight with 50 µM ethacrynic acid (EA) to induce TDP-43 aggregation, or treated overnight with same volume of DMSO diluent as a control. The RIPA (radio-immunoprecipitation assay buffer) insoluble fraction was obtained. A representative western blot is shown in FIG. 12A and a representative dot blot analysis of TDP-43 is shown in FIG. 12B. The results show that both the E6_V1 and E6_V7 scFv antibodies reduced the amount of insoluble TDP-43 detected after EA treatment (n=3/conditions). *, p<0.05 versus Empty.

Immunofluorescence staining of the Hek293 transfected cells was conducted to localize TDP-43 in the cells (data not shown). In untransfected cells, TDP-43 mis-localized in the cytoplasm after EA treatment. However, in transfected cells expressing E6 V1 and E6_V7 TDP-43 remained in the nucleus after EA treatment, avoiding cytoplasmic localization and aggregation.

Example 14: E6 ScFv Antibodies Protect TDP-43 from Lysine Acetylation

Hek293 cells were transfected 48 h in Optimem with 2 µg DNA and 5 µl Lipofectamine 2000 reagent (Invitrogen) with E6 scFv antibodies V1 and V7, empty plasmid or anti D1.3 scFv antibody and treated for 4 hours with 50 ng/ml TNF alpha. Lysine acetylated proteins were immunoprecipitated using anti-acetyl-lysine antibody (Millipore) overnight in 300 µg total proteins lysate and the presence of lysine-acetylated TDP-43 was detected by western blotting for TDP-43 (Figure. 13). This result shows that that the E6 scFv antibodies protected TDP-43 from lysine acetylation. An empty transfection vector (EMT) was not protective, nor was a transfected control antibody D1.3. Lysine acetylation has been proposed as a novel post-translational modification controlling TDP-43 function and aggregation, and there is evidence that TDP-43 acetylation impairs RNA-binding and promotes accumulation of insoluble, hyper-phosphorylated TDP-43 species that largely resemble pathological inclusions in ALS and FTLD-TDP (Cohen T. J., Hwang A. W., Restrepo C. R., et al. Nat Com 2014).

The various embodiments described above can be combined to provide further embodiments. All of the U.S. patents, U.S. patent application publications, U.S. patent application, foreign patents, foreign patent application and non-patent publications referred to in this specification and/or listed in the Application Data Sheet are incorporated herein by reference, in their entirety. Aspects of the embodiments can be modified, if necessary to employ concepts of the various patents, application and publications to provide yet further embodiments. In the case of inconsistencies, the present disclosure will prevail.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. The scope of the claims should not be limited by the preferred embodiments set forth in the examples, but should be given the broadest interpretation consistent with the description as a whole.

We claim:

1. An antigen-binding construct or a pharmaceutical composition comprising said antigen-binding construct and a pharmaceutically acceptable excipient wherein said antigen-binding construct specifically binds a TAR-DNA binding protein 43 kDa (TDP-43) and comprises at least one heavy chain variable region VH and at least one variable light chain region (VL) and wherein said antigen-binding construct comprises three VH complementarity determining regions (CDRs) and three VL CDRs selected from the group consisting of:
   (a) the CDR1 (SEQ ID NO. 7), CDR2 (SEQ ID NO. 8) and CDR3 (SEQ ID NO. 9), of E6_VH1 and the CDR1 (SEQ ID NO. 13), CDR2 (SEQ ID NO. 14) and CDR3 (SEQ ID NO. 15) of E_6Vκ9;
   (b) the CDR1 (SEQ ID NO. 10), CDR2 (SEQ ID NO. 11) and CDR3 (SEQ ID NO12) of E6_VH7 and the CDR1 (SEQ ID NO. 13), CDR2 (SEQ ID NO. 14) and CDR3 (SEQ ID NO. 15) of E_6Vκ9;
   (c) the CDR1 (SEQ ID NO16), CDR2 (SEQ ID NO. 17) and CDR3 (SEQ ID NO. 18) of C10_VH3, and the CDR1 (SEQ ID NO. 22), CDR2 (SEQ ID NO. 23 and CDR3 (SEQ ID NO. 24) of C10_Vκ3; and
   (d) the CDR1 (SEQ ID NO19), CDR2 (SEQ ID NO. 20) and CDR3 (SEQ ID NO. 21) of C10_VH4 and the CDR1 (SEQ ID NO. 22), CDR2 (SEQ ID NO. 23 and CDR3 (SEQ ID NO. 24) of C10_Vκ3.

2. The antigen-binding construct of claim 1, comprising:
   i) the VH of E6_VH7 (SEQ ID NO. 2) and the VL of E6_Vκ9 (SEQ ID NO. 3);
   ii) the VH of E6_VH1 (SEQ ID NO. 1) and the VL of E6_Vκ9 (SEQ ID NO. 3);
   iii) the VH of C10_VH3 (SEQ ID NO. 4) and the VL of C10_Vκ3 (SEQ ID NO. 6); or
   iv) the VH of C10_VH4 (SEQ ID NO. 5) and the VL of C10_Vκ3 (SEQ ID NO. 6).

3. The antigen-binding construct of claim 1, wherein the construct comprises a peptide linker between the VH and VL, optionally wherein the linker comprises the amino acid sequence SSGGGGSGGGGSGGGGS (SEQ ID NO:47).

4. The antigen-binding construct of claim 1, wherein the construct comprises E6_Vh7Vκ9 (SEQ ID NO. 28), E6_Vh1Vκ9 (SEQ ID NO. 26), C10_VH3Vκ3 (SEQ ID NO. 30) or C10_VH4Vκ3 (SEQ ID NO. 32).

5. The antigen-binding construct of claim 1, wherein the construct comprises a secretory signal peptide.

6. The antigen-binding construct of claim 1, wherein the construct:
   a) has an scFv format, an Fab format, a single domain antibody format or an (Fab')$_2$ format;
   b) comprises an Fc domain; or
   c) is humanized.

7. A method of treating a disease characterized by TDP-43 proteinopathy selected from the group consisting of amyotrophic lateral sclerosis (ALS), Alzheimer's disease, motor neuron disease, Parkinson's disease, frontotemperal lobar degeneration (FTLD), mild cognitive impairment (MCI), Lewy body disease, brain trauma and cerebral ischemia in a subject in need thereof, comprising administering to the subject a therapeutically effective amount of:
   a) the antigen-binding construct of claim 1; or
   b) an adeno-associated viral (AAV) vector comprising at least one nucleic acid sequence that encodes at least one antigen-binding construct of claim 1.

8. A method of producing the antigen-binding construct of claim 1 comprising culturing a host cell under conditions suitable for expressing the antigen-binding construct, wherein the host cell comprises a polynucleotide encoding the antigen binding construct of claim 1, and purifying the construct.

9. An polynucleotide or set of isolated polynucleotides comprising at least one nucleic acid sequence that encodes at least one of the antigen-binding construct of claim 1; a vector or set of vectors comprising one or more of said polynucleotides or sets of polynucleotides; an isolated cell comprising said polynucleotide or set of polynucleotides; or a kit comprising the antigen-binding construct of claim 1 and instructions for use.

10. The antigen-binding construct of claim 1, wherein the construct comprises a peptide linker between the VH and VL, wherein the linker comprises the amino acid sequence SSGGGGSGGGGSGGGGS (SEQ ID NO:47).

11. The antigen-binding construct of claim 1, wherein the construct comprises a secretory signal peptide which is MGDNDIHFAFLSTGVHSQVQ (SEQ ID NO:48).

* * * * *